United States Patent [19]

Smith et al.

[11] Patent Number: 5,410,052

[45] Date of Patent: Apr. 25, 1995

[54] SYMMETRICAL AND UNSYMMETRICAL POLYALKYLAMINE METAL COMPLEXES FOR LIGAND EXTRACTION AND GENERATION

[75] Inventors: Kevin M. Smith; Joseph P. Ciccone, both of Davis, Calif.; N. Venkata Ramana, Burnaby, Canada

[73] Assignee: The Regents of the University of California, Oakland, Calif.

[21] Appl. No.: 587,973

[22] Filed: Sep. 25, 1990

Related U.S. Application Data

[60] Continuation-in-part of Ser. No. 558,516, Jul. 31, 1989, abandoned, which is a division of Ser. No. 306,730, Feb. 3, 1989, Pat. No. 4,959,135, which is a continuation-in-part of Ser. No. 18,891, Feb. 25, 1987, abandoned.

[51] Int. Cl.$^6$ ............... C07D 237/00; C07F 13/00; C07C 211/00

[52] U.S. Cl. .................. 544/224; 544/225; 546/181; 546/264; 548/305.1; 548/305.4; 548/306.1; 548/108; 548/109; 548/335.5; 548/312.7; 548/314.7; 548/315.1; 548/315.4; 548/312.1; 548/331.5; 548/340.1

[58] Field of Search ............... 556/45, 138; 564/512; 546/181, 264; 548/349; 544/224, 225

[56] References Cited

U.S. PATENT DOCUMENTS

| | | | |
|---|---|---|---|
| 4,189,306 | 2/1980 | Sandy | 44/68 |
| 4,451,270 | 5/1984 | Roman | 55/38 |
| 4,577,042 | 3/1986 | Collins et al. | 564/158 |
| 4,602,987 | 7/1986 | Bonaventura et al. | 204/129 |
| 4,605,475 | 8/1986 | Roberts et al. | 204/130 |
| 4,617,382 | 10/1986 | Back et al. | 534/693 |
| 4,629,544 | 12/1986 | Bonaventura et al. | 204/131 |

OTHER PUBLICATIONS

Harris, W. R., et al., "Electrochemical Investigation of Series of Peroxo-Bridged Binuclear Cobalt Complexs", *Inorganic Chemistry,* vol. 19, pp. 21–26 (1980).

Timmons, J. H., et al., "Stabilities of Metal Chelates of Imidazolyl-Containing Pentadentate Polyamines and their Dioxygen Comples", *Inorganic Chemistry,* vol. 17, pp. 2192–2197 (1978).

Timmons, J. H. et al. "Crystal and Molecular Structure μ-Peroxo-bis[(1,9-bis(2-pyridyl)-2,5,8-triazanonae)- cobalt (III)] Tetraiodide . . . ", *Inorganic Chemistry,* vol. 18, pp. 2977–2982 (1979).

Harris, W. R., et al., "Chelating Tendencies of Pyridyl-Containing Polyamines . . . ", *Inorganic Chemistry,* vol. 17, pp. 889–894 (1978).

Timmons, J. H., et al., "Crystal and Molecular Structure of μ-Peroxo-bis{[1,11-bis(2-pyridyl)-2,6,10-- triazaundencane]cobalt(III)} Tetraiodide Trihydrate . . . ", *Inorganic Chemistry,* vol. 18, pp. 1042–1047 (1979).

*Primary Examiner*—José G. Dees
*Assistant Examiner*—Porfirio Nazario
*Attorney, Agent, or Firm*—Phillips Moore Lempio & Finley

[57] ABSTRACT

Mthods and apparatus for the extraction of a ligand such as molecular oxygen from a first fluid environment and for release of a ligand such as molecular oxygen, as well as ligand carrier compounds therefore comprising linear, pentadentate polyalkylamines and transition metal ions. The carrier compounds have the general formula:

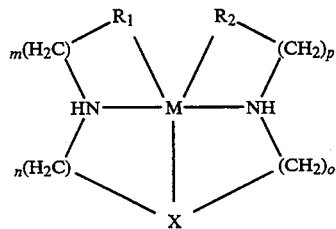

where, each of $R_1$ and $R_2$ is independently an organic group including a sulfur, an oxygen or a nitrogen coordinated to M;

each of m, n. o, and p is 1, 2 3, or 4;

X is selected from the group consisting of 2,6-pyridyl, 2,6-piperidyl, 2,5pyrrolyl, 2,4-imidazolyl, substituted heterocyclic amines, —O—, —S— >P—R$_3$, and >N—R$_3$ where R$_3$ is hydrogen, lower alkyl, or aralkyl; and M is a transition metal ion.

16 Claims, 23 Drawing Sheets

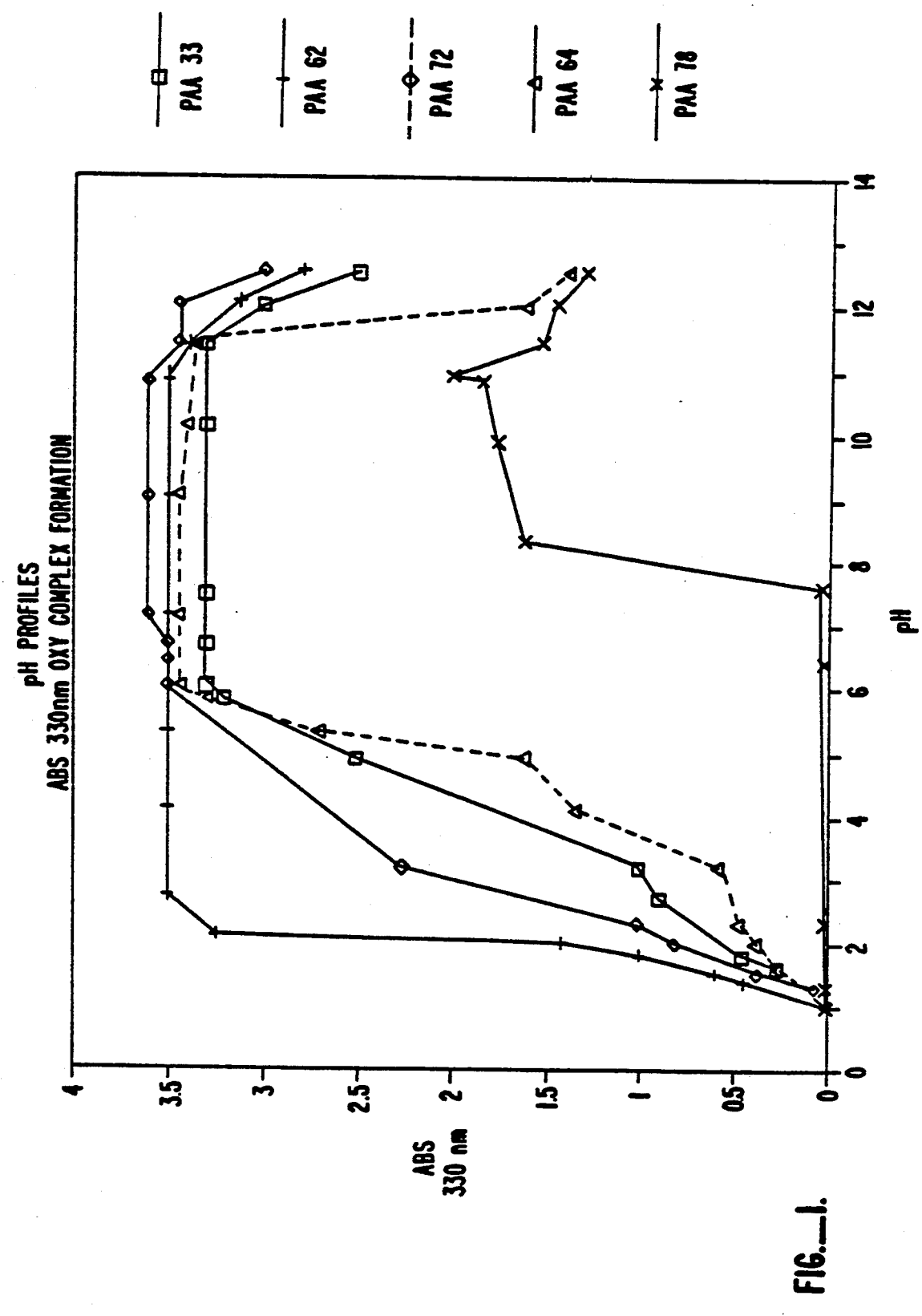
FIG._1.

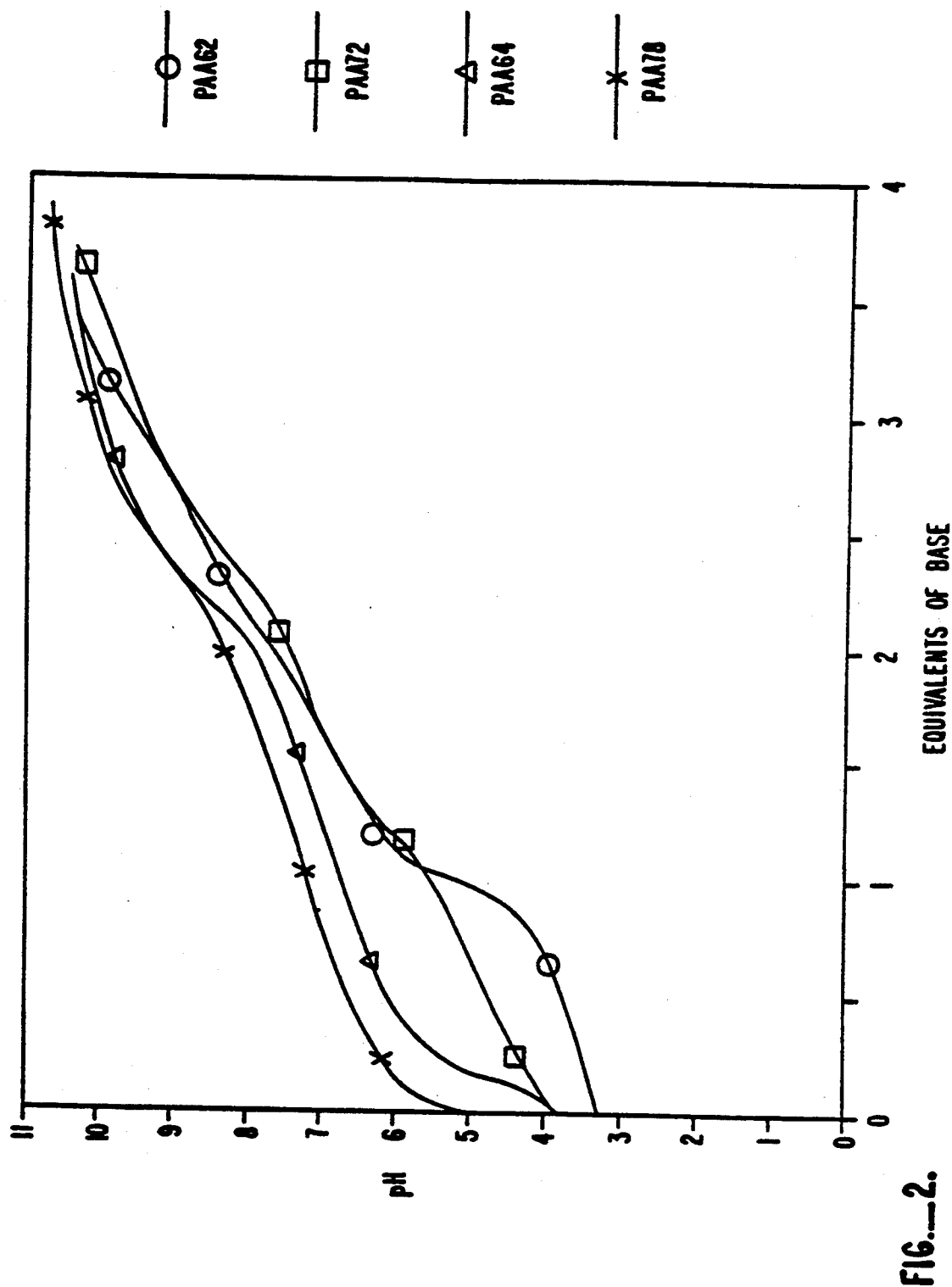
FIG._2.

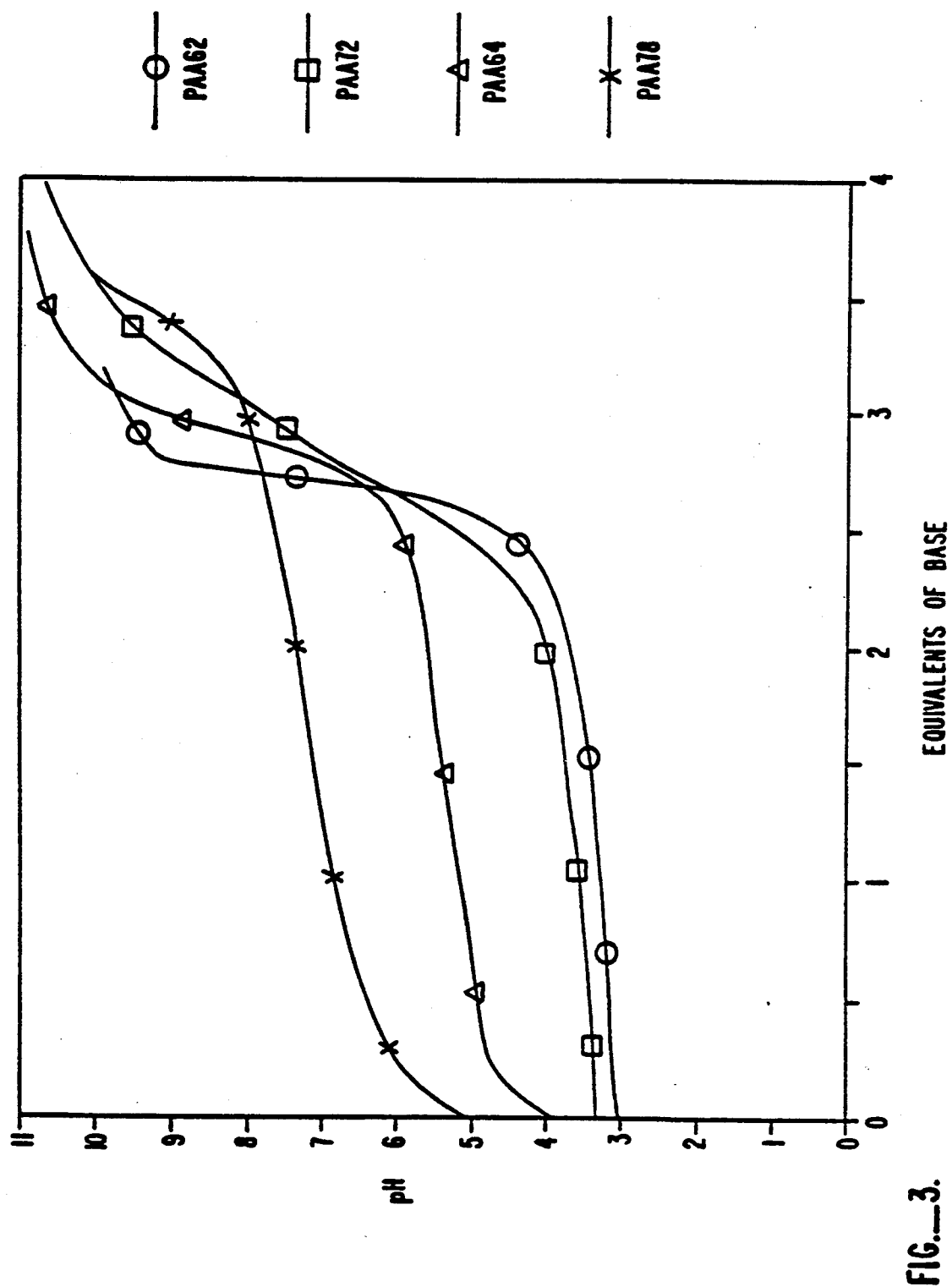
FIG._3.

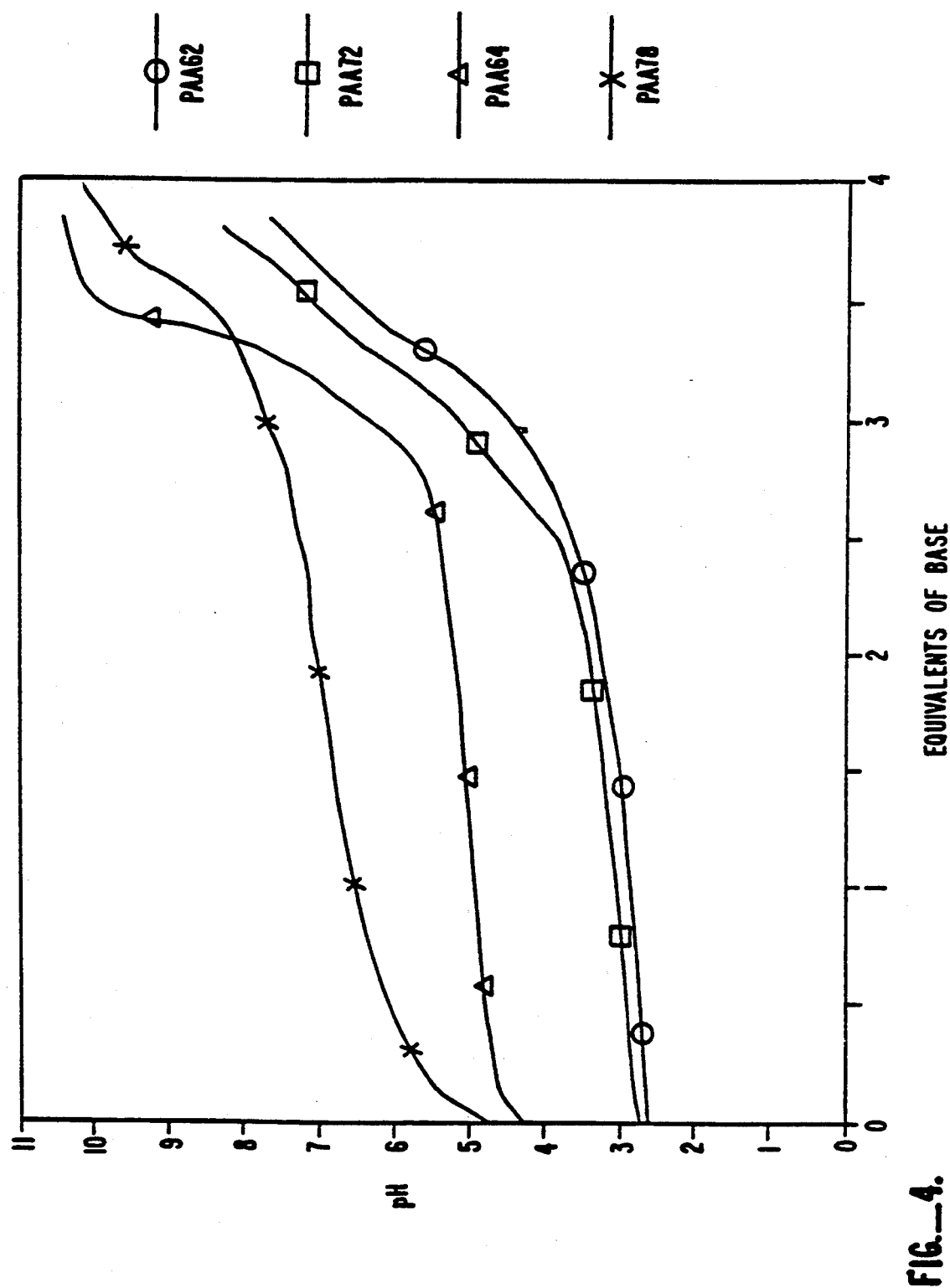
FIG._4.

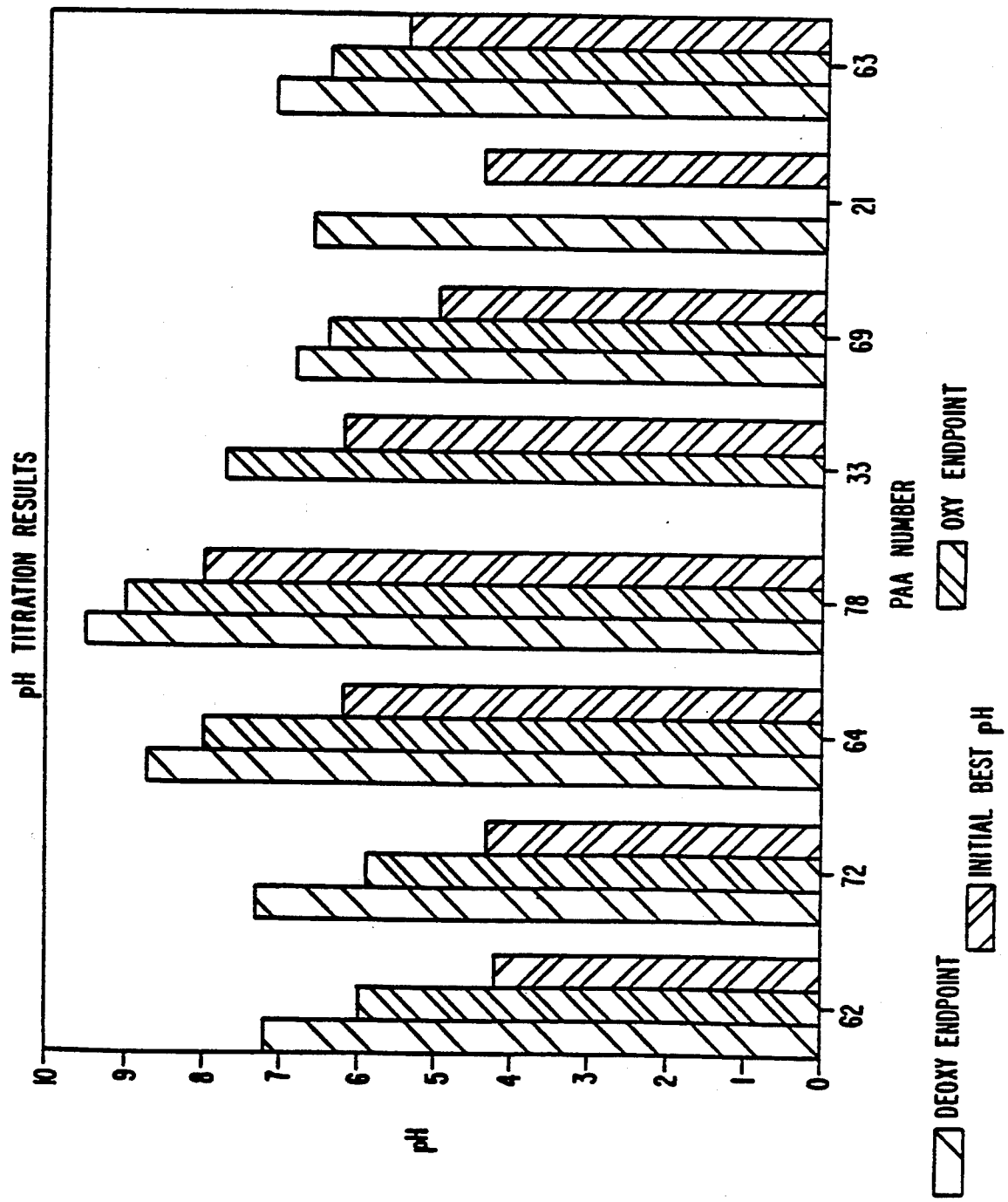
FIG._5.

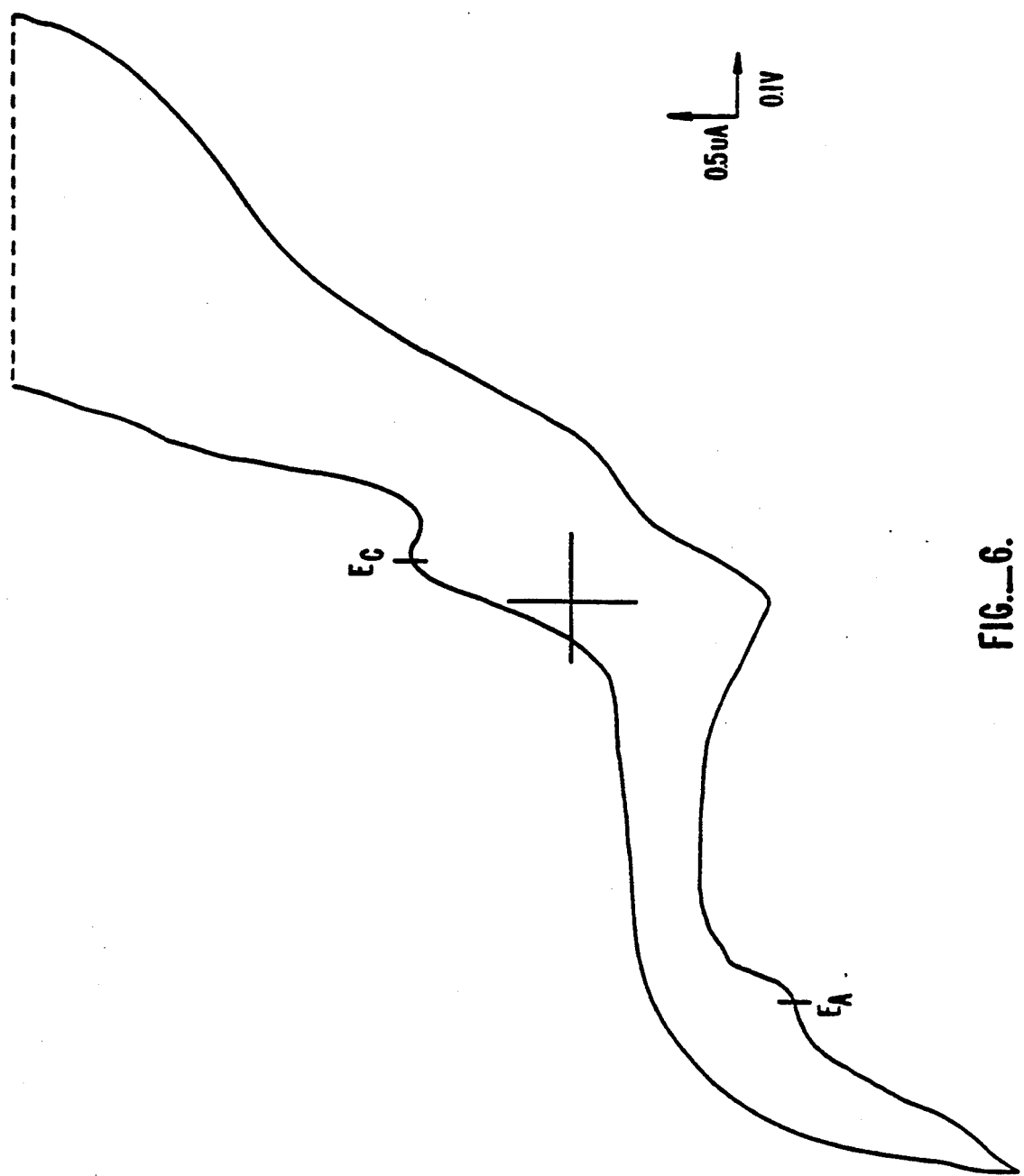
FIG._6.

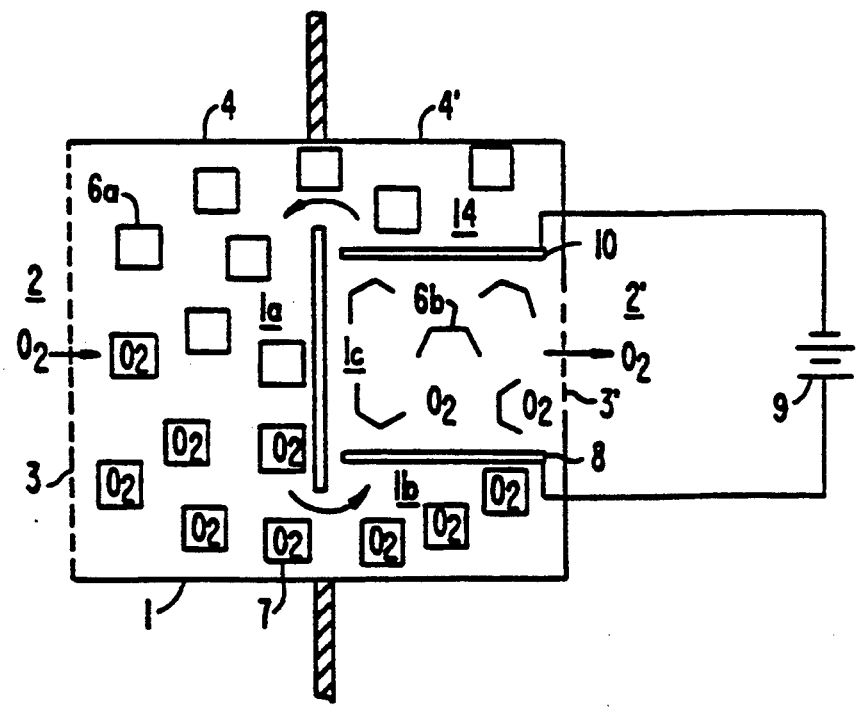
FIG._7.
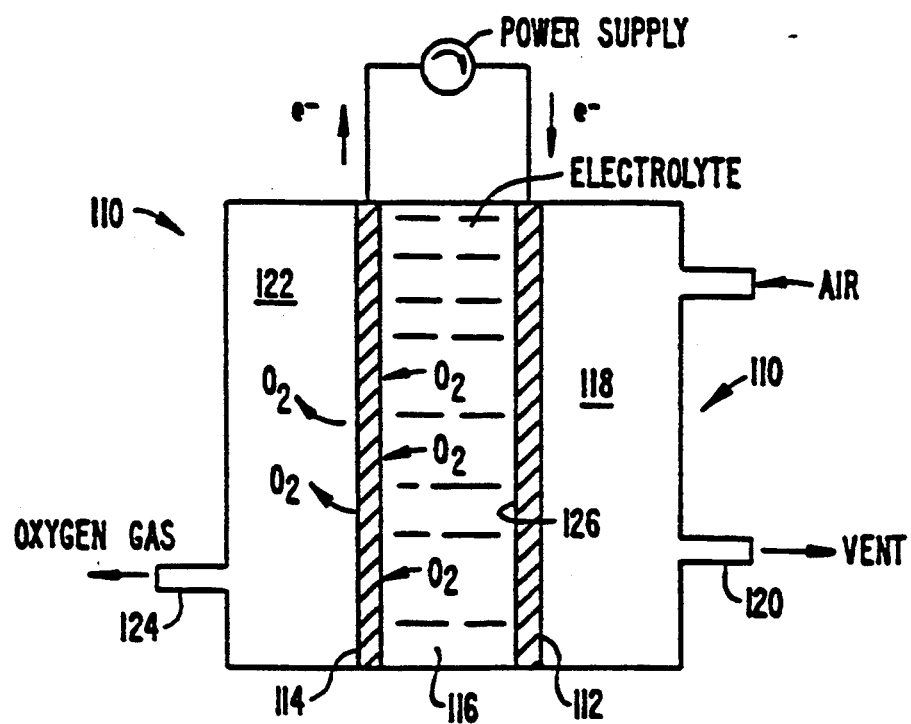
FIG._10.

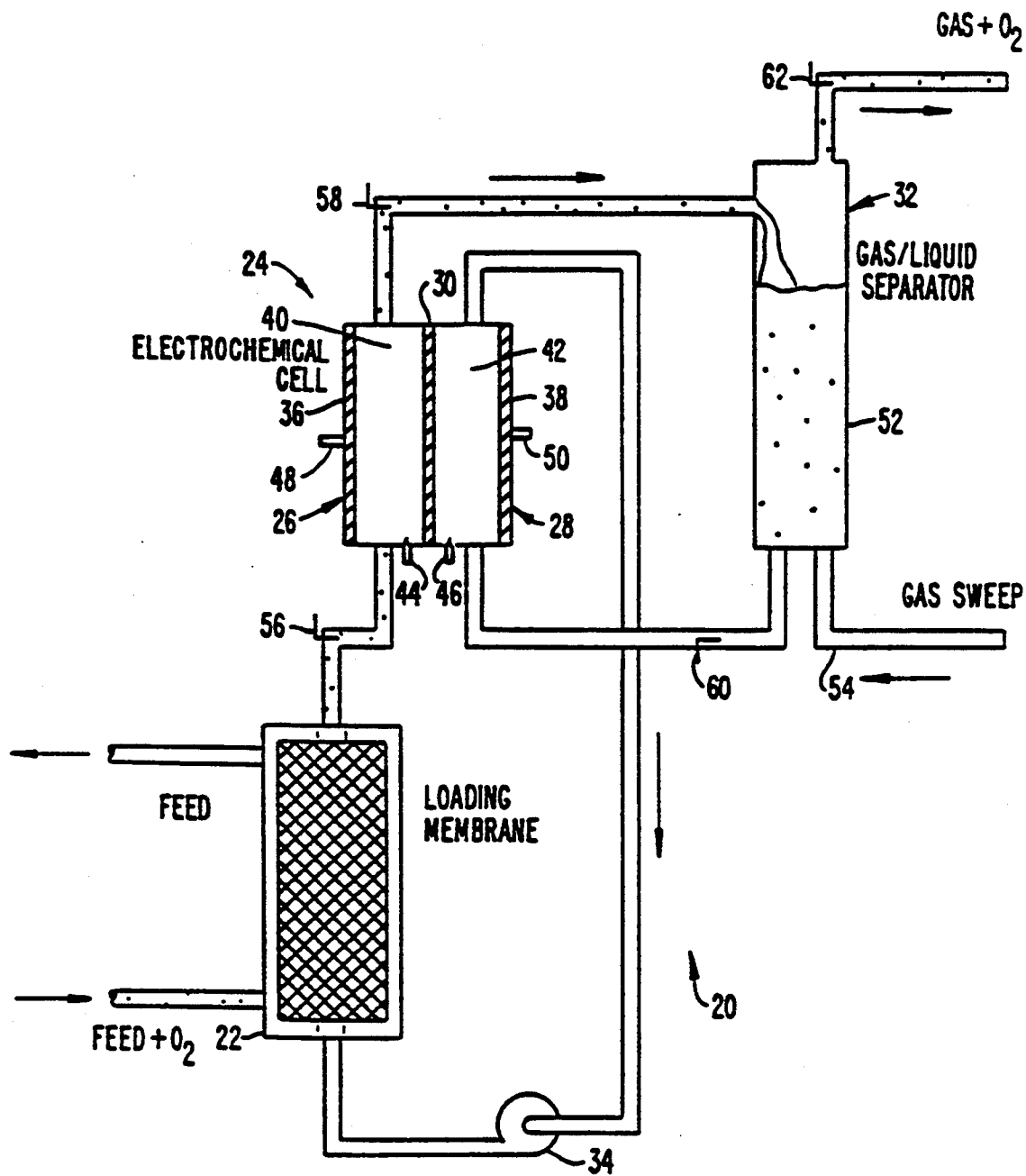
FIG._8.

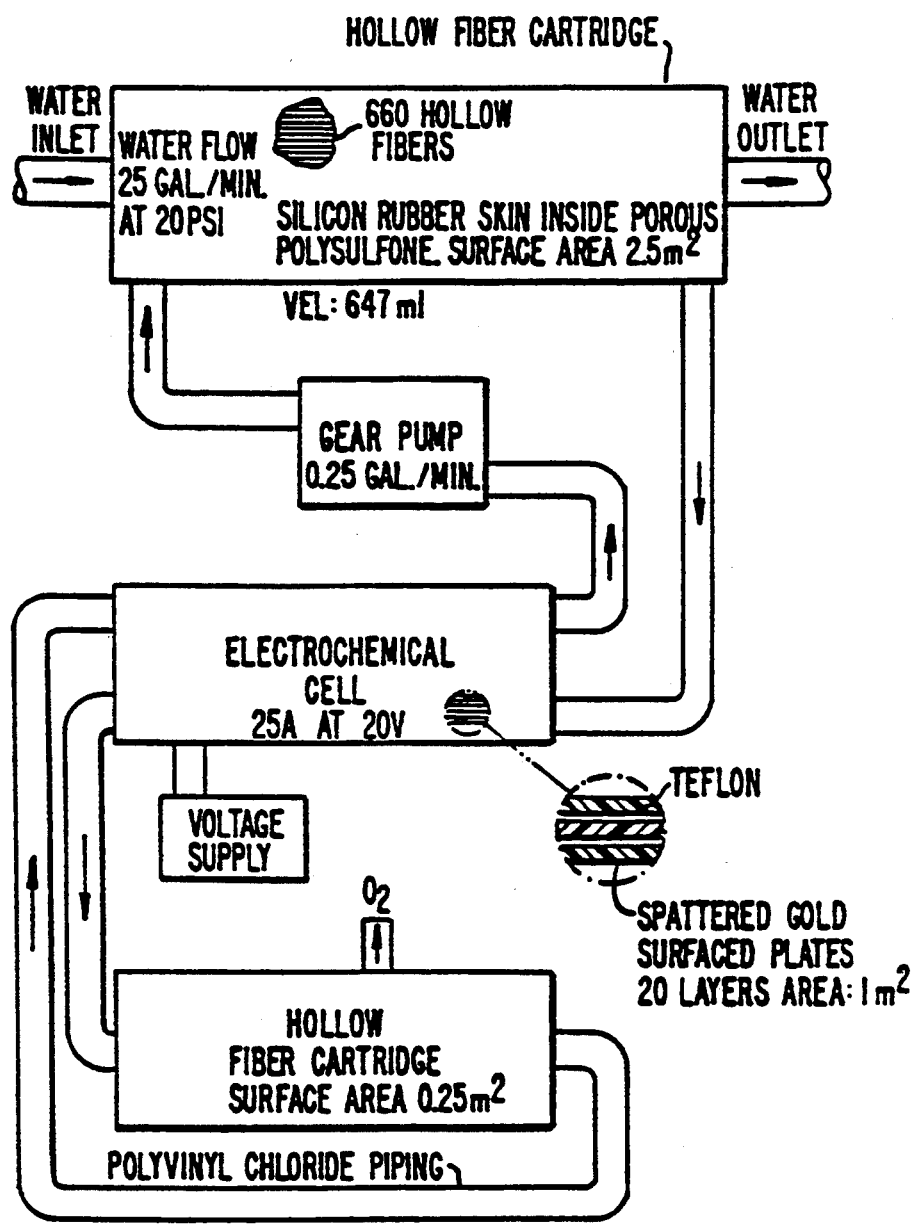
FIG._9.

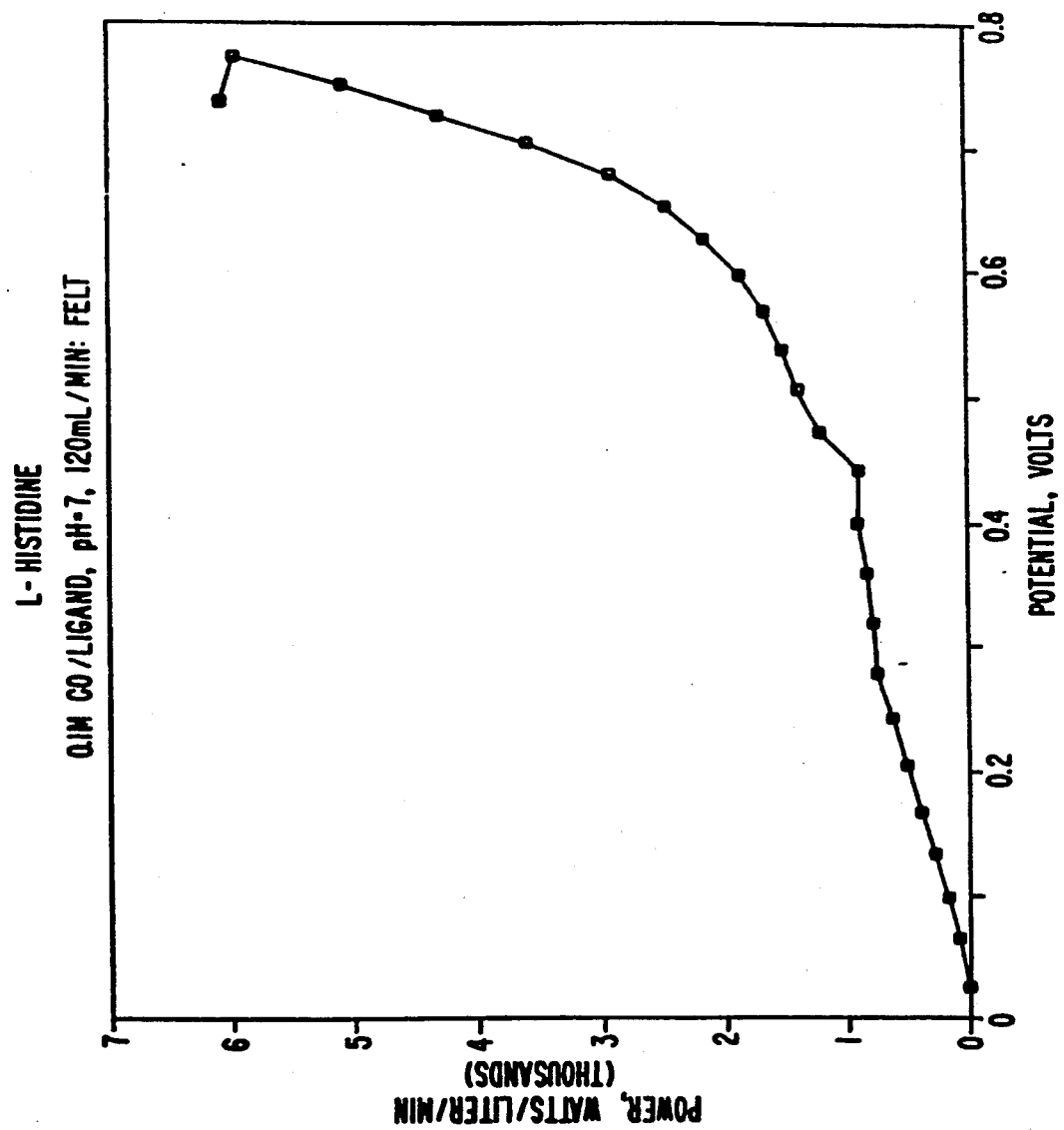
FIG._11.

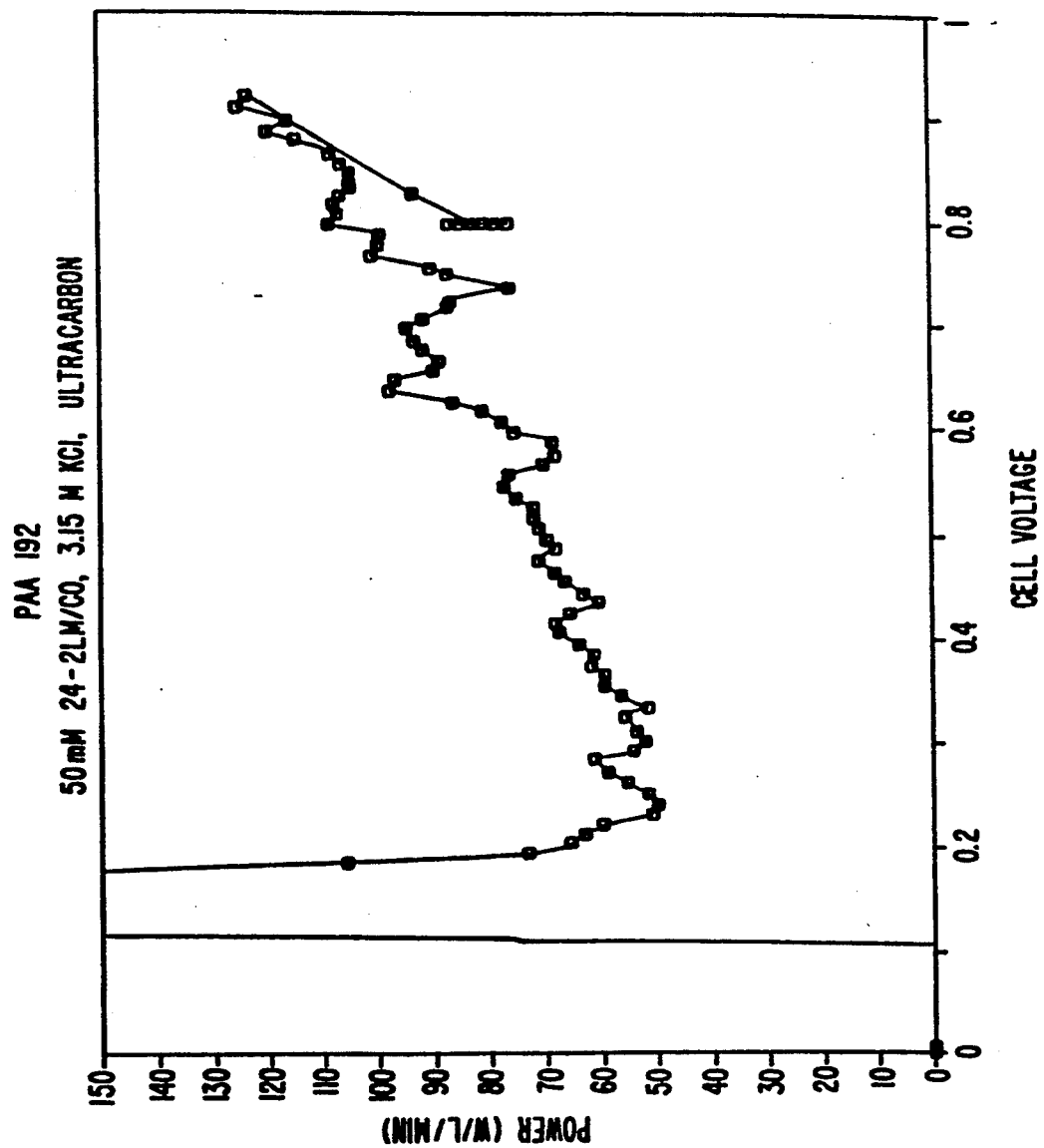
FIG._12.

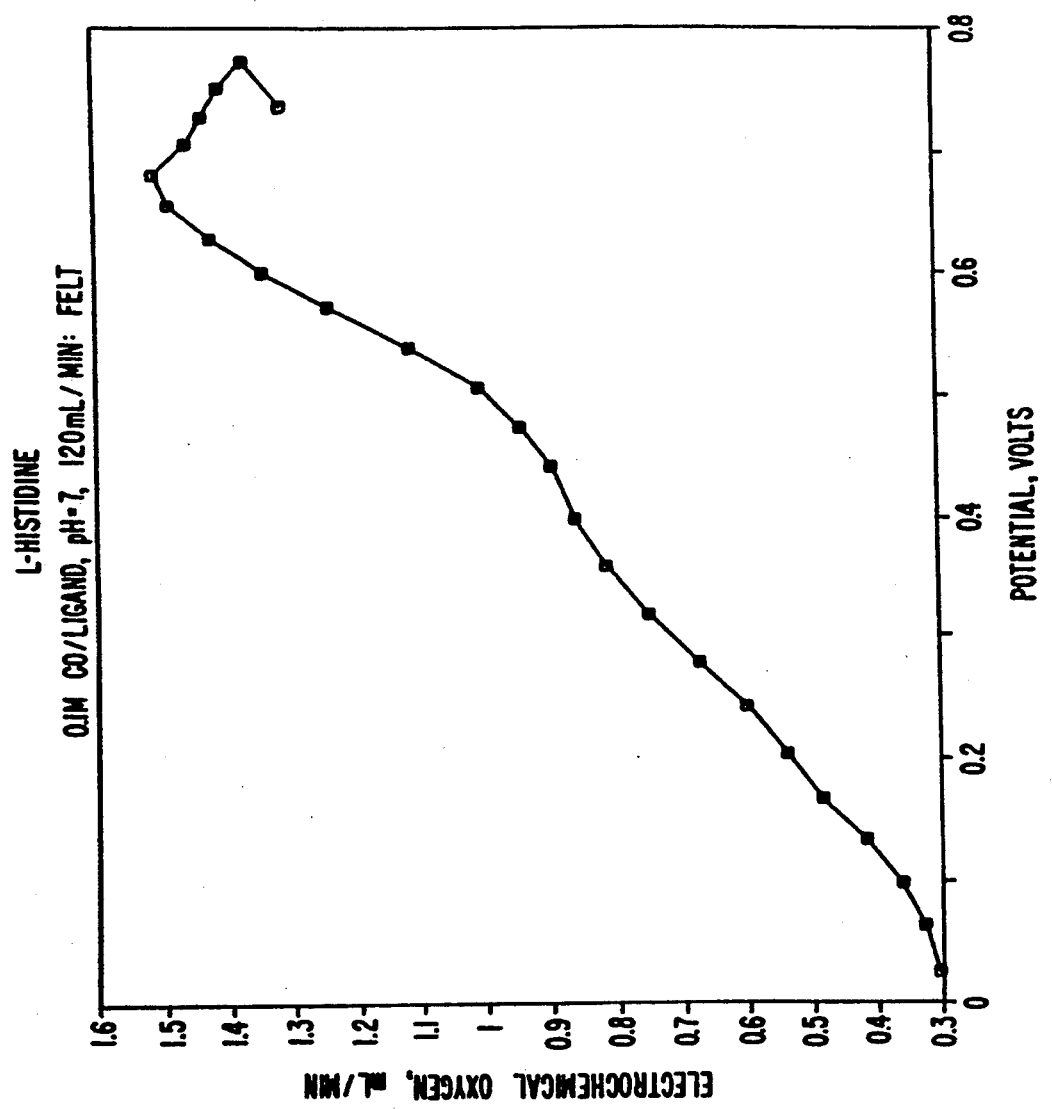
FIG._13.

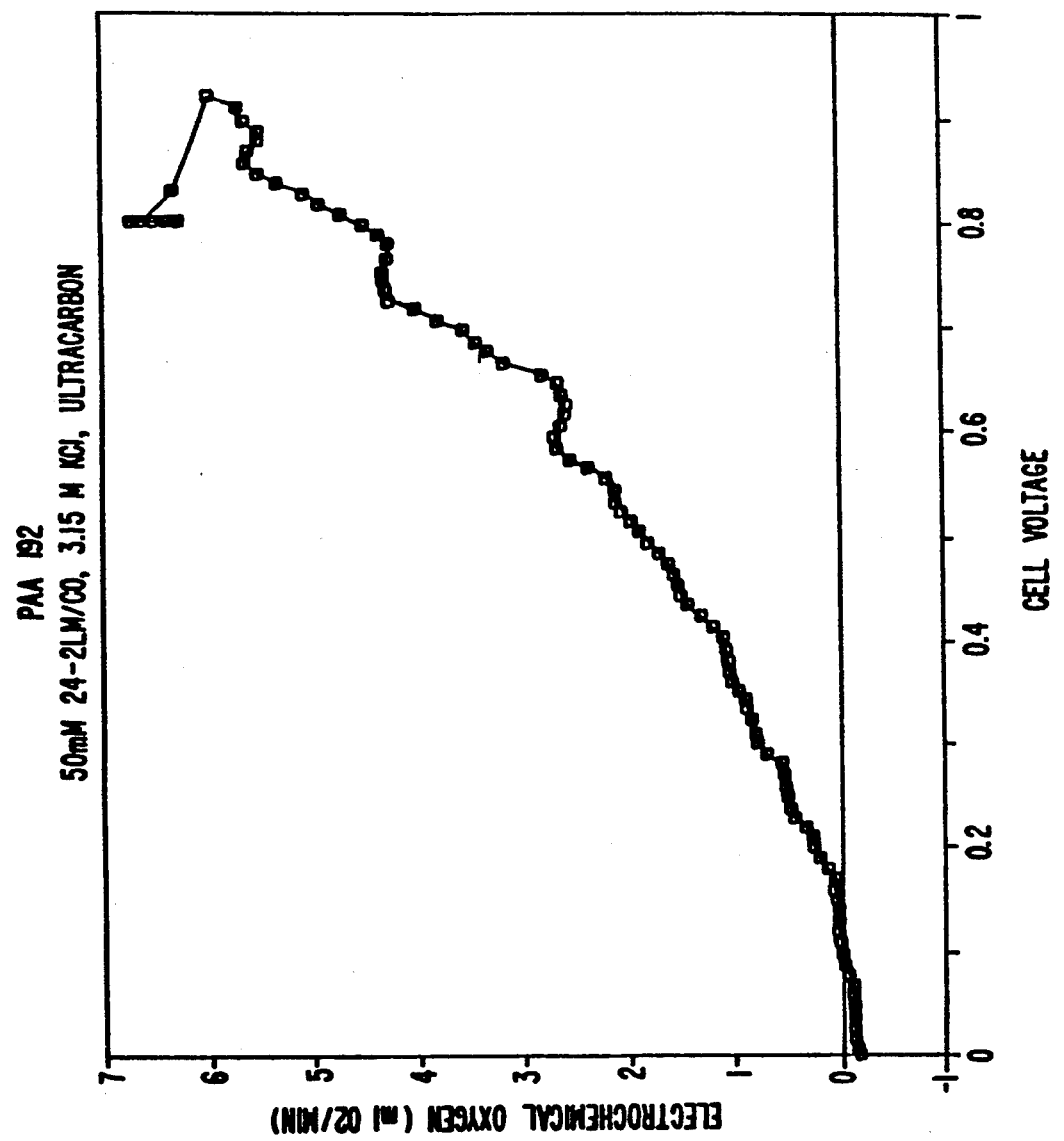
FIG._14.

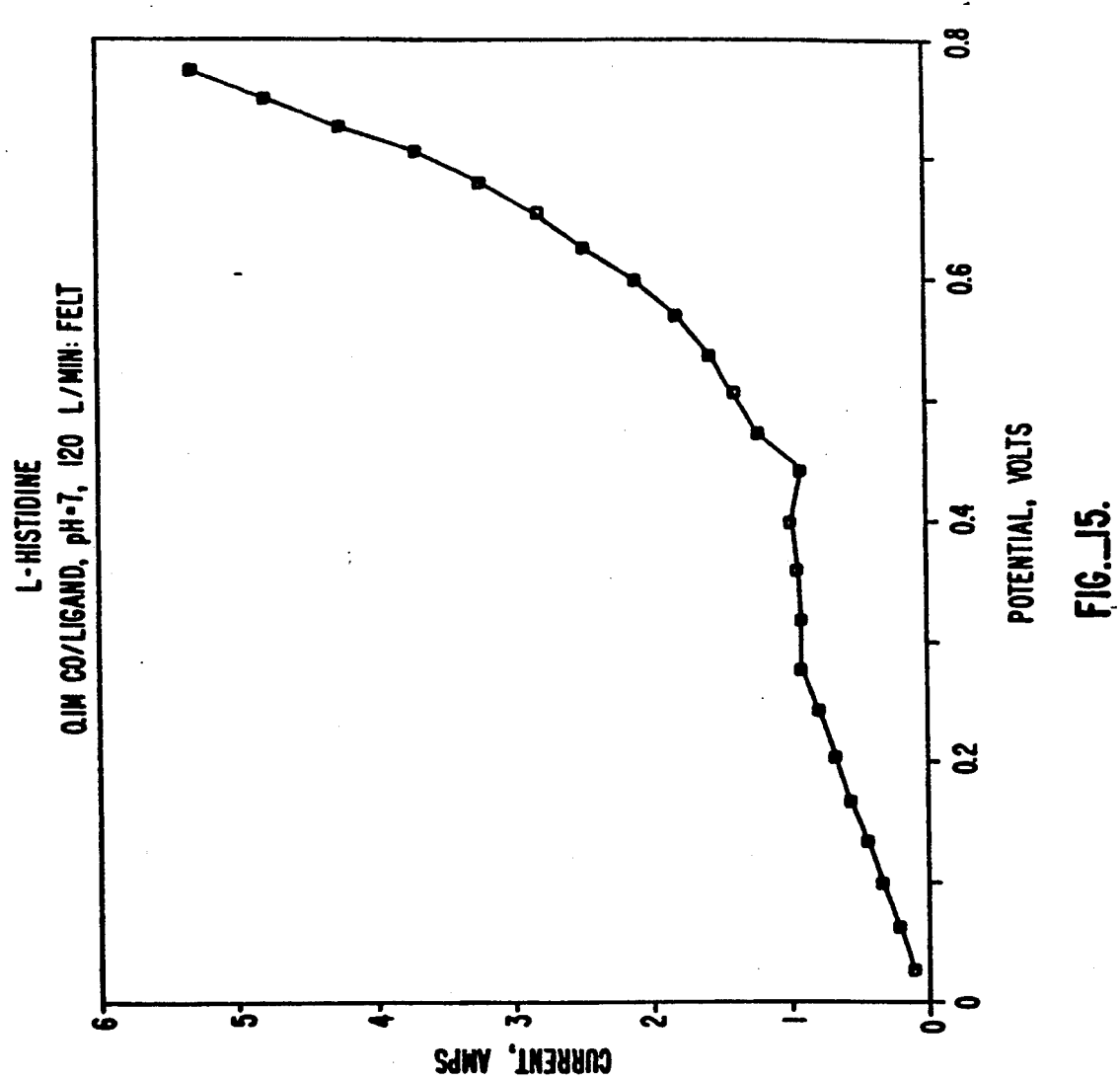
FIG._15.

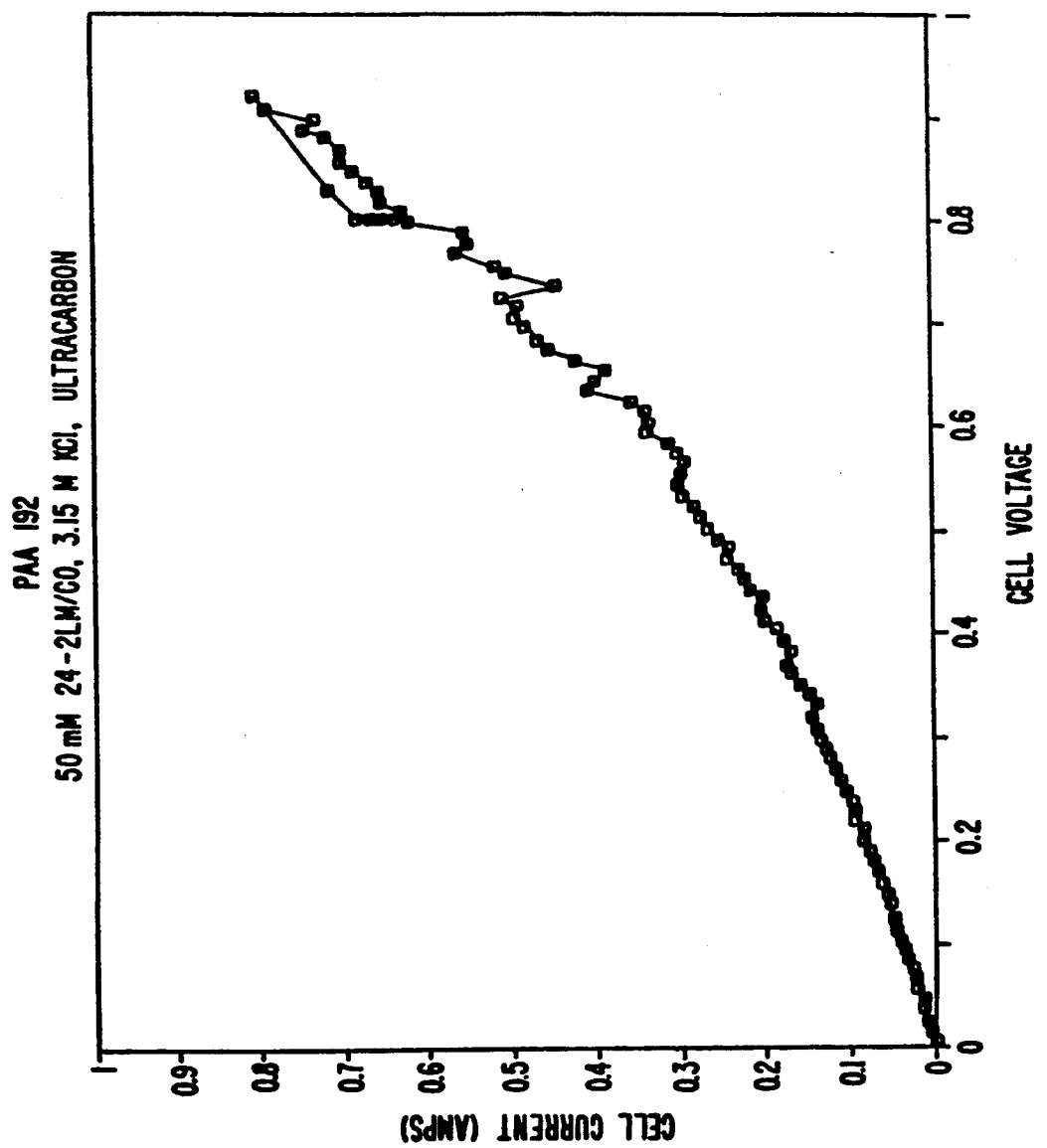
FIG._16.

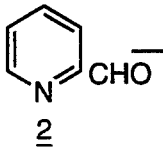
FIG._17
TABLE 1A

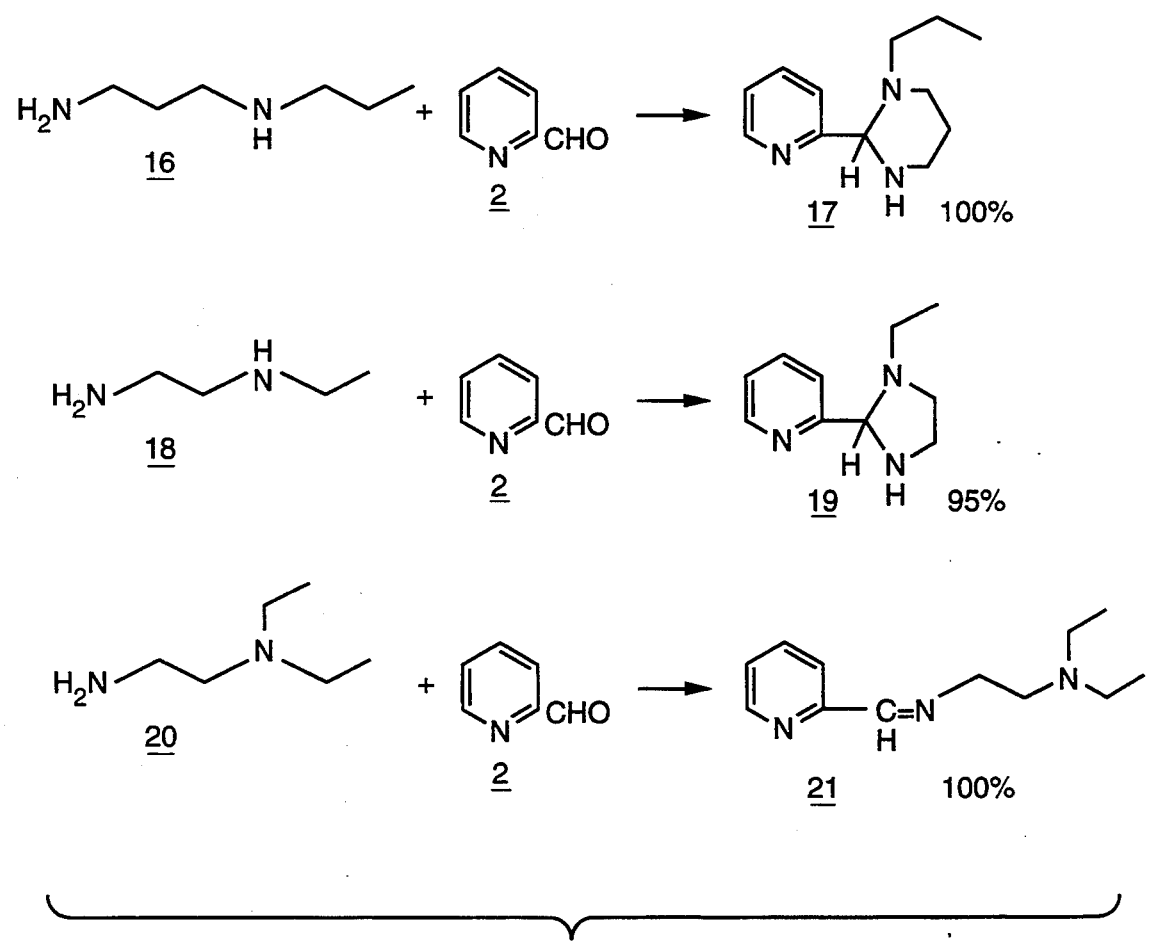
FIG._18

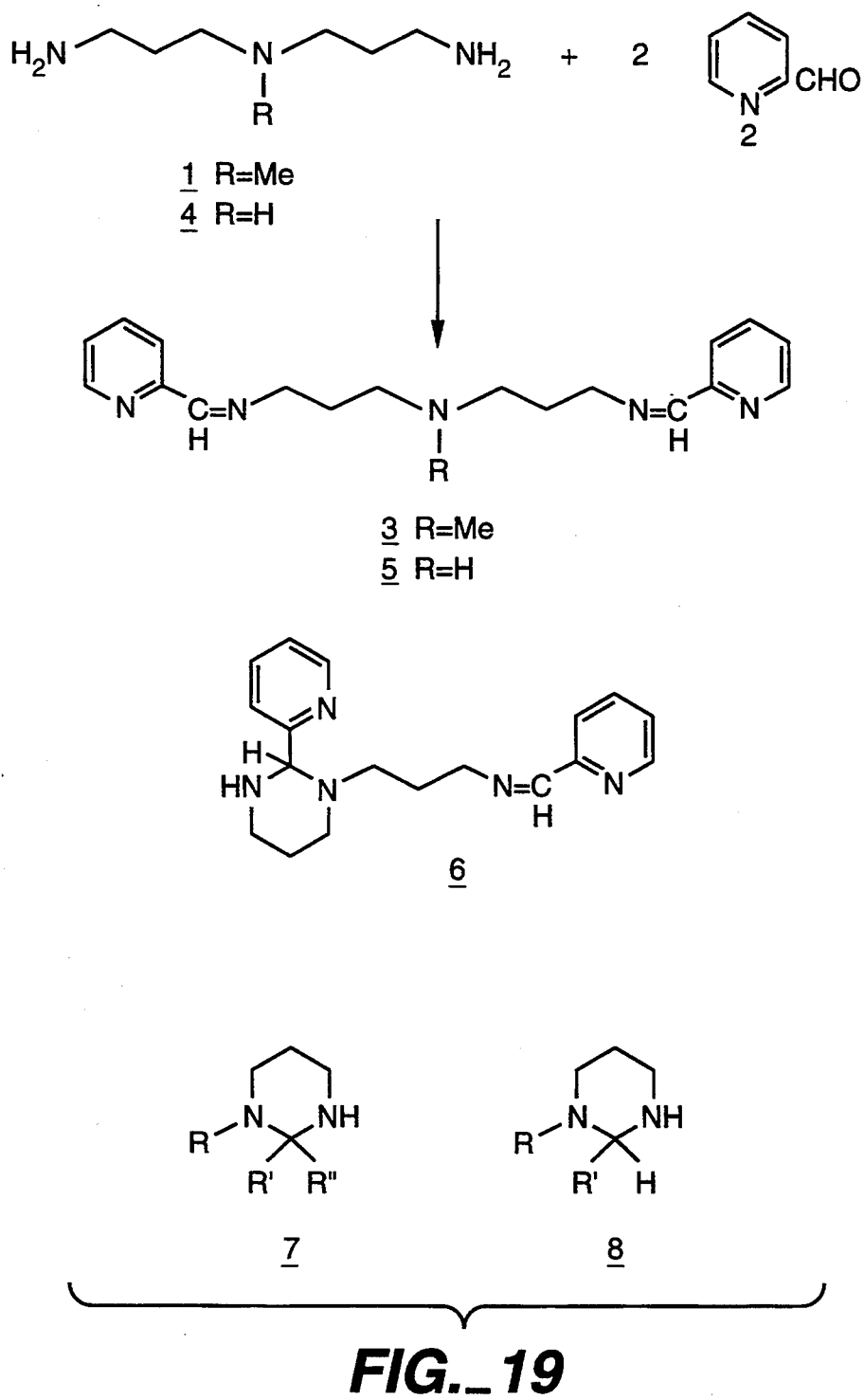
FIG._19

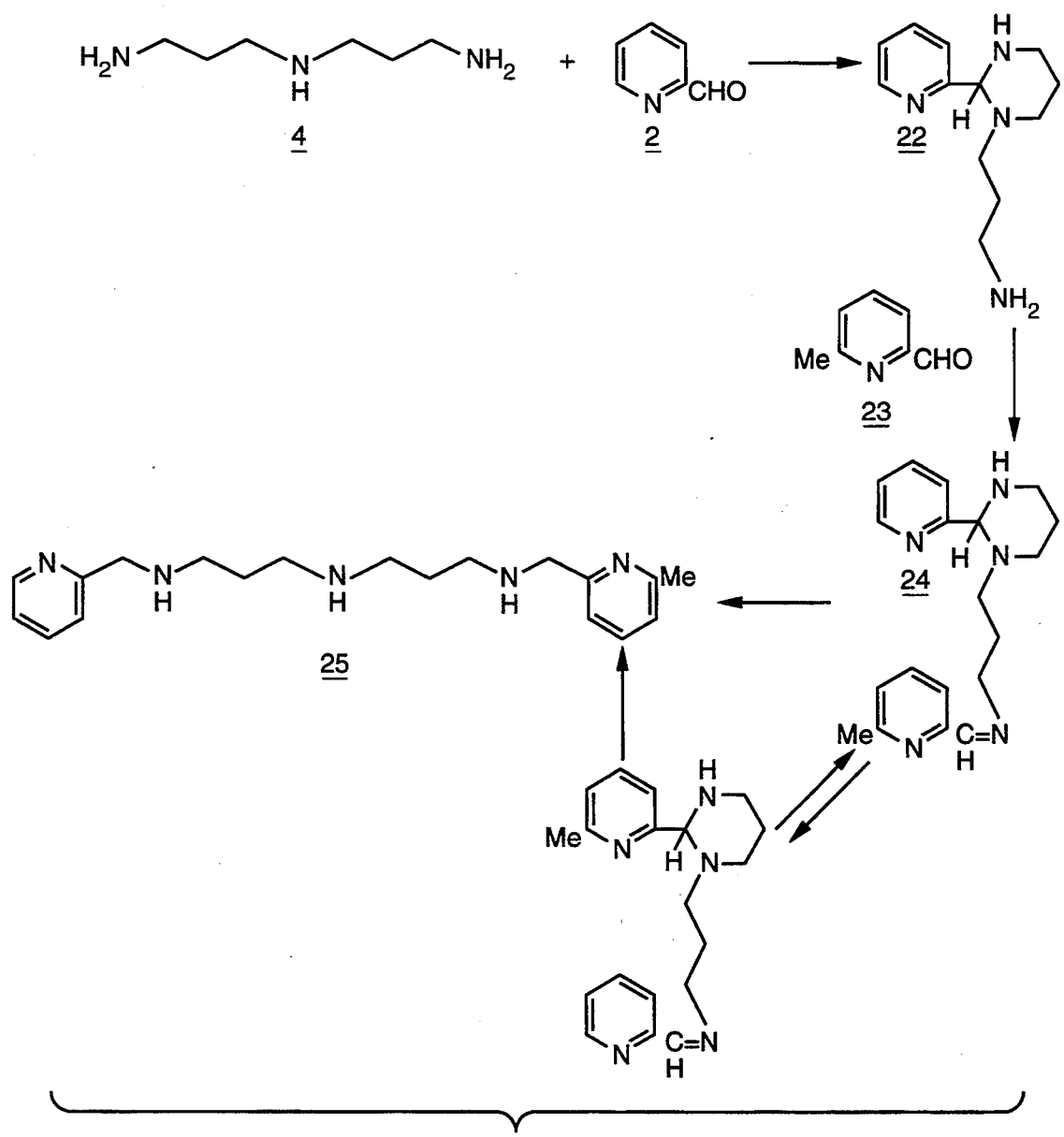
FIG._20

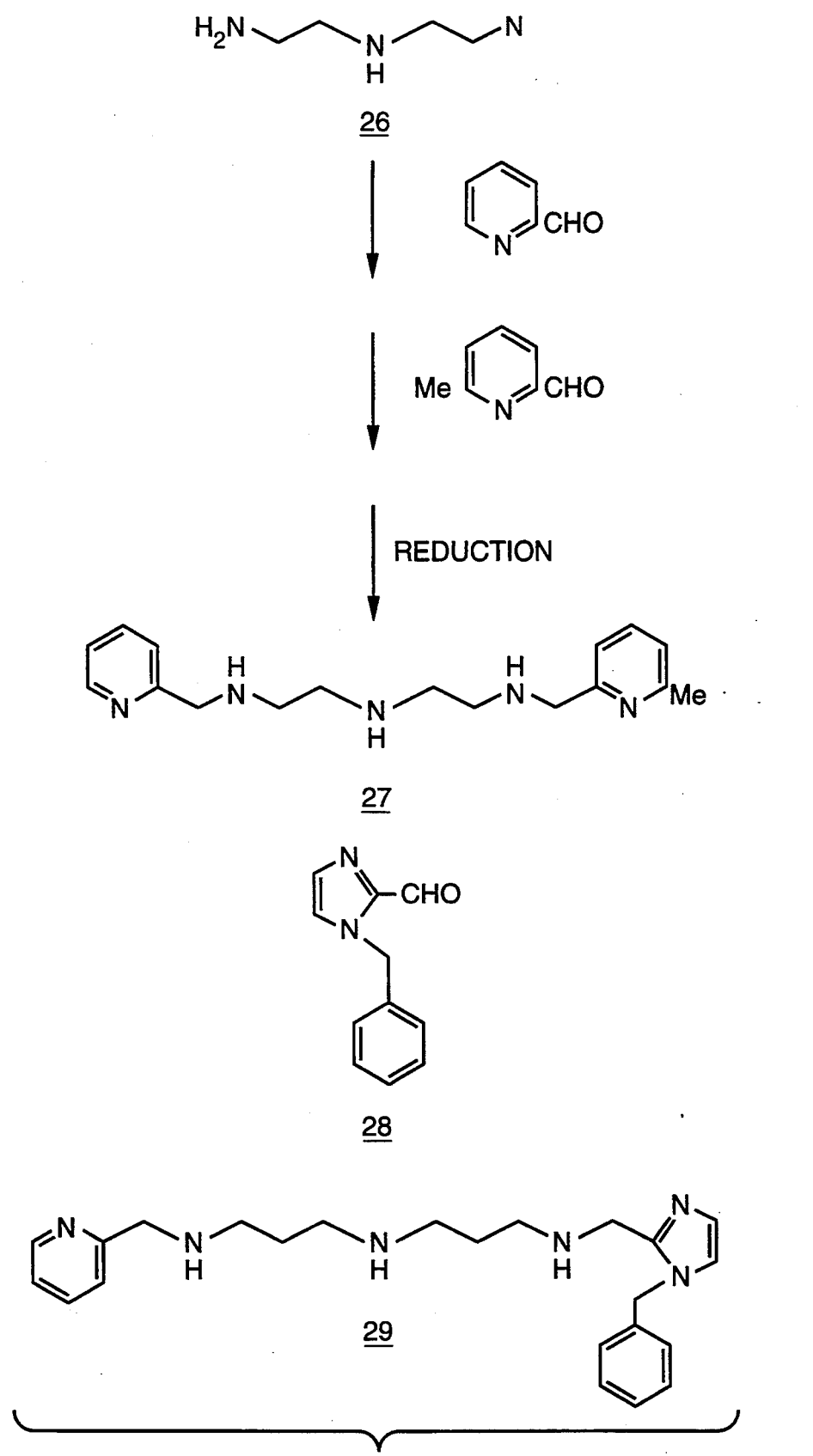
FIG._21

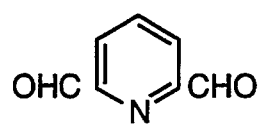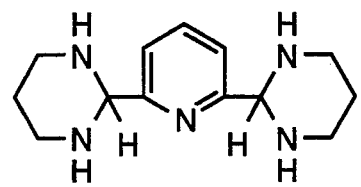
30    31
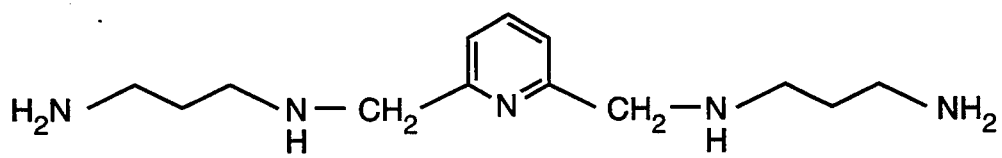
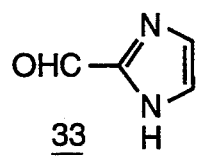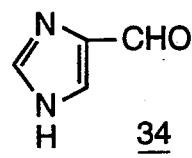
33    34
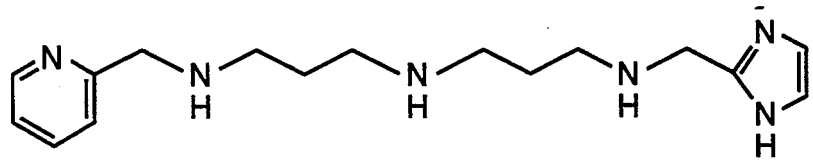
35
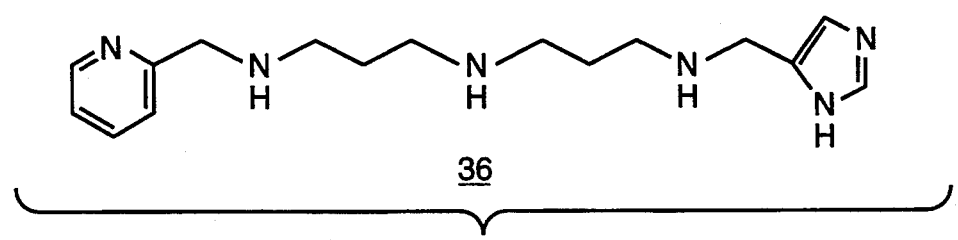
36
FIG._22

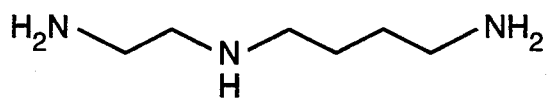
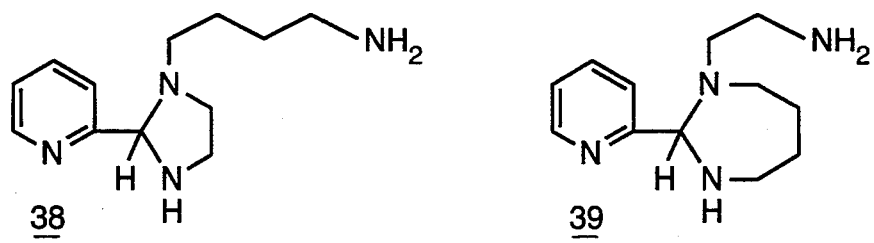
FIG._23
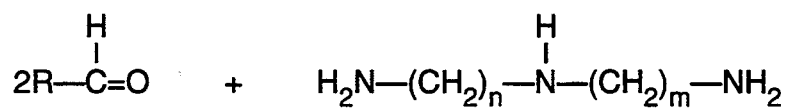
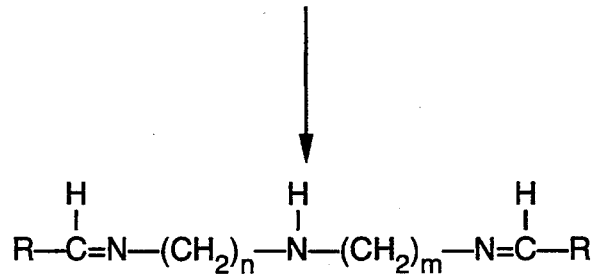
n,m=2,3, or 4
SCHEME 1
FIG._24

SCHEME 2

SYMMETRICAL AND UNSYMMETRICAL POLYALKYLAMINE METAL COMPLEXES FOR LIGAND EXTRACTION AND GENERATION

RELATED APPLICATIONS

This is a continuation-in-part of U.S. Ser. No. 558,516, filed Jul. 31, 1990, now abandoned, which is a divisional of U.S. Ser. No. 306,730, filed Feb. 3, 1989, now U.S. Pat. No. 4,959,135, which is a continuation-in-part of Ser. No. 018,891, filed on Feb. 25, 1987, now abandoned. U.S. Ser. No. 306,730 is incorporated herein by reference in its entirety.

BACKGROUND OF THE INVENTION

1. Field of the Invention

This invention relates to carrier complexes for use in apparatus and methods for extracting molecular oxygen from a fluid; more particularly, the invention relates to electrochemically active polyamine (also referred to as polyalkylamine) complexes of transition metals that reversibly bind small ligands such as molecular oxygen and the use of such complexes for extraction of ligands from a first fluid environment and release of ligands to a second fluid environment.

2. Relevant Art

Molecular oxygen is used in many industrial, scientific, medical, and recreational applications.

A wide variety of methods for extracting oxygen from air, sea water, and other fluids are known. On a large scale, oxygen is generally prepared by fractional distillation of liquid air. Typically, filtered air is passed through an alkali absorbent in order to remove moisture and carbon dioxide. The air is then compressed, and the heat of compression is removed by ordinary cooling procedures. The cooled compressed air is allowed to expand which causes it to cool further. The expanded air is then recompressed, cooled, and reexpanded repeatedly to liquify the air. Liquid air is then fractionally distilled to remove nitrogen and other impurity gases. The remaining liquid oxygen may be stored in that form or as compressed gaseous oxygen. Cryogenic methods of oxygen production typically entail large installations which are not portable and are energy intensive. The production and storage of oxygen present severe explosion and fire hazards. While cryogenic fractional distillation processes have proved useful for supplying oxygen to large industrial users, such as the steel industry and sewage treatment plants, there are many applications in which local production of oxygen in relatively smaller quantities is both useful and desirable.

Numerous methods and devices for separating oxygen from fluids such as air and sea water have been devised. Many utilize gas permeable membranes to separate oxygen from the particular fluid feedstock by diffusion. For example, Bodell, U.S. Pat. No. 3,333,583, and Robb, U.S. Pat. Nos. 3,369,343 and 3,510,387, disclose apparatus for extracting oxygen from sea water using thin tubes of silicon rubber or a membrane of silicone rubber, respectively. Isomura, U.S. Pat. No. 3,377,777, discloses concentrating oxygen from natural waters by equilibration with exhaled gases, i.e., by utilizing large areas of gas water interface and simple diffusional considerations for transport of oxygen from the liquid phase across the permeable membrane to a gas phase. Systems based on simple diffusion processes are also taught by: Blanchard, et al., U.S. Pat. No. 3,651,616, Blackmer, et al., U.S. Pat. No. 3,976,451; Hedman, U.S. Pat. No. 3,979,190; and Shindo, et al., U.S. Pat. No. 4,268,279. Such systems have proven impractical for use due to a variety of factors including: the lack of selectivity of the membranes for oxygen, the size or weight of the system required to produce useful quantities of oxygen, and the limitation that the maximum partial pressure of oxygen which can be extracted without additional vacuum or compression pumps is approximately equivalent to that of the fluid feed stock.

The permeation rates and selectivity of such membranes can be increased by coating the delivery side of the membrane with a gas-solubilizing substance (Allington, U.S. Pat. No. 3,751,879) or by incorporating transition metal-based carrier complexes in the membrane (e.g., Nishide, et al., Macromolecules 19,494–496 (1986)). Other examples of facilitation of the rate or enhancement of the selectivity of diffusion extraction by incorporation of absorbing materials in polymeric membranes are given by Ward, et al., U.S. Pat. No. 3,396,510. While the use of such membranes would be an improvement in oxygen extraction devices, the partial pressure of oxygen that may be delivered remains limited by the effective partial pressure of oxygen in the feed stock fluid.

A second type of oxygen source that is portable and can supply oxygen in small amounts as needed is disclosed by Rind, U.S. Pat. No. 4,020,833. This system includes a mixture of a metallic superoxide, decomposable to release oxygen upon contact with carbon dioxide and water vapor, and a material which absorbs $CO_2$. The utility of this system is limited in that the capacity of oxygen which can be produced is limited by the bulk of material which can be carried. In addition, the supply of chemical reactants must be continuously replenished for continued use of oxygen.

A variety of electrochemical methods of producing oxygen from water have been developed. The most basic of these methods is the electrolysis of water into component hydrogen and oxygen gases. Where oxygen is the product of primary interest, electrolysis techniques usually suffer form the significant disadvantage of cogenerating hydrogen. The oxygen produced is typically contaminated with small quantities of hydrogen. In addition, the hydrogen produced presents a severe fire or explosion hazard which makes such systems generally unsuitable for use in closed environments and nearby people. Electrolysis of water to produce oxygen is extremely energy intensive. Some of these disadvantages have been ameliorated by the apparatus disclosed by Nolan, U.S. Pat. No. 4,488,951, in which the hydrogen produced from an electrolysis cell is electrochemically reacted with oxygen from air to form water and hydrogen peroxide; the hydrogen peroxide produced is then decomposed to form water and oxygen. However, the power requirements of such a cell remain quite large.

Other electrochemical methods of oxygen production utilize a variety of two- and four-electron redox processes to extract oxygen from air. Tseung, et al., U.S. Pat. No. 4,416,758, describes a cell in which oxygen from air is reduced in solution at a graphite electrode to form peroxyl and hydroxyl ions. The peroxyl ions so produced diffuse through an ion-permeable membrane and are catalytically reacted to form oxygen in a second cell compartment with a $NiCo_2O_4$ or $CoFe_2O_4$ catalysts. This cell, which requires an operating voltage of about one volt, uses a concentrated alkaline electrolyte at elevated temperatures and consumes substantial electrical energy. Chillier-Duchetel, et al., U.S. Pat. No. 4,061,445, also regenerates oxygen from peroxyl ions. The cell uses bipolar electrodes coated with anthraquinone derivatives; these anthraquinones are electro-chemically reduced and, in turn, reduce the oxygen to the desired peroxyl ions. The peroxyl ions are reacted at the anode to regenerate oxygen gas. Blanchard, et al., U.S. Pat. No. 4,137,371, discloses a zinc oxide cell which extracts oxygen from the air by diffusion. Gagne, et al., U.S. Pat. No. 4,475,994, discloses an electrochemical cell in which oxygen from the air is reduced to superoxide ions ($O_2^-$) on a quinoline-coated electrode. The superoxide anions are transported to the anode using transition metal carrier compounds. At the anode, the superoxide is reoxidized to oxygen. Tomter, U.S. Pat. No. 3,410,783, discloses electrolytic reduction of air-borne oxygen at one reduced oxygen species are pumped or diffuse, respectively, between the two electrodes.

It has long been known that the variety of naturally occurring metalloproteins, including hemoglobin, myoglobin, hemocyanin, and hemerythrin, are capable of reversibly binding oxygen and transporting oxygen from a permeable membrane to a site within an organism at which the oxygen is needed. In hemoglobin, for example, oxygen is reversibly bound to ferrous (Fe(II)) prophyrins incorporated in the protein. Oxidized, ferric hemoglobins are unreactive to molecular oxygen. The properties of hemoglobins, hemerythrins, and hemocyanins have been the subjects of numerous studies, as documented in, e.g., Bonaventura, et al, Symposium on Respiratory Pigments, J. Am. Zool. 20, 7 (1980) and 20, 131 (1980).

The oxygen binding properties of such proteins have been utilized to extract oxygen from air and other fluids. Miller, U.S. Pat. No. 3,230,045, discloses the use of an oxygen-binding chromoprotein such as hemoglobin to separate oxygen from other gases. The chromoproteins are kept moist or in solution and are absorbed on or bound to filter paper; and electrolyte such as sodium chloride may also be present. The filter paper is alternately exposed to air (the carrier absorbs oxygen) and vacuum, which removes the bound oxygen.

Bonaventura, et al., U.S. Pat. Nos. 4,427,416 and 4,343,715, also disclose the use of naturally occurring oxygen carriers to extract oxygen from fluids. The metalloproteins are insolubilized at high concentrations by entrapment and/or covalent linkage to a polyurethane matrix or similar, flexible support in states that are capable of reversibly binding oxygen. The material disclosed in these patents, generally known as "hemosponge" since it usually incorporates hemoglobin or another heme-type protein, is capable of extracting oxygen from various fluid environments. However, the rate of extraction is less than that which may be desired for many applications which involve a high rate of oxygen use. Further, these disclosures utilize chemical regeneration of the oxidized carrier compound, with, e.g., ferricyanide solutions, which, in applications which require large amounts of oxygen, present considerable supply and waste disposal problems. Release of bound oxygen from the "hemosponges" requires either chemical oxidation of the carrier compound, with the concomitant supply and waste disposal problems, or various methods for pressing the hemosponge, which require pumps, vacuums, and the like which use substantial quantities of energy.

A variety of transition metal complexes with mono-, bi-, and multi-dentate ligands are also capable of reversibly binding oxygen. Several devices and methods utilizing such synthetic transition metal oxygen-carrier compounds have been devised for extraction of oxygen from air. For example, Warne, et al., U.S. Pat. No. 2,217,850, discloses the reaction of oxygen in air with solids of cobaltous hexamine salts to synthesize, on a large scale, peroxocobalt amine solids, followed by removal of the solution, and separate chemical regeneration of the oxygen and the starting cobalt hexamine salts. Fogler, et al., U.S. Pat. No. 2,450,276, utilizes a solid cobaltous compound of a tetradentate Schiff base ligand to extract oxygen from air by alternately cooling a bed of the solid carrier compound, which absorbs oxygen from the air, and heating the oxygenated carrier compound to release bound oxygen. This process is accompanied by severe decomposition of the carrier compound. Iles, et al., U.S. Pat. No. 4,165,972, discloses an apparatus for alternately heating and cooling alternate beds of carrier compound to absorb oxygen from air into cooled beds of carrier and expel oxygen into a second gas handling system by heating the bed of carrier compound.

Solutions of transition metal carrier compounds have been used in both electrochemical and nonelectrochemical methods of extracting oxygen from air. For example, Gagne, U.S. Pat. No. 4,475,994, discussed above, utilizes cobaltous compounds to transport electrochemically-generated superoxide anions from the cell cathode to the anode where the oxygen is regenerated.

Roman, U.S. Pat. No. 4,542,010, discloses a method for producing oxygen and nitrogen using a porous, hydrophilic membrane support containing a solution of a transition metal oxygen carrier in a non-aqueous solvent. This device serves as a facilitated diffusion membrane; oxygen bound to the carrier diffuses from a first permeable membrane containing air to a second membrane where the oxygen is released form the carrier. Thus, the permeability of oxygen through the membrane is increased by the reversible binding of oxygen to the organometallic carrier compound. Loading and unloading of oxygen from the liquid membrane is accomplished by a combination of temperature and/or pressure differentials. One drawback to this process is that oxygen generated using this device is costly, since the temperature and/or pressure differentials required to load and unload the oxygen carriers require large energy inputs. In addition, both sides of the membranes must remain saturated with solvent in order for the membrane to function, significantly adding to the cost and complexity of the device.

It is now well understood that many such transition metal-based carriers typically have a lower valence state, i.e., Mn(II), Fe(II), Co(II) or Cu(I), in which the carrier is capable of reversibly binding molecular oxygen under appropriate conditions, and a higher valence (more oxidized) state, e.g., Mn(III), Fe(III), Co(III), or Cu(II), in which binding of molecular oxygen is essentially absent. Most of the known methods for extracting oxygen from air using such transition metal carrier compounds are dependant upon the carrier compound remaining in the lower valence state. Molecular oxygen is absorbed from sources with a relatively high concentration (and hence chemical activity) of oxygen and reversibly bound to the carrier compound. The oxygen desorbs when the carrier compound is exposed to an environment in which the chemical activity of oxygen is lower, e.g., low oxygen partial pressures or elevated temperatures. Extraction processes may be carried out by exposing the carrier compounds to alternating environments of higher and lower oxygen activity, e.g., alternating partial pressure of oxygen or alternating low and high temperatures. The carrier compound may actually be used to carry oxygen from the feedstock environment to the delivery environment by diffusion or by pumped circulation.

After prolonged use, as with repeated heating and cooling cycles in bed reactors or oxygenated solutions, the carrier compounds tend to oxidize and become inactive toward oxygen. In solution, this oxidation and degradation often occurs via the formation of the stable and unreactive $\mu$ oxo dimer of, e.g., iron prophyrins. E.g., Leal, et al., J.Am. Chemc. Soc. 97, 5125 (1975). Similarly, many cobalt-based carrier compounds tend to oxidize spontaneously to forms which are unreactive to oxygen. Various solutions to the problem of carrier compound decomposition have been suggested, although generally not with a view to oxygen extraction. For example, in attempts to protect the transition metal from its environment but allow diffusion of oxygen to the metal, various bulky ligands have been used. All alternate approach, suggested by Leal, et al., supra, is to immobilize the carrier compound of a solid support. Another approach to avoiding many of these difficulties is the regeneration of the lower valence state thorough the use of chemical and/or electrochemical reduction. Chemical regeneration methods may succeed, but, for the large scale production of oxygen from air, require large quantities of regenerating chemicals and typically produce commensurate quantities of waste chemicals.

Bonaventura, et al., U.S. Pat. Nos. 4,602,987, 4,609,383, and 4,629,544, disclose another apparatus and methodology for extraction of oxygen from gas or liquid streams and delivery of the oxygen in high purity, in which the binding oxygen to the transition metal carrier is modulated electrochemically. These patents disclose circulating a fluid containing dissolved organo-metallic carrier compounds to a region in which the carrier complex, in its lower valence state, is contacted with oxygen diffusing through a permeable membrane. The fluid, with oxygen bound to the carrier, is pumped to the electrode compartment in which the carrier is oxidized to its higher valence state, forcing the release of the bound oxygen. The carrier is then circulated to a second electrode compartment in which the carrier is reduced to its lower state, forcing the release of the bound oxygen. The carrier is then circulated to a second electrode compartment in which the carrier is reduced to its lower state in which it can again bind oxygen. Since the oxygen capacity of the fluid is enhanced by the solubility of the organometallic carrier compound, high partial pressures of oxygen may be obtained and oxygen may be "pumped" to concentrations or pressures greater than those of the feedstock fluid. The pressures of oxygen which may be produced are thus greater than the concentrations obtainable by simple diffusion through membranes or facilitated diffusion without electrochemical unloading of the carrier compounds.

Artificial transition metal oxygen carriers which are potentially usable in oxygen extraction systems have been described by a number of researchers. For example, Brault, et al., Biochemistry 13, 4591 (1974), discloses the preparation and properties of ferrous deutero- and tetraphenyl-porphyrins in various organic solvents. Castro, Bioinorganic Chemistry 4, 45–65 (1974), discloses the synthesis of hexa- and penta-coordinate iron porphyrins, which are models for the prosthetic groups of active sites of certain cytochromes and other heme proteins. Other iron-containing transition metal compounds which may reversibly bind oxygen are described by Chang, et al., J. am. Chem. Soc. 95, 5810 (1973).

Numerous cobalt, manganese, and copper compounds also exhibit reversible oxygen binding. For example, Crumbliss, et al., Science 164, 1168–1170 (1969), discloses Schiff base complexes of Co(II) which form stable complexes with oxygen species in solution. See also: Crumbliss, J. Am. Chem. Soc. 92, 55 (1970) (monomeric cobalt complexes of oxygen); Dufour, et al., J. Mol. Catalysis 7, 277 (1980) (catalysis of oxidation of simple alkyl-substituted indoles by Co(II), Co(III), and Mn(III) meso-tetraphenyl porphyrins via a ternary porphyrin-indole-oxygen complex); Traylor, et al., J. Am. Chem. Soc. 96, 5597 (1974) (effect of solvent polarity on reversible oxygenation of several heme complexes prepared by reduction with sodium dithionite or a mixture of palladium black and calcium hydride); Held, U.S. Pat. No. 4,442,297 (absorption of gases using manganese compounds); Simmons, et al., J. Chem. Soc. Dalton Trans. 18–37 (1980) (reversible coordination of oxygen to copper (I) complexes of imidazole derivatives).

Some types of such transition metal carrier complexes have been used in or suggested for use in devices for extraction, absorption, and generation of oxygen from fluid media. For example, Roman, U.S. Pat. Nos. 4,451,270 and 4,542,010, discloses Schiff base complexes of metals in an oxygen-selective, permeable membrane and extraction system. The carriers include cobalt complexes of linear and macrocyclic tetradentate, linear pentadentate, and bidentate Schiff base ligands in primarily non-aqueous, Lewis base solvents. Hill, U.S. Pat. No. 4,442,297, uses phosphine complexes of Mn(II) in dehydrated solvents to purify nitrogen gas by extracting impurities including molecular oxygen. Sievers, U.S. Pat. No. 4,514,522, discloses oxygen sorbents comprising linear, tetradentate ketoamine complexes bound to porous polymers. Gagne, U.S. Pat. No. 4,475,994, uses cobalt complexes of unknown stoichiometry in a mixed solvent at high pH to transport electrochemically-generated superoxide ions across a fluid membrane. Bonaventura, et al., U.S. Pat. Nos. 4,602,987, 4,609,383, and 4,629,544, disclose a variety of metalloporphyrins, in combination with Lewis bases, in aqueous, non-aqueous, and water-immiscible solvents and their use to electrochemically separate oxygen from fluids.

Oxygen carrier compounds, including cobalt complexes of some linear, pentadentate polyamines, and their properties have been extensively reviewed and tabulated. Niederhoffer, et al., Chem. Rev. 84, 137–203 (1984). More detailed investigations of cobalt complexes of some linear, pentadentate polyamines have been reported in a series of articles by Harries, et al., and Timmons, et al. Inorg. Chem. 17, 889 (1978); Inorg. Chem. 17, 2192 (1978); Inorg. Chem. 18, 1042 (1979); Inorg. Chem. 18, 2977 (1979); Inorg. Chem. 19, 21 (1980); and Inorg. Chem. 21, 1525 (1982). The use of transition metal complexes of polyalkylamines in electrochemical or other oxygen extraction and generation processes is not known.

Unsymmetrical Compounds—Reversible oxygen transport and chemical activation by way of non-heme organometallic complexes is an area of great activity at the present time. Among the most successful ligands to be prepared so far are open-chain polyalkylarylamines (penta amines) possessing five nitrogen atoms which can be accommodated around transition metal ions such as cobalt(II) or iron(II). By virtue of their mode of synthesis (See FIG. 8, Scheme I), most of these ligands reported are symmetrical. Asymmetry in such molecules (unsymmetry) can be achieved either by use of commercially available unsymmetrical central triamines (e.g., where d≠q), or by use of two different moieties (e.g., $R_1$ or $R_2$, or $R^1$ or $R^2$) at the terminii of the molecules. Products from condensations of unsymmetrical central amines are still symmetrical in one sense that the aryl rings, R, introduced at the teminii of the chains must be identical (See FIGS. 24 and 25).

Some references of interest in this art include but are not limited to the following:

A. E. Martell, and D. T. Sawyer, (eds.), *Oxygen Complexes and Activation by Transition Metals*, Plenum Press, New York, 1988.

E. C. Niederhoffer, et al. (1984) *Chemical Reviews*, Vol. 84 p. 137.

J. L. Reibsomer, et al. (1949) *Journal of the American Chemical Soc.*, 1949 p. 245.

M. M. Bagga, et al., *J. Chem. Soc., Chem. Commun.*, (1987), p. 259,

J. P. Dutasta, et al., *J. Organie. Chem.*, (1988), Vol. 53, p. 1817.

H. Chikashita, et al. *Bull. Chem. Soc. Jpn.*, (1987), Vol. 60 p. 737.

D. W. Gruenwedel, (1968) *Inorganic Chemistrty*, Vol. 7, p. 495.

These symmetrical and/or unsymmetrical compounds are useful as prechelate compounds. When contacted with a solution of transition metal ion, the metal chelate is obtained. The metal chelate in aqueous solution is useful for binding and releasing ligands, such as oxygen on demand.

It would be useful to have a synthetic method to prepare symmetrical and unsymmetrical prechelate compounds for use in ligand binding and release on demand. The present invention provides such compound and methods.

SUMMARY OF THE INVENTION

Methods and apparatus for extraction of a ligand such as molecular oxygen from a first fluid environment and for release of a ligand such as molecular oxygen to a second fluid environment are disclosed, as well as ligand carrier compounds therefor comprising linear, pentadentate polyalkylamines and transition metal ions. The carrier compounds have the general formula:

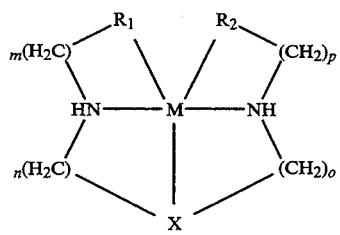

wherein, each of $R_1$ and $R_2$ is independently an organic group including a sulfur, an oxygen or a nitrogen coordinated to M;

each of m, n, o, and p is independently 1, 2, 3, or 4;

X is selected from the group consisting of 2,6-pyridyl, 2,6-piperidyl, 2,5-pyrrolyl, 2,4-imidazolyl, substituted heterocyclic amines, —O—, —S—, >P—$R_3$, and >N—$R_3$ where $R_3$ is hydrogen, lower alkyl, or aralkyl; and M is a transition metal ion.

Typical methods according to the invention include: contacting a first fluid environment containing a ligand with the first surface of a first ligand-permeable membrane having a first and second surface wherein the membrane separates the environment from an interior space of a container; contacting a carrier fluid with the second surface of the membrane wherein the carrier fluid is confined in the container and the carrier fluid contains a carrier compound, whereby at least a portion of a ligand which diffuses through the membrane binds to the carrier compound to give bound ligand complex; transporting the carrier fluid containing the bound ligand complex to a first electrode compartment of an electrochemical cell which forms a second portion of the container; electrochemically modulating the carrier compound to an oxidation state having relatively less binding affinity for ligand, thereby releasing free ligand into the carrier fluid and producing a non-binding state carrier compound; removing ligand from the carrier fluid to give a ligand-depleted carrier fluid; transporting the ligand-depleted carrier fluid containing the non-binding state carrier compound to a second electrode compartment of an electrochemical cell which forms a third portion of the container; and electrochemically modifying the non-binding state carrier compound to reform the binding state carrier compound.

Typically, an apparatus used for the extraction of a ligand such as oxygen from fluids, for example, air or seawater, will comprise an oxygen loading station in which an oxygen (or ligand) binding carrier compound in this reduced valence state is transported past an oxygen permeable membrane in contact with the first fluid environment from which oxygen is being extracted. A carrier fluid containing the carrier compound is transported through an apparatus through a conducting system which seals the carrier fluid from both the first fluid environment (occasionally referred to herein as an external fluid environment) and a second fluid environment (sometimes referred to herein as the internal environment) into which oxygen is being released. The reduced state oxygen carrier is oxidized at the anode of an electrochemical cell, and the carrier fluid containing free dissolved or gaseous oxygen is transported to a separate location, generally, an "unloader," where the oxygen passes into the interior environment, in some embodiments, through an oxygen permeable membrane. The carrier fluid containing the oxidized-state carrier compound is then circulated back through a cathode compartment of an electrochemical cell where the reduced state oxygen carrier is reformed by electrochemical reduction. The carrier fluid containing the reduced state oxygen carrier is then transported back to the oxygen loading station, after which the entire operation can be repeated.

Other methods and apparatus according to the invention utilize diffusive transport of oxygen or other ligands as ligands-carrier complexes between electrodes of an electrochemical cell either in conjunction with ligand-permeable membranes or using ligand-permeable electrodes.

Although reference will be made to "oxygen carriers" and "oxygen binding compounds," many of the carrier compounds according to the invention reversibly bind other small molecules, or "ligands," such as carbon monoxide, carbon dioxide, nitric oxide, cyanide, isocyanide, hydroxide, and the like. It will be understood that the invention is intended to comprehend extraction (from an appropriate fluid medium), transport, and regeneration or release of such ligands as well as oxygen, where the carrier compounds of the invention reversibly bind such ligands and have differential affinities for such ligands in the oxidized and reduced states of the carrier compounds.

Preferred embodiments include those wherein the Structure of the prechlete compound is subject to certain provisos, e.g. when $R^1$ and $R^2$ are the same group, e.g. 2-pyridyl, and X is 2,6-pyridyl, then m, n, o and p are not one. Also when $R^1$ and $R^2$ are the same, e.g. 2-pyridyl, and X is N—H, then m and p are not one and n and o are not 3.

SUMMARY OF THE INVENTION

The present invention relates to an improved process to produce a symmetrical or an unsymmetrical prechelate compound of Structure I:

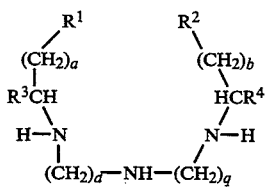

or a salt thereof, wherein $R^1$ and $R^2$ are each independently selected from aliphatic, alicyclic, or aromatic organic compounds each containing at least one nitrogen, sulfur or oxygen atom which is suitable for coordination to a transition metal ion, with the proviso that $R^1$ and $R^2$ are independently the same or are different chemical groups, $R^3$ and $R^4$ are each independently selected from —H or —$CH_3$, a and b are each independently 0, 1 or 2, d and q are each independently selected from 1, 2, 3, 4 or 5 which process comprises:

(a) contacting about one equivalent of a compound of the structure:

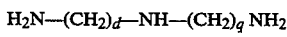

$H_2N—(CH_2)_d—NH—(CH_2)_q NH_2$ with about one equivalent of $R^1—(CH_2)_a(C=O)R^3$ where $R^1$, a, d and q are defined above, is an aromatic compound, an organic solvent under conditions sufficient to produce a compound of Structure II;

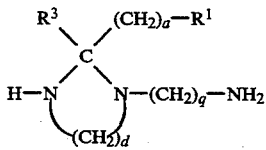

(b) contacting the product of step (a) with about one equivalent of $R^2—(CH_2)_b(C=O)R^4$, wherein b, $R^2$ and $R^4$ are defined above in an organic solvent under conditions sufficient to substantially remove all of the water produced by condensation;

(c) removing the organic solvent to isolate the imine product;

(d) contacting the imine product with an organic solvent under reducing conditions effective to selectively reduce at least one imine and the diazaalkylene ring; and (e) recovering the compound of structure (I)

In preferred embodiments of the process of the present invention:

$R^1$ and $R^2$ are the same chemical group;

$R^1$ and $R^2$ are different chemical groups;

Structure I is a symmetrical prechelate compound;

$R^1$ and $R^2$ each contain at least one nitrogen atom;

Structure I is a unsymmetrical prechelate compound;

or $R^1$ and $R^2$ each contain at least one nitrogen atom.

In another aspect the present invention relates to an organic compound of the general structure (I):

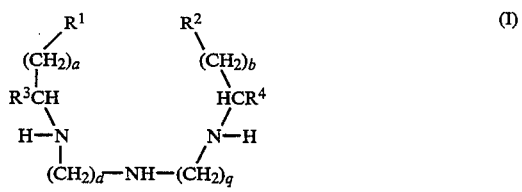

wherein $R^1$ and $R^2$ are each independently selected from aliphatic, alicyclic, or aromatic organic groups which contain at least one nitrogen, sulfur, or oxygen atom which is suitable for coordination of a transition metal ion, with the proviso that $R^1$ and $R^2$ are the same or different chemical groups;

$R^3$ and $R^4$ are each independently selected from —H or —$CH_3$, a and b are each independently 0, 1 or 2, and d and q are each independently selected from 1, 2, 3, 4 or 5.

In another aspect the present invention relates to an organic metal ion chelate compound of structure (Ia)

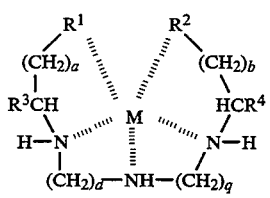

comprising the compound of structure I and a transition metal ion.

BRIEF DESCRIPTION OF THE FIGURES

A more complete appreciation of the invention and many of the attendant advantages thereof will be better understood by reference to the following detailed description of the specific embodiments thereof when considered in connection with the accompanying drawings, wherein:

FIG. 1 is a plot representing the variation with pH of the optical absorbance at 330 nanometers (nm) of selected carrier compounds according to the invention.

FIG. 2 is a plot representing the results of potentiometric pH titrations of selected polyalkylamines according to the invention.

FIG. 3 is a plot representing the results of potentiometric pH titrations of selected cobalt carrier compounds according to the invention.

FIG. 4 is a plot representing the results of potentiometric pH titrations of complexes with molecular oxygen of selected cobalt carrier compounds according to the invention.

FIG. 5 is a plot representing the endpoints of potentiometric pH titrations of selected carrier compounds according to the invention and their molecular oxygen complexes, along with initial working pH values for these carrier compounds as determined from the titrations of the corresponding oxygen complexes.

FIG. 6 is a plot of cyclic voltammetry trace for the oxygenated cobalt carrier compound of polyalkylamine No. 76 using an initial voltage of 0.19 V vs. an Ag/AgCl reference electrode, an initially negative sweep rate of 50 mV/s, and a glassy carbon working electrode.

FIG. 7 is a schematic diagram illustrating an apparatus for practice of the methods of the invention.

FIG. 8 is a schematic diagram illustrating an Electrochemical Oxygen Cell (EOC) used for preliminary evaluation of the properties of individual carrier compounds for use practicing the methods of the invention.

FIG. 9 is a schematic diagram of a specific embodiment of an apparatus for the practice of the methods of the invention, showing manufacturing parameters for this apparatus.

FIG. 10 is a schematic diagram of a second specific embodiment of an apparatus for the practice of the methods of the invention.

FIG. 11 is a plot showing the power consumption, in thousands of watts, required in an EOC using the carrier compound cobalt bishistidine, disclosed by Bonaventura.

FIG. 12 is a plot showing the power consumption, in watts, required in an EOC using the MPAA carrier compounds cobalt 1,11-bis (2-(1-methylimidazolyl))-2,5,10-triazaundecane (Co(PAA No. 192)).

FIG. 13 is a plot showing the oxygen production of an EOC using cobalt bishistidine.

FIG. 14 is a plot showing the oxygen production of an EOC using cobalt 1.11-bis(2-(1-methylimidazolyl))-2,5,10-triazaundecane (PAA 192).

FIG. 15 indicates the current density in an EOC using cobalt bishistidine (PAA 192).

FIG. 16 indicates the current density in an EOC using cobalt 1,11-bis(2-(1-methylimidazolyl))-2,5,10-triazaundecane.

UNSYMMETRICAL COMPUNDS

Figure 25:
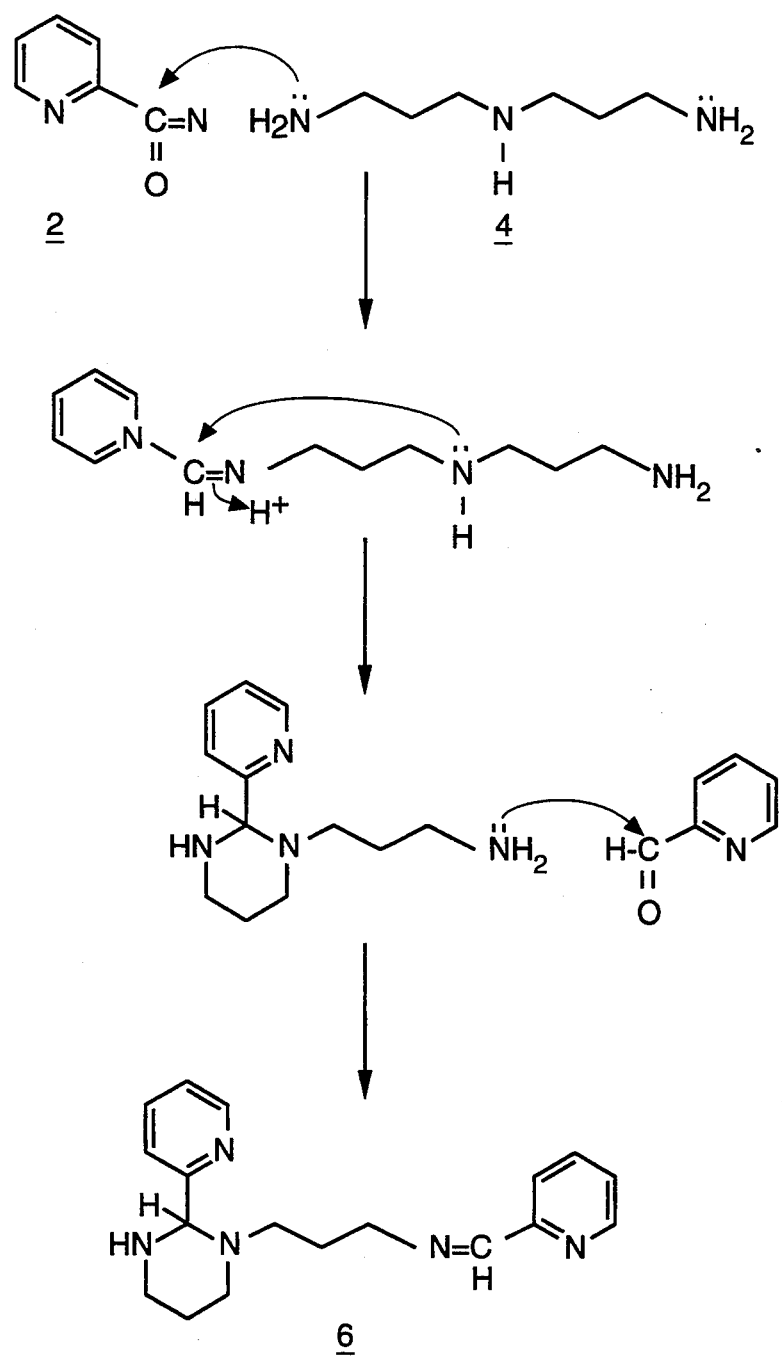

FIG. 17 (Table IA) shows some reaction sequences to assess the effect of steric congestion and ring size on cyclization to produce unsymmetrical polyalkylarylamines.

FIG. 18 shows additional general reactions demonstrating the importance of steoric congest ion on the type of product obtained.

FIG. 19 shows the sequences of steps to produce symmetrical polyamine and the structure of the imine a hexa-hydropyrimidine intermediate.

FIG. 20 shows the sequence of steps to produce an unsymmetrical polyalkylarylamine.

FIG. 21 shows unsymmetrical compounds, one having a benzyl-imidazolyl moiety.

FIG. 22 shows a coupling reaction where X is equal to 2,6-diformylpyridine to produce a symmetrical compound and also a unsummetrical imidazole.

FIG. 23 shows structures of cyclic intermediates wherein the alkylene groups between the nitrogen atoms are not equal.

FIG. 24 (Scheme 1) shows a synthetic route to produce the symmetrical polyalkylamine.

FIG. 25 (Scheme 2) is a mechanistic interpretation of the formation of the cyclic intermediate.

DETAILED DESCRIPTION OF THE SPECIFIC EMBODIMENTS

The chelating ligands which may be used to form the transition metal carrier compounds of the present invention and of potential use in electrochemical ligand extraction, transport, and generation processes according to the present invention are generally linear (as opposed to branched, macrocyclic, or tripod-type ligands) and pentadentate. At least four of the atoms available for coordination to the selected transition metal ion (generally referred to herein as "ligating atoms") will be nitrogen. Hence, chelating ligands of the present invention will generally be referenced to as polyalkylamines, and will frequently be generically abbreviated "PAA." The remaining ligating atom, usually the third or central ligating atom, will usually be nitrogen or oxygen, although sulfur and phosphorus atoms may find use. The ligating nitrogens may be of the primary aliphatic, secondary aliphatic, tertiary aliphatic, or aromatic type; one or more such types of nitrogen may generally be present in the same polyalkylamine. Ligating oxygen, when present in a particular PAA, will usually be of the ether type, while ligating sulfur will be a thioether. The polyalkylamines of a type useful in the present invention will include those of the general formula:

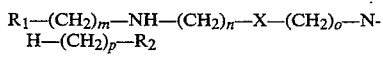

wherein,

X may be 2,6-pyridyl, 2,6-piperidyl, 2,5-pyrrolyl, 2,4-imidazolyl, substituted heterocyclic amines, —O—, —S—, >P—$R_3$, or >N—$R_3$ where $R_3$ is hydrogen, lower alkyl, or aralkyl;

each of m, n, o, and p is independently 1, 2, 3, or 4; and each of $R_1$ and $R_2$ is independently an organic group having a sulfur, an oxygen or a nitrogen atom of the primary aliphatic, secondary aliphatic, tertiary aliphatic, heterocyclic, or heteroaromatic type which is also available for coordination to a transition metal ion.

As examples, $R_1$ and $R_2$ may each be selected from the group including, but not limited to, amino; alkylamino; dialkylamino; 2-pyridyl; substituted 2-pyridyl such as 2-(6-methyl)pyridyl; 2-piperidyl; substituted 2-piperidyl; 2-imidazolyl; 4-imidazolyl; substituted 2- or 4-imidazolyl such as 2-(1-methylimidazolyl), 2-benzimidazolyl, 2-(1-benzylimidazolyl) and 4-(5-methylimidazolyl); 2-pyrrolyl; alkyl-substituted 2-pyrrolyl; 2-pyrazinyl; 2-indolyl; 1-isoindolyl; 3-isoindolyl; 2-quinolinyl; 8-quinolinyl; alkyl-substituted 2- or 8-quinolinyl; 2-thiazolyl; 2-thienyl; substituted thienyl; 2-furyl; and substituted 2-furyl. $R_1$ and $R_2$ may, in any particular polyalkylamine, be the same or different.

The alkyl chains interconnecting the ligating atoms may themselves be branched or substituted with, e.g., short-chain alkyl groups such as methyl, ethyl, n- or i-propyl, or n-, s-, or t-butyl, or with relatively small heterogroups such as acetyl, methyl acetyl, hydroxymethyl, hydroxyethyl, halomethyl, or haloethyl, where "halo" denotes F, Cl, Br, or I.

Representative examples of specific polyalkylamine (PAA) compounds presently contemplated for use in the invention are listed in Table I. In Table I (and the remainder of the present disclosure), the compounds numbers (PAA Nos.) have been arbitrarily chosen for ease of reference and have no independent significance; however, these compounds numbers will be used in the following discussion to refer to particular compounds. The presently preferred polyalkylamines for use according to the invention are listed in Table II, along with literature abbreviations, where known, that have previously been used for particular polyalkylamines.

EXAMPLE I

Preparation of 1,11-Bis(2-Pyridyl)-2,6,10-Triazaundecane . 3HCl (PAA No. 64)

Pyridine-2-carboxaldeyde (4.3 g, 0.04 mole) and 1,5,9-triazanonane (2.6 g, 0.02 mole) (bis(aminopropyl)amine, available, for example from Aldrich Chemical Company) were dissolved in ca. 60 mL of absolute ethanol and warmed (ca. 50° C.) with stirring for 10 minutes. The solution was hydrogenated at room temperature over 1.5 g of 5% Pd on charcoal in an atmosphere of hydrogen. After the calculated amount of hydrogen (0.04 mole; ca. 0.90L at 25° C. and 1 atm. pressure) had been consumed, the charcoal catalyst was removed by filtration, and dry HCl gas was bubbled into the solution until no further white precipitate formed. After removing the precipitate by filtration of the cooled solution, the product was washed with absolute ethanol, dried, and recrystallized from 95% ethanol.

The product was then dissolved in a minimum amount of a solution of about 70% v/v methanol and about 30% v/v concentrated ammonium hydroxide. This solution was chromatographed on a column of silica gel F254 using the same solvent mixture. The eluate containing the product was partially evaporated under vacuum with heating (ca. 70°–80° C.), cooled, and filtered to remove the precipitated silica (dissolved from the column during chromatography), and then evaporated to dryness. The purified product was again recrystallized from 95% ethanol. The product could also be successfully purified by chromatography on silica gel using a solvent comprising about 66% chloroform, 5% triethylamine, and 29% methanol.

The following characterization of the product polyalkylamine trihydrochloride was obtained by standard techniques: M.P. 263°–265° C.; UV (0.04 mg/mL in methanol): $_{max}$=258.5 nm, $_{max}$=5540; elemental analysis: theory=51.12% C, 7.17% H, 16.56% N, 25.25% Cl; found=50.83% C, 7.06% H, 16.45% N, 24.97% Cl; thin layer chromatography (TLC) on a silica gel F-254 plate, with methanol:ammonium hydroxide (10:3) solvent and UV/Iodine detection indicated a single spot with $R_f$=0.6.

EXAMPLE II

1,10-Bis-(2-Pyridyl)-2,5,9-Triazadecane . 3HCl (PAA No. 72)

The preparation and purification of this polyalkylamine were accomplished by the procedure of Example I substituting 1,5,8-triazaoctane (2.3 g; 0.02 mole) ((aminoethyl) (aminopropyl)amine; available from Aldrich Chemical Company) for bis(aminopropyl)amine. The following characterization of the purified product by standard techniques was obtained: UV (0.04 mg/mL in methanol): $_{max}$ 259 nm, $_{max}$ 5,500; elemental analysis: theory 49.73% C, 6.92% H, 17.06% N, 25.90% Cl; found (after correction for 0.2% water determined by Karl Fischer analysis) 49.48% C, 6.83% H, 17.01% N, 26.42% Cl; TLC analysis on silica gel F-254 with methanol: ammonium hydroxide solvent yielded a main spot at $R_f$=0.7 and a faint spot (<1%) at $R_f$=0.2.

EXAMPLE III

Preparation of 1,11-Bis(2-(1-Benzylimidazolyl))-2,6,10-Triazaundecane . 3HCl (PAA No. 118)

The preparation and purification of this polyalkylamine was accomplished by the procedure of Example I, except that 1-benzylimidazole-2-carboxaldehyde (7.44 g, 0.04 mole) was substituted for pyridine-2-carboxaldehyde.

TABLE I

REPRESENTATIVE POLYALKYLAMINE LIGANDS $R_3$—$(CH_2)_m$—NH—$(CH_2)_n$—X—$(CH_2)_o$—NH—$(CH_2)_p$—$R_2$

| PAA No. | $R_3$ | $R_2$ | X | m | n | o | p | Alkyl Branch |
|---|---|---|---|---|---|---|---|---|
| 21 | 2-pyridyl | 2-pyridyl | 2,6-pyridyl | 1 | 1 | 1 | 1 | |
| 33 | amino | amino | NH | 2 | 2 | 2 | 2 | |
| 62 | 2-pyridyl | 2-pyridyl | NH | 1 | 2 | 2 | 1 | |
| 63 | 2-pyridyl | 2-pyridyl | 2,6-pyridyl | 2 | 1 | 1 | 2 | |
| 64 | 2-pyridyl | 2-pyridyl | NH | 1 | 3 | 3 | 1 | |
| 68 | amino | amino | 2,6-pyridyl | 2 | 1 | 1 | 2 | A |
| 69 | amino | amino | 2,6-pyridyl | 2 | 1 | 1 | 2 | |
| 70 | amino | amino | 2,6-pyridyl | 3 | 1 | 1 | 3 | |
| 71 | 2-pyridyl | 2-pyridyl | O | 1 | 2 | 2 | 1 | |
| 72 | 2-pyridyl | 2-pyridyl | NH | 1 | 2 | 3 | 1 | |
| 73 | 2-imidazolyl | 2-imidazolyl | NH | 1 | 3 | 3 | 1 | |
| 74 | 4-imidazolyl | 4-imidazolyl | NH | 1 | 3 | 3 | 1 | |
| 75 | 4-imidazolyl | 4-imidazolyl | NH | 1 | 2 | 2 | 1 | |
| 76 | 2-pyridyl | 2-pyridyl | N—CH$_3$ | 1 | 3 | 3 | 1 | |
| 77 | 2-pyridyl | 2-pyridyl | N—CH$_3$CH$_3$ | 1 | 3 | 3 | 1 | |
| 78 | 2-pyridyl | 2-pyridyl | NH | 1 | 3 | 4 | 1 | |
| 79 | 2-BzIm | 2-BzIm | 2,6-pyridyl | 1 | 1 | 1 | 1 | |
| 80 | 2-(6-MePy) | 2-(6-MePy) | NH | 1 | 2 | 2 | 1 | |
| 81 | 2-(6-MePy) | 2-(6-MePy) | NH | 1 | 3 | 3 | 1 | |
| 82 | 2-pyridyl | 2-pyridyl | NH | 1 | 2 | 2 | 1 | B |
| 83 | 2-pyridyl | 2-pyridyl | NH | 1 | 3 | 3 | 1 | C |
| 84 | 2-pyridyl | 2-(6-MePy) | NH | 1 | 2 | 2 | 1 | |

TABLE I-continued
REPRESENTATIVE POLYALKYLAMINE LIGANDS
$R_3-(CH_2)_m-NH-(CH_2)_n-X-(CH_2)_o-NH-(CH_2)_p-R_2$

| PAA No. | $R_3$ | $R_2$ | X | m | n | o | p | Alkyl Branch |
|---|---|---|---|---|---|---|---|---|
| 85 | 2-pyridyl | 2-(6-MePy) | NH | 1 | 3 | 3 | 1 | |
| 86 | 2-pyridyl | 4-imidazolyl | NH | 1 | 3 | 3 | 1 | |
| 87 | 2-pyridyl | 4-imidazolyl | NH | 1 | 2 | 2 | 1 | |
| 88 | 2-pyridyl | 2-imidazolyl | NH | 1 | 3 | 3 | 1 | |
| 89 | 2-imidazolyl | 4-imidazolyl | NH | 1 | 3 | 3 | 1 | |
| 90 | 8-quinolinyl | 8-quinolinyl | NH | 1 | 3 | 3 | 1 | |
| 91 | 8-quinolinyl | 8-quinolinyl | NH | 1 | 2 | 2 | 1 | |
| 92 | 2-quinolinyl | 2-quinolinyl | NH | 1 | 3 | 3 | 1 | |
| 93 | 2-quinolinyl | 2-quinolinyl | NH | 1 | 2 | 2 | 1 | |
| 94 | 4-imidazolyl | 4-imidazolyl | 2,6-pyridyl | 2 | 1 | 1 | 2 | D |
| 95 | 4-(NbIm) | 4-(NbIm) | 2,6-pyridyl | 2 | 1 | 1 | 2 | D |
| 116 | 2-imidazolyl | 2-imidazolyl | NH | 1 | 2 | 2 | 1 | |
| 117 | 2-(NbIm) | 2-(NbIm) | NH | 1 | 2 | 2 | 1 | |
| 118 | 2-(NbIm) | 2-(NbIm) | NH | 1 | 3 | 3 | 1 | |
| 119 | 4-imidazolyl | 4-imidazolyl | NH | 1 | 2 | 3 | 1 | |
| 120 | 2-(NbIm) | 2-pyridyl | NH | 1 | 3 | 3 | 1 | |
| 121 | 2-(NbIm) | 2-(NbIm) | NH | 1 | 2 | 3 | 1 | |
| 122 | 2-pyridyl | 2-pyridyl | N—$CH_3$ | 1 | 3 | 3 | 1 | C |
| 123 | 2-(5-ClTh) | 2-(5-ClTh) | NH | 1 | 3 | 3 | 1 | |
| 124 | 2-furyl | 2-furyl | NH | 1 | 3 | 3 | 1 | |
| 125 | (2-OH)phenyl | (2-OH)phenyl | NH | 1 | 3 | 3 | 1 | |
| 126 | 2-pyrazinyl | 2-pyrazinyl | NH | 1 | 3 | 3 | 1 | C |
| 127 | 2-thiazolyl | 2-thiazolyl | NH | 1 | 3 | 3 | 1 | C |
| 128 | 2-(3-MeTh) | 2-(3-MeTh) | NH | 1 | 3 | 3 | 1 | |
| 129 | 2-(5-MeTh) | 2-(5-MeTh) | NH | 1 | 3 | 3 | 1 | |
| 131 | 2-imidazolyl | 2-imidazolyl | NH | 1 | 3 | 4 | 1 | |
| 132 | 2-(1-MeIm) | 2-(1-MeIm) | NH | 1 | 2 | 2 | 1 | |
| 133 | 2-(1-MeIm) | 2-(1-MeIm) | NH | 1 | 2 | 3 | 1 | |
| 134 | 2-(1-MeIm) | 2-(1-MeIm) | NH | 1 | 3 | 4 | 1 | |
| 135 | 4-(5-MeIm) | 4-(5-MeIm) | NH | 1 | 2 | 2 | 1 | |
| 136 | 4-(5-MeIm) | 4-(5-MeIm) | NH | 1 | 2 | 3 | 1 | |
| 137 | 4-(5-MeIm) | 4-(5-MeIm) | NH | 1 | 3 | 4 | 1 | |
| 138 | 2-(1-MeIm) | 2-pyridyl | NH | 1 | 3 | 3 | 1 | |
| 150 | 2-pyridyl | 2-pyridyl | NH | 1 | 2 | 4 | 1 | |
| 151 | 2-pyridyl | 2-pyridyl | S | 1 | 2 | 2 | 1 | |
| 152 | 2-pyridyl | 2-pyridyl | S | 1 | 2 | 3 | 1 | |
| 153 | 2-pyridyl | 2-pyridyl | NH | 1 | 2 | 3 | 1 | K |
| 155 | 4-imidazolyl | 4-imidazolyl | S | 1 | 2 | 2 | 1 | |
| 162 | 8-quinolinyl | 8-quinolinyl | NH | 1 | 2 | 3 | 1 | |
| 164 | 4-imidazolyl | 4-imidazolyl | NH | 1 | 3 | 4 | 1 | |
| 165 | 4-imidazolyl | 4-imidazolyl | O | 1 | 2 | 2 | 1 | |
| 166 | 4-imidazolyl | 4-imidazolyl | NH | 1 | 3 | 3 | 1 | |
| 167 | 4-(5-MeIm) | 4-(5-MeIm) | NH | 1 | 3 | 3 | 1 | |
| 168 | 2-(NbIm) | 2-(NbIm) | S | 1 | 2 | 2 | 1 | |
| 169 | 2-pyridyl | 2-pyridyl | N—$CH_3$ | 1 | 3 | 3 | 1 | F |
| 170 | 2-pyridyl | 2-pyridyl | NH | 1 | 3 | 3 | 1 | F |
| 171 | 2-(NbIm) | 2-(NbIm) | NH | 1 | 3 | 4 | 1 | |
| 172 | 2-(NbIm) | 2-(NbIm) | N—$CH_3$ | 1 | 3 | 3 | 1 | |
| 180 | 4-imidazolyl | 4-imidazolyl | NH | 1 | 2 | 4 | 1 | |
| 181 | 2-(NbIm) | 2(NbIm) | NH | 1 | 2 | 4 | 1 | |
| 184 | amino | amino | S | 2 | 2 | 2 | 2 | |
| 189 | 2-(1-MeIm) | 2-(1-MeIm) | NH | 1 | 3 | 3 | 1 | |
| 190 | 2-imidazolyl | 2-imidazolyl | NH | 1 | 2 | 4 | 1 | |
| 191 | 4-(5-MeIm) | 4-(5-MeIm) | NH | 1 | 2 | 4 | 1 | |
| 192 | 2-(1-MeIm) | 2-(1-MeIm) | NH | 1 | 2 | 4 | 1 | |
| 193 | 2-(1-ViIm) | 2-(1-ViIm) | NH | 1 | 3 | 3 | 1 | |

Abbreviations used:
2-(BzIm)=2-benzimidazolyl
2-(6-MePhy)=2-(6-methyl)pyridyl
4-(NbIm)=4-(1-benzyl)imidazolyl
2-(NbIm)=2-(1-benzyl)imidazolyl
2-(1-MeIm)=2-(1-methyl)imidazaolyl
4-(5-MeIm)=4-(5-methyl)imidazolyl
2-(1-ViIm)=2-(1-vinyl)imidazolyl
2-(5-ClTh)=2-(5-chloro)thienyl
2-(3-MeTh)=2-(3-methyl)thienyl
2-(5-MeTh)=2-(5-methyl)thienyl Alkyl Branching:
A=carbons 1 and 11' are methyl substituted
B=carbons 1 and 9 are methyl substituted
C=carbons 1 and 11 are methyl substituted
D=carbons 1 and 1' are methyl substituted; carbons 3 and 3' are methyl acetylated
E=carbons 1 and 10 are methyl substituted
F=carbons 1 and 11 are dimethyl substituted

TABLE II
SELECTED POLYALKYLAMINE LIGANDS

| PAA No. | Name | Literature Abbreviation |
|---|---|---|
| 21 | 2,6-Bis(1-(3-(2-Pyridyl)-2-Azapropyl))Pyridine | DMPAP |

TABLE II-continued
SELECTED POLYALKYLAMINE LIGANDS

| PAA No. | Name | Literature Abbreviation |
|---|---|---|
| 33 | 1,4,7,10,13-Pentaazatridecane | TETREN |
| 62 | 1,9-Bis(2-Pyridyl)-2,5,8-Triazanonane | PYDIEN |
| 63 | 2,6-Bis(1-(4-(2-Pyridyl)-2-Azabutyl))Pyridine | |
| 64 | 1,11-Bis(2-Pyridyl)-2,6,10-Triazaundecane | PYDPT |
| 68 | 2,6-Bis(5-(1,4-Diazahexyl))Pyridine | EPYDEN |
| 69 | 2,6-Bis(5-(1,4-Diazapentyl))Pyridine | |
| 70 | 2,6-Bis(6-(1,5-Diazahexyl))Pyridine | |
| 72 | 1,10-Bis(2-Pyridyl)-2,5,9-Triazadecane | |
| 73 | 1,11-Bis(2-Imidazolyl)-2,6,10-Triazaundecane | 2-IMDPT |
| 74 | 1,11-Bis(4-Imidazolyl)-2,6,10-Triazaundecane | 4-IMDPT |
| 75 | 1,9-Bis(4-Imidazolyl)-2,5,8-Triazanonane | 4-IMDIEN |
| 76 | 1,11-Bis(2-Pyridyl)-6-Methyl-2,6,10-Triazaundecane | |
| 78 | 1,12-Bis(2-Pyridyl)-2,6,11-Triazadodecane | |
| 80 | 1,9-Bis(2-(6-Methylpyridyl))-2,5,8-Triazanonane | |
| 81 | 1,11-Bis(2-(6-Methylpyridyl))-2,6,10-Triazaundecane | |
| 92 | 1,11-Bis(2-Quinolinyl)-2,6,10-Triazaundecane | |
| 93 | 1,9-Bis(2-Quinolinyl)-2,5,8-Triazanonane | |
| 116 | 1,9-Bis(2-Imidazolyl)-2,5,8-Triazanonane | |
| 117 | 1,9-Bis(2-(1-Benzylimidazolyl))-2,5,8-Triazanonane | |
| 118 | 1,11-Bis(2-(1-Benzylimidazolyl))-2,6,10-Triazaundecane | |
| 119 | 1,10-Bis(4-Imidazolyl)-2,5,9-Triazadecane | |
| 133 | 1,10-Bis(2-(1-Methylimidazolyl))-2,5,9-Triazadecane | |
| 180 | 1,11-Bis(4-Imidazolyl)-2,5,10-Triazaundecane | |
| 189 | 1,11-Bis(2-(1-Methylimidazolyl))-2,6,10-Triazaundecane | |
| 190 | 1,11-Bis(2-Imidazolyl)-2,5,10-Triazaundecane | |
| 191 | 1,11-Bis(4-(5-Methylimidazolyl))-2,5,10-Triazaundecane | |
| 192 | 1,11-Bis(2-(1-Methylimidazolyl))-2,5,10-Triazaundecane | |

The carrier compounds may be coordination complexes of any of a variety of transition metals including titanium, manganese, chromium, iron, cobalt, nickel, copper, ruthenium, rhodium, palladium, osmium, iridium, and platinum. Usually, the transition metal will be manganese, iron, or cobalt, but the invention is not so limited. Other transition metals that form complexes that reversibly bind molecular oxygen may also be used; complexes of such metals are contemplated to be within the scope of the present invention. The primary requisites of the transition metal are that it form complexes, have a first valence state in which the transition metal complex reversibly binds molecular oxygen or another ligand of interest, and have a second valence state in which the transition metal complex has a substantially lower affinity toward molecular oxygen or other ligand. Preferably, the metal is chosen to be, in its second valence state, substantially unreactive with molecular oxygen or other ligand of interest. In addition, the valence state of the transition metal(s) used will be electrochemically modulable. In known transition, metal complexes which will be suitable to use, the valence state in which oxygen is reversibly bound will be lower (more reduced), e.g., Mn(II), Fe(II), Co(II) or Cu(I). This lower valence state will be generally referred to herein as the "binding state." The non-binding state (generally referred to herein as the "non-binding state") will generally be higher and achieved via a one-electron oxidation of the lower valence state, e.g., Mn(III), Fe(III), Co(III), or Cu(II).

The carrier compounds according to the present invention comprise, generally, ions of one of the above transition metals reacted with a polyalkylamine chelating ligand. The carrier compounds may be prepared and isolated as will be outlined below. Alternatively, since many of the polyalkylamines according to the present invention have a very high affinity for metal ions such as cobaltous ion, suitable carrier compounds may be prepared in situ during the preparation of carrier solutions for the extraction, transport, and regeneration of small ligands, e.g., molecular oxygen. Preparation of carrier compounds in situ is accomplished in such instances by the addition of equimolar amounts of the metal ion, e.g., 1 millimole/liter $Co^{2+}$, and polyalkylamine, e.g., 1 mM/L PAA, to a particular carrier fluid.

Carrier compounds useful in the present invention will thus have the general formula $M(PAA)^{n+}$, where M is a transition metal ion and PAA is a pentadentate polyalkylamine ligand. The charge on the carrier compound will depend on the valence state of the metal ion, the extent of ionization of the polyalkylamine, the pH of the carrier solution, etc. Sufficient counterions will accompany carrier compounds (whether as solids or in solution) to counterbalance this charge. The counterions will usually be anions and will be both chemically and electrochemically unreactive under the conditions to be employed for extraction, transport, or regeneration of molecular oxygen. Counteranions will typically be small, unreactive anions such as: halide ions, e.g., fluoride, sulfate, or phosphate; or organic ions, e.g., acetate or citrate. For convenience, the carrier compounds may be designated herein "M(PAA)." It will be understood that this designation will include both charged and uncharged carrier compounds and that charged carrier compounds will be understood to be accompanied by suitable counterions. Carrier compounds according to the present invention will thus generally be metallic complexes having the general formula:

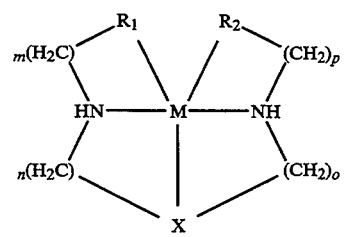

wherein,

X may be 2,6-pyridyl, 2,6-piperidyl, 2,5-pyrrolyl, 2,4-imidazolyl, substituted heterocyclic amines, —O—, —S—, >P—$R_3$ or >N—$R_3$ where $R_3$ is hydrogen, lower alkyl, or aralkyl;

each of m, n, o, and p is independently 1, 2, 3, or 4;

each of $R_1$ and $R_2$ is independently an organic group having a sulfur, an oxygen or a nitrogen atom of the primary aliphatic, secondary aliphatic, tertiary aliphatic, heterocyclic, or heteroaromatic type which is also available for coordination to a transition metal ion; and M is a transition metal ion.

As examples, $R_1$ and $R_2$ may each be selected from the group including, but not limited to, amino; alkylamino; dialkylamino; 2-pyridyl; substituted 2-pyridyl such as 2-(6-methyl)pyridyl; 2-piperidyl; subsituted 2-piperidyl; 2-imidazolyl; 4-imidazolyl; substituted 2- or 4-imidazolyl such as 2-(1-methylimidazolyl); 2-benzimidazolyl, 2-(1-benzylimidazolyl) and 4-(5-methylimidazolyl); 2-pyrrolyl; alkyl-substituted 2-pyrrolyl; 2-pyrazinyl; 2-indolyl; 1-isoindolyl; 3-isoindolyl; 2-quinolinyl; 8-quinolinyl; alkyl-substituted 2- or 8-quinolinyl; 2-thiazolyl; 2-thienyl; substituted 2-thienyl; 2-furyl; and substituted 2-furyl. $R_1$ and $R_2$ may, in any particular polyalkylamine, be the same or different.

The alkyl chains interconnecting the ligating atoms may themselves be branched or substituted with, e.g., short-chain alkyl groups such as methyl, ethyl, n- or s-propyl, or n-, s-, or t-butyl, or with relatively small heterogroups such as acetyl, methyl acetyl hydroxymethyl, hydroxyethyl, halomethyl, or haloethyl, where "halo" denotes F, Cl, Br, or I.

The metal ion M is selected from titanium, manganese, chromium, iron, coblat, nickel, copper, ruthenium, rhodium, palladium, osmium, irridium, and platinum. Usually, metal ion M will be manganese, iron or cobalt. Most frequently, M will be cobalt.

EXAMPLE IV

Preparation of [(Co(II) (1,11-Bis(2-(1-Benzylimidazolyl))-2,6,10-Triazaundecane)]$Cl_2$ (Co(PAA)$Cl_2$, with PAA No. 118)

Cobalt (II) chloride hexahydrate (2.4 g. 0.01 mole) and 1,11-bis (2-(1-benzylimidazolyl))-2,6,10-triazaundecane . 3HCl from Example III (4.7 g, 0.01 mole) are separately dissolved under a nitrogen atmosphere in deoxygenated water, and then are slowly mixed together under nitrogen and precipitated with deoxygenated acetone addition. After stirring for ca. 1 hour at room temperature, the pink product is removed by filtration, washed with deoxygenated ethanol, and dried.

The dimeric oxygen complex, [Co(PAA)$_2$$O_2$$Cl_4$, can be obtained by exposing the above solutions Go oxygen, with stirring, and evaporating the solvent.

The polyalkylamine carrier compounds according to the present invention may form both monomeric and dimeric complexes with molecular oxygen, although typically the dimeric complex is more readily and frequently observed. Using cobalt carrier compounds as an example, the following equilibria may generally be observed in aqueous solution, depending on such factors as the pH of the carrier fluid, the identities and relative concentrations of the various species, the temperature, and the solvent.

Unsymmetrical Chelates—The symmetrical and unsymmetrical polyalkylarylamines of the present invention may be prepared by a number of routes.

The compounds numbers which appear in the text will refer to the corresponding compound numbers in thee FIGS. 17 to 25.

One route is to combine the linear alkyl triamine (e.g. compounds (4) or (26)) with one equivalent of $R^1$—$(CH_2)_a$(C=O)—$R^3$ and one equivalent of $R^2$—$(CH_2)_b$(C=O)—$R^4$ where $R^1$, $R^2$, $R^3$ and $R^4$ and a, and b are defined hereinabove. The reactants are combined and are optionally heated, etc. for a time period effective to condense the amine and carbonyl and produce water. Optionally, the water produced is removed (e.g. as an azeotrope) to drive the condensation to completion. The water formed can be removed by any of the usual methods to separate water (e.g., molecular sieves, etc. See the Figures, particularly FIG. 24 and 25.

One compound is obtained when $R^1=R^2$, $R^3=R^4$, a=b, and d=q. A mixture of three compounds are obtained when $R^1{\neq}R^2$, $R^3=R^4$ a=b, and d=q. A mixture of four compounds are obtained when $R^1{\neq}R^2$ and $R_3=R^4$ a=b, and n${\neq}$q. As more of these structural moieties of structure I are not equal to each other, more complex mixtures of similar polyamine compounds are produced.

The reaction product is usually a mixture of three or four compounds which are produced and present in the general weight percent indicated:

$R^1(CH_2)_a CHR^3$ N $(CH_2)_d$ NH $(CH_2)_q$ N $CHR^3$ $(CH_2)_a$ $R^1$ (25%)

$R^1(CH_2)_a CHR^3$ N $(CH_2)_d$ NH $(CH_2)_q$ N $CHR^4$ $(CH_2)_b$ $R^2$ (25%)

$R^2(CH_2)_b CHR^4$ N $(CH_2)_d$ NH $(CH_2)_q$ N $CHR^3$ $(CH_2)_a$ $R^1$ (25%)

$R^2(CH_2)_b CHR^4$ N $(CH_2)_d$ NH $(CH_2)_q$ N $CHR^4$ $(CH_2)_b$ $R^2$ (25%)

The compounds of this mixture are useful as a chelate mixture when contacted with a transition metal ion as oxygen binding carriers. These polyalkylarylamines are also useful as metal corrosion inhibitors.

The mixture of polyalkylamines may be separated in small quantities using chromatography, e.g. high pressure liquid chromatography (HPLC), gas chromatography (GC), or thin layer chromatography (TLC), or combinations thereof. However, the separation may take a long time and is labor intensive.

Alternatively, a modification of the procedure shown in Scheme 1 (FIG. 24) results in the synthesis of a wide variety of unsymmetrically terminated polyalkylarylamines in substantially pure form which is substantially uncontaminated by the similar structures described hereinabove (See FIG. 25).

Condensation of 5-methyl-1,5,9-triazanonane (1) with two mole equivalents of 2-formylpyridine (2) produces a high yield of the bis-imine (3) ($^1$H NMR, CH=N, 8.1 ppm). However, similar reaction between 1,5,9-triazanonane (4) and two mole equivalents of 2-formylpyridine produces a product which on the basis of $^1$H NMR spectroscopy, could not be assigned the expected bis-imine structure (5). The NMR spectrum, instead of reflecting the symmetry observed for compound (3), showed considerable asymmetry, along with an anomalous one proton peak at 4.1 ppm. The chemical shift of this anomalous peak was appropriate for a proton flanked by a aromatic ring and two nitrogens, therefore the cyclic structure was assigned to the isolated product.

1,3-Diamines are known to condense with either aldehydes or ketones to give hexahydropyrimidines of type (7) or (8). However, no examples involving tri-amines or arylaldehydes or aryl ketones has been reported. A number of reactions of aryl aldehydes with 1,3-propanediamine are summarized in FIG. 1 (Table 1A). The reaction of diamine with compound (2) in boiling benzene produced a quantitative yield of the hexahydropyrimidine (9). When electron-rich aryl aldehydes are used e.g., ortho hydroxybenzaldehyde, only the imine (10) was produced. Benzaldehyde itself gave a mixture of hexahydropyrimidine (11) (40%) and imine (12) (60%), while the relative proportions of hexahydropyrimidine (12) and imine (14) were observed with o-nitrobenzaldehyde. Para-nitrobenzaldehyde produced a quantitative yield of hexahydropyrimidine (15). The major driving force towards hexahydropyrimidine (6) formation appears to be electronic (and depends upon electron deficiency at the imine carbon), and steric congestion (compare o-nitro with p-nitro benzaldehyde) around the site of the ring cyclization is a factor. Ease of formation of hexahydropyrimidine rings with various aryl aldehydes decreases in the following order: p-nitrobenzaldehyde=2-formylpyridine>o-nitrobenzaldehyde>benzaldehyde>o-hydroxybenzaldehyde.

Effects of steric congestion and ring size on the cyclization reaction were also examined by using various N-substituted-diamines. Thus, 2-formylpyridine (2) and 1,5-diaza-octane (16) produced a quantitative yield of the hexahydropyrimidine (17) when refluxed in benzene. 1,4-Diaza-hexane (18) produced the tetrahydroimidazole derivative (19). However, use of N,N-diethylethylenediamine (20) resulted in formation of imine (21).

A general route to unsymmetrically substituted polyalkylarylamines substantially free of other structures is described. 2-Formylpyridine (2) and the triamine (4) were mixed in stoichiometric amounts and then heated in benzene. Heating is not usually needed because some aldehydes and ketones are sufficiently reactive to generate heat of reaction. Heating is used to speed up the reaction. Proton NMR analysis of the product indicated virtually complete formation of hexahydropyrimidine (22), which was isolated and characterized by mass spectrometry and by $^1H$ and $^{13}C$ NMR spectroscopy. Addition of a second mole of arylaldehyde (in one case, 2-formyl-5-methylpyridine (23)) produced a near quantiative yield of the unsymmetrically substituted hexahydropyrimidine-imine (24). Sodium borohydride reduction, followed by acidification, produced the required unsymmmmetrical pentaamine (25), which was fully characterized as its pentahydrochloride salt.

1,4,7-Triazaheptane (26) and two aldehydes (2) and (23), in that order and after reduction and acidification produced a high yield of the penta-amine pentahydrochloride (27). When the hexahydropyrimidine intermediate (22) was treated with 1-benzyl-2-formylimidazole (28), the unsymmetrical product (29) was obtained after reduction with sodium borohydride and acidification.

Use of 2,6-diformylpyridine (30) and two mole equivalents of 1,3-propanediamine produced the bis-hexahydropyrimidine (31) in quantitative yield. Reduction gave the epyden compound (32) in high yield. When 1,4,7-triazaheptane (26) was treated individually with the imidazole aldehydes (33) and (34), the unsymmetrical ligand (35) was obtained in good yield. Likewise, compound obtained from compound (34) and compound (2).

When 1,4,9-triaza-nonane (37) was used with compound (2) NMR evidence suggested that a 50:50 mixture of the two possible intermediates (38) and (39) was obtained.

The unsymmetrical chelates were mixed with cobalt ion, e.g. cobalt acetates as described herein. The color of the aqueous soltion when mixed with air changed from a clar light yellow to a clear dark brown confirming oxygen binding. The unsymmetrical chelate - metal complexes were at least as effective in binding oxygen as the symmetrical chelates.

Preferably $R^1$ and $R^2$ are each aromatic nitrogen containing compounds as described herein and are not identical.

In separate embodiments a and b are each O.

Preferably d and q are each 1 or 2;

Preferably in steps (a) and (b), the organic solvent is heated to remove water, e.g., as an azeotrope;

In one preferred embodiment, in step (a), $R^1$ is an aromatic compound and $R^3$ is —H.

In one preferred embodiment, preferably in step (b), $R^2$ is an aromatic compound, and $R^4$ is —H.

More preferably, $R^1$ and $R^2$ are each independently different aromatic groups having at least one nitrogen atom and $R^3$ and $R^4$ are each hydrogen.

Certain provisos may be present to exclude compounds of the art for $R_1$, $R_2$, $R^1$, $R^2$, $R^3$, $R^4$, a, b, d, q, m, n, o or p.

Compounds which are produced by and are a part of the present invention include, but are not limited to:

| $R^1$ | $R^3$ | $R^2$ | $R^4$ | a | b | d | q |
|---|---|---|---|---|---|---|---|
| 2-pyridyl | CH₃ | 5-methyl-2-pyridyl | H | 0 | 0 | 1 | 1 |
|  |  |  |  | 0 | 0 | 2 | 2 |
|  |  |  |  | 0 | 0 | 3 | 3 |
|  |  |  |  | 0 | 0 | 4 | 4 |
|  |  |  |  | 0 | 0 | 5 | 5 |
| 2-pyridyl | H | 5-methyl-2-pyridyl | H | 0 | 0 | 1 | 1 |
|  |  |  |  | 0 | 0 | 2 | 2 |
|  |  |  |  | 0 | 0 | 3 | 3 |
|  |  |  |  | 0 | 0 | 4 | 4 |
|  |  |  |  | 0 | 0 | 5 | 5 |
| 6-methyl-2-pyridyl | CH₃ | 2-pyridyl | CH₃ | 0 | 0 | 1 | 1 |
|  |  |  |  | 0 | 0 | 2 | 2 |
|  |  |  |  | 0 | 0 | 3 | 3 |
|  |  |  |  | 0 | 0 | 4 | 4 |
|  |  |  |  | 0 | 0 | 5 | 5 |

-continued

| R¹ | R³ | R² | R⁴ | a | b | d | q |
|---|---|---|---|---|---|---|---|
| 2-pyridyl | H | 2-(1H-imidazolyl) | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-pyridyl | CH₃ | 2-(1H-imidazolyl) | CH₃ | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-quinolyl | H | 4-methyl-2-quinolyl | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-quinolyl | H | 2-pyridyl | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-quinolyl | H | 2-(1H-imidazolyl) | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 6-methyl-2-pyridyl | H | 2-(1H-imidazolyl) | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-pyridyl | H | 4-methyl-2-(1H-imidazolyl) | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-pyridyl | H | 2-(1-benzyl-imidazolyl) | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 6-methyl-2-pyridyl | H | 4-methyl-2-(1-benzyl-imidazolyl) | H | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |
| 2-quinolyl | H | 2-(1-benzyl-imidazolyl) | CH₃ | 0 | 0 | 1 | 1 |
| | | | | 0 | 0 | 2 | 2 |
| | | | | 0 | 0 | 3 | 3 |
| | | | | 0 | 0 | 4 | 4 |
| | | | | 0 | 0 | 5 | 5 |

Unsymmetrical Chelates—The following Examples for the unsymmetrical chelates are presented for the purpose of further explaining and describing the present invention. They are not to be construed as being limiting in any way.

General—Mass spectra were obtained on a VG Analytical ZAB-HS instrument (70 eV, EI, mass reference perfluorokerosene). Proton NMR spectra ($^1$HNMR) were obtained in DCCl$_3$ or in D$_2$O either 90 MHz (Varian EM390) or 300 MHZ (GE QE300) with chemical shifts reported in ppm relative to internal standards of tetramethylsilane (0 ppm, 90 MHz spectra) or chloroform (7.258 ppm, 300 MHz) Elemental analyses were performed at the Microchemical Analysis Laboratory, University of California, Berkeley, Calif. Reactions were monitored using thin-layer chromatography (TLC) using commercially available Eastman-Kodak 13181 (100 micrometers thick) silica sheets.

EXAMPLE 1

1-(2-PYRIDYL)-11-(2-[6-METHYLPYRIDYL])-2,6-10-TRIAZAUNDECANE (25)

To a stirred solution of 3,3'-diaminopropylamine (4) (0.656 g., 0.005 mol) in dry benzene (40 mL) was added pyridine 2-carboxaldehyde (2) (0.535 g., 0.005 mol) in dry benzene (5 mL) drop wise at ambient temperature. Resulting cloudy solution was heated to reflux using a Dean-Stark trap. After 2 hr of azeotroping, the solvent was completely distilled off to produce the hexahydropyrimidine intermediate (22) (N—CH(2-pyr)—N at 4.1 ppm in $^1$H NMR spectrum). To the stirred solution of (22) in dry benzene at room temperature was added dropwise 2-formyl-6-methylpyridine (23) (0.605 g, 0.005 mol) in dry benzene (5 mL) and the mixture was refluxed using a Dean Stark trap for 2 hr. The solvent was evaporated to give the hexahydropyrimidine imine (24). The imine was dissolved in absolute ethanol (30 mL) and cooled to 0° C. before addition of NaBH$_4$ (200 mg) and stirring at 0° C. under nitrogen for 2 hr. The temperature was slowly raised to room temperature over 2 hr before being cooled once again to 0° C. and addition to dilute acetic acid to pH about 6. The mixture was then basified with saturated aqueous sodium carbonate and extracted with dichloromethane (3×25 mL). The combined organic layers were washed with water until aqueous washings were neutral and then dried over Na$_2$SO$_4$ (anhydrous). The solvent was evaporated to give a crude product which was purified by silica gel column chromagraphy (elution with 10% NH$_4$OH/MeOH) to give 1.05 g of unsymmetrical compound (25). The compound was dissolved in dry ethanol, cooled, and saturated with dry HCl gas until precipitation ceased. The white precipitate was filtered off, washed with absolute ethanol, and recrystallized from aqueous ethanol (90%) and dried at 50° C. under vacuum.

Analysis: Calculated for C$_{19}$H$_{29}$N$_5$.5HCl: C, 44.76; H, 6.72; N, 13.74. Found: C, 44.66; H, 7.07: N, 13.13%

EXAMPLE 2

1-(2-PYRIDYL)-9-(2-[6-METHYLPYRIDYL])-2,5,8-TRIAZANONANE, (27)

This compound was synthesized in the same manner as described in Example 1 by using 1,4,7-triazaheptane (26) (0.515 g; 0.005 mol) and the two aldehydes (2) and (23) in that order. After reduction in using (NaBH$_4$ in ethanol), the product was purified by silica gel column chromatography as described above, and produced 1.01 g of (27). The crude product was dissolved in dry ethanol, and the hydrochloride salt was prepared as described above.

Analysis: Calculated for C$_{17}$H$_{25}$N$_5$. 5HCl. H$_2$O C, 40.86; H, 6.45; N, 14.01. Found: C, 41.33; H, 6.35; N, 13.94%.

EXAMPLE 3

1-[2-(-BENZYLIMIDAZOLYL)]-11-2-PYRIDYL)-2,6,10-TRIAZAUNDECANE, (29)

This compound was synthesized in the same manner a described in Example 1, but using 1,5,9-triazaheptane (4) (0.656g; 0.005 mol) and the two aldehydes (2) (0.535 g, 0.005 mol) and (28) (0.93 g. 0.005 mol) in that order. After reduction using NaBH$_4$ and ethanol, the product was purified by silica gel column chromatography, as described) and gave 1.16 g of (29). The product was dissolved in dry ethanol, and the hydrochloride salt was prepared as described above.

Analysis: Calculated for C$_{23}$H$_{23}$N$_6$.5HCl. 0.5H$_2$O: C, 47.30; H, 6.51; N, 13.93 Found: C, 47.49; H, 7.30; N, 14.39%.

EXAMPLE 4

1-(2-PYRIDYL)-11-(2-IMIDAZOLYL)-2,6,10-TRIAZAUNDECANE, (35)

To a stirred solution of 3,3'-diaminodipropylamine (4) (0.655 g. 0.005 mol) in dry ethanol (40 mL) was added dropwise pyridine-2-carboxaldehyde (2) (0.535 g. 0.005 mol) in dry ethanol (5 mL). The mixture was heated at reflux for 30 min and then cooled. To the resulting hexahydropyrimidine intermediate (22) in ethanol was slowly added imidazole-2-carboxaldehyde (33) (0.48 g, 0.005 mL), and the mixture was heated at reflux for 1 hr to afford the hexahydropyrimidine imine. The mixture was then hydrogenated at ambient temperature over 5% palladized charcoal (0.8 g) at ambient pressure. After the calculated amount of hydrogen was taken up, the catalyst was filtered off and the solvent evaporated. The unsymmetrical amine (35) was purified by silica gel column chromatography (as described above), and the 0.74 g of pure compound was obtained. The product was dissolved in ethanol and the hydrochloride salt was obtained as described above in Example 1.

EXAMPLE 5

1-(2-PYRIDYL)-11-(4-IMIDAZOLYL)-2,6,10-TRIAZAUNDECANE, (36)

This compound was synthesized as described in Example 4 by using 3,3'-diaminodipropylamine (4) (0.655 g, 0.005 mol) in dry ethanol and the two aldehydes pyridine-2-carboxaldehyde (2) (0.535 g, 0.005 mol) and imidazole-4-carboxaldehyde (34) (0.48 g, 0.005 mol) in that order. After catalytic hydrogenation and purification by silica gel column chromatography, the pure free base (36) was obtained (0.79 g). The product was transformed into the hydrochloride salt as described in Ex: 4

Analysis: Calculated for C$_{16}$H$_{26}$N$_6$.4HCl. H$_2$O: C, 41.20; H, 6,86; N, 18.02; Cl, 30.47. Found: C, 41.30; H, 6.63; N, 18.14; Cl, 30.74%.

EXAMPLE 6

N-PROPYL-2-(2-PYRIDYL)-HEXAHYDROPYRIMIDINE, (17)

To a stirred solution of 1,5-diazaoctane (16) (0.58 g, 0.005 mol) in dry benzene (20 mL) was added dropwise pyridine-2-carboxaldehyde (0.535 g, 0.005 mol) in dry benzene (10 mL). The resulting solution was refluxed for 2 hr using a Dean-Stark trap to remove water. Finally, the solvent was removed completely by distillation to give compound (17) in quantitative yield (1.0 g).

The other reactions with pyridine-2-carboxaldehyde amines (18) and (20) were carried out in a similar fashion.

EXAMPLE 7

2-(2-PYRIDYL)-HEXAHYDROPYRIMIDINE, (9)

To a stirred solution of 1,3-propanediamine (0.37 g, 0.005 mol) in dry benzene (25) mL) was added dropwise at room temperature pyridine-2-carboxaldehyde (2) (0.535 g. 0.005 mol) in dry benzene (5 mL). The resulting cloudy solution was heated under reflux, using a Dean-Stark trap to remove water during 2 hr. The solvent was then completely removed by distillation to give about a quantatitive yield (0.80 g) of compound (9), having an N—C$\underline{H}$(2-pyr)—N resonance at 4.1 ppm).

The other reactions shown in Table I were carried out in the same manner, and the relative proportions of imine and hexahydropyrimidine compounds were calculated on the basis of proton NMR integrations of the reaction products.

$$PAA + Co^{2+} = Co(PAA)^{2+} \quad (1)$$

$$Co(PAA)^{2+} + H^+ = Co(PAAH)^{3+} \quad (2)$$

$$Co(PAA)^{2+} + O_2 = Co(PAA)(O_2)^{2+} \quad (3)$$

$$Co(PAA)(O_2)^{2+} + Co(PAA)^{2+} = [Co(PAA)]_2 O_2^{4+} \quad (4)$$

$$2\,Co(PAA)^{2+} + O_2 = [Co(PAa)]_2 O_2^{4+} \quad (5)$$

Reactions (1) and (2) are characterized by the equilibrium constants $K_{ML}$ and $K_{MLH}$, given by:

$$K_{ML} = [Co\,(PAA)^{2+}]/[PAA]\,[Co^{2+}] \quad (6)$$

and $$K_{MLH} = [Co(PAAH)^{3+}]/[Co(PAA)^{2+}]\,[H+] \quad (7)$$

For the carrier compounds according to the present invention, usually only the dimeric oxygen complex is observed in solution, so that the equilibrium between oxygen and carrier compound is effectively characterized by $K_{app.O2}$ given by:

$$K_{app.O2} = [(Co(PAA)]_2 O_2^{4+}]/[Co(PAA)^{2+}]^2[O_2] \quad (8)$$

In addition, each of the ligating nitrogen atoms of the polyalkylamines can be protonated (at increasingly acidic pH):

$$PAA + nH^+ = PAA(H^+)_n \quad (9)$$

the equilibrium constants for successive protonations of the PAA compounds are defined by $$K_{Hi} = [PAA(H^+)_i]/[PAA(H^+)_{i-1}]\,[H+] \quad (10)$$

Each of the above disclosed carrier compounds will be useful in the electrochemical extraction, transport, and generation of oxygen and other small ligands according to the methods of the present invention. However, the selection of particular carrier compounds according to the invention for optimization of the practice of the methodology and processes depends on a variety of factors. Further, the carrier compound preferred for a particular apparatus and process will depend on the characteristics and operating environment of the apparatus and associated power supplies and sources, fluid media used to supply ligand, the intended use of the extracted ligand, and other considerations. Generally, the characterization of carrier compounds and selection of particular carrier compounds entail several levels of experimentation, which will now be described. Although the following will make particular reference to oxygen binding to cobalt complexes of particular polyalkylamines, it is understood that the invention is not so limited.

UV—Visible Spectroscopy

Initially, solutions of particular carrier compounds are monitored by UV-visible spectroscopy to determine whether the carrier compound forms oxygen complexes of sufficient stability as to be potentially useful in processes according to the present invention. UV-visible spectra of carrier compounds are also observed as a function of the pH to determine the pH range, if any, over which the carrier compounds bind oxygen without decomposition. The initial pH for use in further experiments (the "Working pH") is defined as one pH unit above that at which the proportion of carrier compound-oxygen complex is about 90% or more of the maximum formed under ca. 0.2 atm oxygen, as determined by this spectroscopic examination. At this working PH, the formation of oxygen complex of cobalt carrier compounds, when the cobalt carrier compound is exposed to molecular oxygen, is heavily favored. In addition, the pH is generally low enough at the working pH to avoid decomposition of the particular carrier compound or spontaneous oxidation of the cobalt ion. This working pH is an initial estimate of a pH for the carrier fluids and practice of the methods of the invention. Experimentation involving varying the pH of the carrier fluids may indicate a more efficacious pH for actual use in the methods. Usually, the pH will be chosen such that at least half of the maximal concentration of carrier compound-oxygen complex is formed; more usually, the pH is selected so that at least 75% of the maximal concentration is formed, and preferably the pH is selected so that 90% or more of the maximal proportion of oxygen complex is present, all under a pressure or partial pressure of ca. 0.2 atm oxygen. An initial working pH can also be determined from potentiometric experiments on the oxygen complexes of cobalt carrier compounds, as will be discussed below.

1. Procedure

The necessary UV and visible spectra necessary for this evaluation are obtained with any of a variety of commercially available spectrophotometers. The solution to be measured is prepared in or transferred to a suitable quartz cell with provision for the exclusion of oxygen. This solution contains the cobalt carrier compound of interest in a concentration calculated to yield a level of absorbance at, e.g., 330 nm, commensurate with the range of the particular instrument in use, and will be appropriately buffered or otherwise adjusted to the desired pH. Spectra are then recorded under both oxygen free and oxygenated conditions at each of the desired pH values.

2. Results

Typical results from the spectrophotometric evaluation of cobalt carrier compounds are shown in FIG. 1. Generally, with increasing pH, an increasingly greater proportion of the cobalt complex is present as the oxygen complex, which is identified by a characteristic absorbance maximum (for cobalt complexes of the type of interest here) at about 330 nm. As the pH is increased further, a decrease in absorbance at this wavelength is observed, indicating a decreasing amount of the oxygen complex of interest due to, most likely, decomposition of the carrier compound, oxidation of the metal ion such that oxygen binding no longer occurs, or other reasons. For example, the Co(II) complex of PAA No. 21, abbreviated in the literature as DMPAP, has been determined to be relatively unsatisfactory for use in the molecular oxygen extraction and generation processes of the invention due to relatively rapid, irreversible oxidation of the cobalt ion to Co(III), which does not bind oxygen. From the results of such spectrophotometric analysis, the cobalt complex of PAA No. 76 does not appear to bind oxygen under conditions of interest here.

Potentiometric Experiments

Where spectrophotometric characterization of a particular cobalt carrier compound has proven satisfactory, both the polyalkylamine and the cobalt carrier compound are characterized by a set of potentiometric pH titrations to determine the basicity of the ligating atoms, the formation constants $K_{ML}$ and $K_{MLH}$, and the apparent oxygen binding equilibrium constants.

1. Procedure

Potentiometric titrations are performed using a Fisher or Cole-Palmer pH meter in a sealed, jacketed glass cell equipped with glass and calomel electrodes and with provisions for performing measurements under oxygen-free conditions. The cell is kept at a constant temperature of 25°±0.1° C. by circulating water from a thermostated bath through the cell jacket. The electrodes and pH meter are standardized with commercially available standard buffer solutions (Fisher Scientific). The polyalkylamine ligands and cobalt carrier compounds were each titrated potentiometrically by incrementally adding standard potassium hydroxide solution and recording the pH of the solution after each addition of base. Titrations of the cobalt carrier compounds are carried out under prepurified nitrogen or argon; titrations of oxygenated carrier compounds are performed under oxygen treated with Ascarite to remove carbon dioxide.

All solutions contained ca. 1.5 mM PAA; for titrations of cobalt complexes, the solutions contained, in addition, 1.5 mM $CoCl_2$.

2. Results

Typical results obtained as outlined above from pH titrations of selected polyalkylamines, cobalt carrier compounds, and oxygen complexes of cobalt carrier compounds are graphically depicted in FIGS. 2, 3, and 4, and summarized in Table III. The values shown in Table III, defined by equations (6)–(8) and (10). above, were derived either by direct measurement from the titration curves obtained, or determined by the iterative best fit of the data to a computer program such as that described by Harris, et al., *Inorganic Chemistry*, vol. 17, p. 889, 890 (1978). Generally, although the latter values are considered to be more reliable, values obtained by either methods are approximately the same and sufficient for the present evaluation.

TABLE III

POLYALKYLAMINE BASICITY AND BINDING TO COBALT

| PAA NO. | Log $K_1$ | Log $K_2$ | Log $K_3$ | Log $K_4$ | Log $K_5$ | Log $K_{MLH}$ | Log $K_{ML}$ | Log $K_{O2}$ | Ref. |
|---|---|---|---|---|---|---|---|---|---|
| 21 | 7.55 | 6.86 | 3.2 | 2.9 | — | — | 14.8 | * | 2 |
| 21 | 7.74 | 6.69 | 2.95 | — | — | — | — | — | 3 |
| 33 | 9.85 | 9.27 | 8.19 | 5.08 | 3.43 | 5.40 | 13.66 | 15.83 | 1 |
| 62 | 8.88 | 7.04 | 3.82 | 1.44 | — | 2.28 | 14.73 | 11.4 | 1 |
| 62 | 8.91 | 6.95 | 3.64 | — | — | — | — | — | 3 |
| 63 | 8.75 | 7.61 | 3.81 | — | — | — | — | — | 3 |
| 64 | 9.92 | 7.63 | 6.76 | 1.79 | — | 4.42 | 11.47 | 7.7 | 1 |
| 64 | 9.54 | 7.44 | 6.34 | — | — | — | — | — | 3 |
| 69 | 9.31 | 8.6 | 5.9 | 4.74 | — | — | — | — | 3 |
| 72 | 8.6 | 6.75 | 4.76 | — | — | — | — | — | 3 |
| 73 | 9.76 | 7.22 | 6.51 | 3.92 | 3.29 | — | 11.55 | 8.63 | 4 |
| 74 | 10.12 | 8.62 | 7.36 | 4.51 | 3.82 | 3.99 | 11.36 | 9.49 | 4 |
| 74 | 9.75 | 8.58 | 7.2 | 4.75 | 3.75 | — | — | — | 3 |
| 75 | 9.22 | 8.18 | 4.91 | 3.90 | 2.92 | 3.33 | 13.84 | — | 4 |
| 75 | 9.15 | 8.03 | 4.92 | 3.91 | — | — | — | — | 3 |
| 76 | 9.15 | 7.20 | 5.79 | 3.40 | — | — | — | — | 3 |
| 78 | 9.36 | 7.69 | 6.60 | — | — | — | — | — | 3 |
| 80 | 8.52 | 6.72 | 4.1 | 3.28 | 2.86 | — | — | — | 3 |
| 81 | 9.44 | 7.40 | 6.25 | 3.40 | — | — | — | — | 3 |

References:
1. Harris, et al., Inorganic Chemistry, vol. 17, 889–94 (1978);
2. Gruenwedel, Inorganic Chemistry, vol. 7, 495–501 (1968);
3. determined by applicants
4. Timmons, et al., Inorganic Chemistry, vol. 17, 2192–97 (1978)

Notes:
*Oxygen complex is unstable.
**No oxygen complex observed.

An appropriate "Working pH" can also be derived from the potentiometric titration data obtained with the oxygenated $Co(PAA)^{n+}$ complexes. The working pH is, as described above, the pH at which 90% or more of the cobalt carrier compound is present in solution as the oxygen complex, and is about one pH unit greater than the apparent $pK_a$ obtained from the potentiometric titration curve (the pH at the midpoint of the pH titration). FIG. 5 graphically depicts the working pH values obtained in this way for several cobalt carrier compounds, along with the pH values for the endpoints of the titrations of the unoxygenated and oxygenated cobalt carrier compounds.

From the $K_{O2}$ values, the change in the free energy for the oxygenation of the cobalt carrier compounds and thus the minimum power requirements for the electrochemical release of oxygen can be calculated. For the overall equilibrium given by equation (5) above, the standard free energy in calories/mole is given by $$\Delta G° = -RT \ln K_{O_2} = -nFE°_{O_2} \quad (11)$$

where:

T is the temperature in Kelvins; R is a constant of 1.987 cal/mole - K; F is 96,487 C/mole; $K_{O_2}$ is given by equation (8); and $E°_{O_2}$ is the standard potential for the reaction of equation (5). For a two-electron process (n=2), RT/nF=0.01285 V. For a non-standard states (i.e. where the chemical activities of the species in solution are not equal to one):

$$\Delta G = \Delta G° + RT \ln Q \quad (12)$$

and $$E_{O_2} = E°_{O_2} - RT/nF \ln Q = 0.01285 \ln(K_{O_2}/Q) \quad (13)$$

where the concentrations actually present in solution are used to calculate Q from $$Q = [Co(PAA))_2 O_2]/[Co(PAA)]^2 [O_2] \quad (14)$$

Assuming the total carrier compound concentration is initially 0.1 mole/liter, that half of the cobalt ion is oxidized electrochemically to release oxygen, and that the resulting concentration of oxygen (in solution) is 1.4 mM, for the carrier compound equilibrium of equation (5), $$Q = (0.25x)/(A - 0.5x)^2 [O_2] \quad (15)$$

where A is the initial carrier compound concentration and x is A times the percentage of carrier compound which is present as the oxygen complex, the minimum voltage, E, for the process can be determined. If the total oxygen to be released is 1L/min, the total current, I, required is 71.8 n amperes, where n is the number of electrons per oxygen released, and the minimum power, in Watts, required is given by P−71.8 n E. This is the minimum power required, and neglects such factors are parasitic power losses due to the resistance of the carrier fluid. Calculations of the voltage and power required for various dimeric cobalt carrier compounds indicate required cell voltages between about 100 and about 400 mV and power requirements of between about 15 W/L and about 50 W/L of $O_2$ released per minute.

Electrochemical Experiments

Further characterization by cyclic voltammetry and coulometry is performed for those cobalt carrier compounds that exhibit suitable oxygen binding properties and the identification of cobalt carrier compounds for which electrical operating parameters, such as the voltage and current requirements of apparatus for practicing the methods of the present invention, would be most convenient with minimum actual power consumption.

1. Procedures

Cyclic voltammentry experiments were performed under nitrogen or iar for the unoxygenated or oxygenated carrier compounds, respectively, in a cell having a platinum wire auxiliary electrode, a silver-silver chloride reference electrode, and suitable working electrode. The potential between the auxiliary and working electrodes was varied with a Princeton Applied Research (Princeton, N.J.) Scanning Potentiostate at 50 mV/s from a suitable initial with a suitable initial scan direction (Scan Dir.), depending on the electrochemical potentials if interest. All solutions contained 1 mM $CoCl_2$, 1 mM or 1.5 mM PAA, and a supporting electrolyte, and were buffered to a suitable pH, usually about the initial working pH.

Cyclic voltammetry enables the estimation of anode ($E_{PA}$) and cathode ($E_{PC}$) half cell potentials, the cell potential $\Delta E = (E_{PA} - E_{PC})$, and an approximate formal reaction potential $E° = (E_{PA} - E_{PC})/2$. In addition, estimates of the rate of electron transfer to a particular electrode and electrochemical reversibility of the reaction can be obtained. However, cyclic voltammetry experiments do not show whether or not to what extent molecular oxygen is released.

Coulometry techniques allow the determination of the relative energetics and rates of oxygen release. For such experiments, solutions similarly to those outlined above for cyclic voltammetry are placed in a three-electrode electrolysis cell equipped with a Clark-type oxygen probe. The carrier compound is electrochemically reduced, oxygenated, and then reoxidized by the application of a series of existing potentials. Each oxidizing potential is held constant with respect to a silver-silver chloride reference electrode. The resulting current is integrated over time to yield the amount of carrier compounded oxidized. By employing the same electrode geometry, solution volume, stirring rate, information about the relative rate and amount of oxygen release (the "$O_2$ rate") can be determined, at a particular applied cell voltage. $E_{app}$ from the response of the oxygen probe.

The expected amount of oxygen evolved is given one-half the total integrated charge through the cell divided by F=96,484 C/mole, since theoretically, two electrons are required to oxidize the two cobalt ions and release one oxygen molecule. The ratio of this figure to the actual amount of oxygen produced is "% $O_2$ max", at the minimum voltage, $V_{min}$, required to produce oxygen. In additional, the "voltage window" the difference between the anodic oxygen evolution and cathodic reduction potentials is measured.

2. Results

A typical cyclic voltammetry trace, for the oxygenated Co(II) complex of PAA No. 72 using a glassy carbon electrode, is shown in FIG. 6. Results for several cobalt carrier compounds are summarized in Table IV. Coulometry data for several cobalt carrier compounds is summarized in Table V. The couliometric data reported on the average of three to five experiments. The standard deviations for $O_2$ rate were +/=0.36 microliters per minute.

TABLE IV

| | | | | | | | | | | | |
|---|---|---|---|---|---|---|---|---|---|---|---|
| SUMMARY OF CYCLIC VOLTAMMTRY DATA OF Co(PAA)$^{n+}$ CARRIER COMPOUNDS | | | | | | | | | | | |
| PAA NO. | [PAA], mM | pH | Buffer | Type | Electrode | $E_{initial}$, V | Scan Dir. | $E°$, V | $\Delta E$, V | $E_{PA}$, V | $E_{PC}$, V |
| 33 | 1.5 | 9.0 | 1 | deox | C | −0.3 | + | −0.39 | 0.12 | −0.33 | −0.45 |
| 33 | 1.5 | 9.0 | 1 | ox | C | −0.3 | + | * | 1.2 | 0.7 | −0.5 |
| 62 | 1.5 | 3.0 | 2 | deox | G | −0.3 | + | −0.05 | 0.1 | 0.0 | −0.1 |
| 62 | 1.0 | 9.0 | 3 | ox | G | +0.12 | + | * | 1.3 | 0.75 | −0.55 |

TABLE IV-continued

SUMMARY OF CYCLIC VOLTAMMTRY DATA OF Co(PAA)$^{n+}$ CARRIER COMPOUNDS

| PAA NO. | [PAA], mM | pH | Buffer | Type | Electrode | $E_{initial}$, V | Scan Dir. | $E^o$, V | $\Delta E$, V | $E_{PA}$, V | $E_{PC}$, V |
|---|---|---|---|---|---|---|---|---|---|---|---|
| 64 | 1.0 | 7.6 | 4 | deox | G | −0.3 | + | −0.05 | 0.85 | 0.4 | −0.45 |
| 64 | 1.0 | 7.6 | 2 | ox | G | +0.3 | + | * | 1.2 | 0.08 | −0.4 |
| 72 | 1.0 | 5.93 | 2 | deox | C | +0.1 | + | −0.02 | 0.11 | 0.03 | 0.66 |
| 72 | 1.0 | 5.93 | 2 | ox | C | +0.1 | + | * | 0.73 | 0.66 | −0.07 |
| 78 | 1.0 | 10.1 | 2 | deox | C | +0.15 | − | 0.14 | 0.08 | 0.18 | 0.1 |
| 78 | 1.0 | 10.1 | 2 | ox | C | +0.1 | + | 0.12 | 0.13 | 0.185 | 0.055 |
| 69 | 1.0 | 3.0 | 2 | ox | C | −0.05 | + | * | 0.7 | 0.5 | −0.2 |
| 63 | 1.0 | 6.0 | 2 | ox | C | +0.1 | + | * | N.O. | N.O. | N.O. |
| 76 | 1.0 | 12.0 | 2 | ox | C | +0.19 | − | * | 0.6 | 0.25 | −0.35 |

[PAA] = Polyalkylmine concentration, milliMoles/L
Buffer: 1 = 0.5M NaCl, 0.1M Borate
2 = 0.5M KCl, 0.1M K$_2$HPO$_4$
3 = 0.5M NaCl, 0.1M Borate
4 = 0.5M NaCl, 0.1M K$_2$HPO$_4$
Type: deox = unoxygenated carrier compound
ox = oxygenated carrier compound
$E_{initial}$: volts v. Ag/AgCl reference electrode.
Electrode: C = glassy carbon electrode
G = gold
N.O. = not observed due to low electrochemical activity.
*Cyclic voltammetry does not provide an accurate $E^o$ value for oxygenated complexes; spectroelectrochemical or potentiometric methods are preferred.

TABLE V

COULOMETRY DATA FOR SELECTED COBALT PAA CARRIER COMPOUNDS

| PAA No. | $E_{App}$, V | O$_2$ Rate (μl/min) | % O$_2$ max | $V_{min}$ | Voltage Window |
|---|---|---|---|---|---|
| 33 | 0.55 | 3.5 ± 0.1 | 50 | 0.5 | 0.75 |
| 62 | 0.70 | 1.4 ± 0.1 | NA* | NA | 0.80 |
| 64 | 0.70 | 1.5 ± 0.2 | 42 | 0.5 | 0.60 |
| 72 | 0.75 | 2.3 ± 0.5 | NA | NA | 0.80 |
| 73 | 0.70 | 0.7 ± 0.2 | 31 | 0.5 | 0.65 |
| 74 | 0.70 | 1.5 ± 0.3 | NA | NA | 0.80 |
| 75 | 0.70 | 1.5 ± 0.4 | 28 | 0.6 | 0.75 |
| 78 | 0.50 | 0.8 ± 0.2 | 16 | 0.2 | 0.55 |
| 118 | 0.80 | 1.6 ± 0.2 | 20 | 0.4 | 0.50 |
| 119 | 0.65 | 1.4 ± 0.3 | NA | NA | 0.65 |
| 121 | 0.75 | 1.4 ± 0.2 | 28 | 0.6 | 0.75 |
| 180 | 0.60 | 4.1 ± 0.5 | 52 | 0.5 | 0.60 |
| 189 | 0.70 | 0.7 ± 0.4 | NA | NA | 0.70 |
| 190 | 0.70 | 1.4 ± 1.2 | NA | NA | 0.90 |
| 191 | 0.60 | 5.8 ± 0.8 | 49 | 0.5 | 0.62 |
| 192 | 0.70 | 7.7 ± 1.1 | NA | NA | 0.75 |

*NA = not available

FIG. 7 shows in schematic form the operation of an idealized apparatus for use in accordance with the process of the present invention in combination with an oxygen loading device of unspecified character. Oxygen is presumed to be the ligand in this illustration. The essential characteristics of the apparatus of the invention include a container 1 which communicates with an external environment 2 from which oxygen is to be extracted through a gas-rermeable membrane 3 and with an internal environment 2' into which oxygen is to be transported by means of a second gas-permeable membrane 3'. The remaining portion of the container wall in the embodiment shown is impermeable to gas, but in other embodiments is not so limited. An anode 8 is in circuit with a cathode 10 through a voltage or current source 9. Within the confines of the container 1 is a fluid 5 which contains oxygen-binding carrier compound 6 in forms 6a, 6b and 7. For purposes of illustration, the binding state is shown as a reduced oxidation state. In an oxygen loading compartment 4, oxygen becomes bound to oxygen carrier compound 6a (the reduced form of compound 6) to form a bound-oxygen complex 7. Complex 7 is transported along with the fluid 5 to a compartment 4' where oxygen is unloaded (dissociated) from the oxygen carrier compound to which it is bound by the oxidation of the reduced state oxygen carrier compound 6a to the oxidized state oxygen carrier compound 6a to the oxidized state oxygen carrier compound 6b at anode 8 to produce free oxygen carrier compound 6b. The oxygen is separated from the oxygen carrier compound, in the embodiment shown, by diffusion through gas-permeable membrane 3'. The fluid 5 containing the free oxidized oxygen carrier compound 6b is then circulated past cathode 10 where oxidized state oxygen carrier 6b is reduced to reduced state oxygen carrier compound 6a. Carrier fluid 5 containing reduced carrier compound 6a is then circulated back to compartment 4 where the process is repeated.

One apparatus for bench-scale or laboratory-scale evaluation of particular carrier compounds for use in practicing the methods according to the invention is illustrated schematically in FIG. 8. The electrochemical oxygen cell (EOC), designated 20, includes generally an oxygen loader 22, an electrochemical cell 24 having an anode compartment 26 and a cathode compartment 28 separated by an ion-permeable membrane 30, and an unloader 32. Carrier fluid is circulated through loader 22, anode compartment 26, unloader 32, cathode compartment 28 and back to loader 22 using the pump 34 with appropriate plastic or glass conduit.

The carrier fluids suitable for use in, for example, electrochemical oxygen cell 20 comprise a carrier compound in a concentration between about 1 mM and 500 mM, usually between about 10 mM and 300 mM, usually between about 50 mM and about 200 mM. Carrier fluids comprising carrier compounds according to the present invention are preferably aqueous and include additional an electrolyte, e.g., sodium chloride, potassium chloride, sodium nitrate, potassium sulfate, at a concentration of between about 0.1M (moles/liter) and about 1.0M usually about 0.5M. The carrier fluids may be titrated or buffered to the desired pH. Buffer salts such as sodium borate, potassium phosphate, sodium phosphate, etc., may be used depending upon the pH desired, the availability of particular salts, and compatibility of particular buffer salts with particular carrier compounds. The buffer salts(s) are generally present in concentrations of between 10 mM and about 0.5M, usually between 50 mM and 100 mM.

Loader 22 is, for example a microporous hydrophobic hollow fiber membrane array such as that which will be described more fully below in connection with FIG. 9. Suitable membrane arrays are manufactured by Bard Cardiosurgery. Inc. of Concord, Calif. These membrane arrays are typically modified to allow fluid flow both inside and outside the hollow fibers in a manner that will be apparent to those skilled in the art.

Cell 24 includes a pair of titanium current collector plates 36, 38, which press against two electrodes 40, 42. Typically, electrodes 40, 42 are carbon felt electrodes, in one example of the cell 24 having dimensions of about 25 cm $\times$ 10 cm. $\times$ 0.5 cm. Electrodes 40, 42, and thus anode compartment 26 is cathode compartment 28, are separated by membrane 30 which is an ion-permeable membrane made, for example, of Nafion (sold by DuPont). Cell 24 is assembled in a plexiglass housing (not separately shown) having two halves which are bolted together and sealed with an O-ring or gasket seal (not shown). Cell 24 includes the necessary ports for introducing and removing carrier fluids from anode compartment 26 cathode compartment 28. Cell 24 further includes ports for insertion of reference electrodes 44, 46 which are conveniently, but not necessarily silver-silver chloride reference electrodes. Current collector plates 36, 38 are connected via titanium posts 48, 50 to a potentiostat (not shown) capable of supplying either a constant or a variable current or voltable to cell 24. Suitable potentiostats are available for example, from Princeton Applied Research, Princeton, N.J. Unloader 32, in the embodiment shown in FIG. 8 includes a cylindrical fluid gas separation chamber 52, equipped with a nitrogen sweep gas bubbler 54 near the bottom thereof and an exit port at the top thereof. Alternatively, unloader 32 may be a hollow fiber device such as that described above in connection with loader 22.

In operation, carrier fluid is circulated through loader 22 where it is exposed, through the ligand-permeable membrane, to the fluid from which oxygen is to be extracted. In the typical laboratory-scale electrochemical oxygen cell 20, carrier fluid of oxygenated using air as the external fluid. The carrier fluid is circulated through anode compartment 26, where it is oxidized to dissociate bound oxygen, and then to unloader 32, where the dissociated oxygen is removed by the nitrogen sweep gas. The deoxygenated fluid is thereafter circulated through cathode compartment 28, where the carrier compound is reduced, and then back, to loader 22 for repetition of the cycle.

The concentration of oxygen present in the carrier fluid is measured at several points with oxygen probes 56, 58, 60. A flow meter (now shown) is used to measure the recirculation of the carrier fluid through electrochemical oxygen cell 20. In addition, the cathode and anode potentials are measured with respect to reference electrodes 44, 46, respectively, and the current through cell 24 is monitored by means that will be apparent to those skilled in the art. The flow rate of the sweep gas stream is monitored as is the concentration of oxygen in the sweep a gas outlet with a fourth oxygen probe 62, so that oxygen extraction and release may be quantitated. Oxygen probes 56, 58, 60, 62 are Clarke-type oxygen probes, operable to produce an electrical potential proportional to the oxygen concentration ambient to the probe. Oxygen probe 56 monitors the loading process. Probe 58 monitors the oxygen evolved in the anode compartment 26. Oxygen probe 60 is used to monitor the efficiency of the unloading process and unloader 32.

Preferably, signals from oxygen probes 56, 58, 60, 62, the flow rates of the carrier fluid in the nitrogen sweep gas, the potentials of the anode and cathode plates 48, 50 with respect to the electrodes 44 and 46, and the current through cell 24 are all simultaneously monitored, digitized, and stored in a computer for later analysis.

Typically, this data and carrier compound concentration, the carrier fluid flow rate, and the applied cell voltages are analyzed to derive the rate of oxygen production, the power consumed by cell 20, and the number of electrons flowing through cell 20 to produce one molecule of oxygen. Generally, it is preferred that power and the average number of electrons passed per molecule of oxygen produced should be minimized, while the rate of oxygen production should be maximized. Results for selected cobalt carrier compounds are given in Table IV and FIGS. 11-16. FIGS. 11, 13 and 15 give results utilizing a prior art carrier compound, cobalt dishistidine, while FIGS. 12, 14 and 16 give comparative results utilizing a carrier compound of the present invention, cobalt 1,11-bis(2-(1-methylimidazolyl))-2,5,10-triazaundecane.

TABLE VI

ELECTROCHEMICAL OXYGEN CELL RESULTS FOR COBALT CARRIER COMPOUNDS

| PAA No. | [PAA], mM | Flow*[1] (mL/min) | pH | E, V*[2] | EC $O_2$*[3] ml/min. | Power*[4] W/L/min. | $e^-/O_2$*[5] |
|---|---|---|---|---|---|---|---|
| 33 | 10 | 30 | 6 | 1.6 | 0.284 | 839 | 7.3 |
| 33 | 110 | 50 | 6 | 1.6 | 2.0 | 259 | 2.3 |
| 62 | 10 | 30 | 3 | 0.9 | 0.143 | 178 | 2.5 |
| 62 | 10 | 30 | 3 | 1.6 | 0.5 | 580 | 4.9 |
| 62 | 100 | 30 | 4 | 0.9 | 1.15 | 158 | 2.3 |
| 62 | 100 | 30 | 4 | 1.6 | 1.7 | 550 | 4.8 |
| 62 | 100 | 120 | 4 | 1.6 | 3.76 | 260 | 2.3 |
| 62 | 100 | 100 | 4 | 0.5 | 0.082 | 99.2 | 2.5 |
| 62 | 75 | 95 | 5 | 0.5 | 0.081 | 86.2 | 2.4 |
| 62 | 162 | 68 | 3 | 0.5 | 0.133 | 99.5 | 2.7 |
| 64 | 10 | 30 | 7 | 0.9 | 0.104 | 854 | 13 |
| 64 | 10 | 30 | 7 | 1.6 | 0.279 | 570 | 5.15 |
| 64 | 167 | 138 | 10.12 | 0.5 | 0.341 | 99.5 | 2.75 |
| 64 | 150 | 58 | 9.18 | 0.5 | 0.194 | 108 | 2.9 |
| 64 | 150 | 146 | 9.18 | 0.5 | 0.259 | 100 | 2.85 |
| 72 | 10 | 30 | 6.7 | 0.9 | 0.091 | 400 | 6.23 |
| 72 | 10 | 30 | 6.7 | 1.6 | 0.548 | 556 | 4.8 |
| 133 | 100 | 120 | 7 | 0.6 | 0.60 | 102 | 3.0 |
| 189 | 200 | 45 | 7 | 0.6 | 1.80 | 142 | 4.3 |
| 192 | 50 | 60 | 7 | 0.6 | 1.90 | 71 | 2.1 |

TABLE VI-continued
ELECTROCHEMICAL OXYGEN CELL RESULTS FOR COBALT CARRIER COMPOUNDS

| PAA No. | [PAA], mM | Flow*1 (mL/min) | pH | E, V*2 | EC O$_2$*3 ml/min. | Power*4 W/L/min. | e$^-$/O$_2$*5 |
|---|---|---|---|---|---|---|---|
| 192 | 100 | 50 | 7 | 0.6 | 1.20 | 66 | 2.0 |

*1 carrier fluid flow rate
*2 applied cell potential
*3 electrochemical oxygen production rate
*4 power consumed, in watts/liter of O$_2$/min
*5 electrons passed per molecule of O$_2$ produced It should be noted in connection with the operation of the apparatus shown in FIGS. 7, 8, and 9 that it may prove energetically or otherwise advantageous to "cycle" only a portion of the carrier compound during any particular oxidation and/or reduction step. That is, the necessary cell voltages and energetics may be favorably adjustable by maintaining a mixture of both oxidized state and reduced state carrier compound at all times in all portions of the apparatus, so that only a portion of the carrier compound is capable of binding or binds the oxygen during the complete cycle.

FIG. 9 shows a schematic diagram of working electrochemical cell and unloading station in combination with a pump for circulating and carrier and ligand extraction station. The apparatus shown in FIG. 9 will be referred to herein as the demonstration unit. These components together form a sealed system containing a fixed volume of ligand carrier and carrier fluid. The apparatus shown in FIG. 9 is generally of a type generally intended for relatively larger scale production of oxygen. The electrochemical cell comprises twenty parallel TEFLON ® (polytetrafluoroethylene, a trademark of the DuPont Company, Wilmington, Del.) plates having sputtered gold surfaces, between which the carrier fluid id directed, in parallel. The plates are 3 mm thick and spaced at a distance of 1 mm. An individual place is 62.5 cm long and 8 cm wide. When stacked in a parallel plate arrangement, the twenty layers have a total height of 8 cm. The use of a bipolar cell such as this enables the use of higher voltages at proportionately small currents than would be required to operate a single anode, single cathode cell of the same surface area. The electrochemical cell is connected to a voltage supply capable of providing 20 amps at 0.1 volt. The unloading station comprises one or more (one is shown) hollow fiber cartridges 1 inch in diameter and 43 inches in length containing hollow fibers which consist of porous polysulfone with an interior silicon rubber skin. The surface area of the hollow fibers is 0.25 m². When more than one such cartridge is used, they are arranged for parallel flow to a commensurate fraction of the total carrier fluid flow through the apparatus. Polyvinylchloride or polypropylene piping is used to connect various inlet and outlet ports. The outlet port of the first electrode compartment is connected to the inlet port of the small of the two hollow fiber cartridges so that the fluid which exists from the first electrode compartment enters the interior or the hollow fibers. This outlet port of the hollow fiber cartridge is connected to the inlet port of the second electrode compartment. The inlet port of the first electrode compartment is connected to the outlet port of the ligand extracting station while the outlet port of the second electrode compartment is connected through a pump to the inlet port of the ligand extracting station. In the embodiment shown, the ligand extracting station comprises one or more (one is shown) hollow fiber cartridges 3 inches in diameter and 43 inches in length, arranged for simultaneous parallel flow through the cartridges when more than one is used. Each cartridge contains 660 hollow fibers made of porous polysulfone with an interior silicon rubber skin. The hollow fibers have a membrane surface area of 2.5 m² and an interior volume of 646 ml. The space surrounding the hollow fibers is in communication with the electrochemical cell, not the interior of the hollow filbers. A fluid containing the ligand which is being extracted passes through the interior of the hollow fibers.

Operation of the demonstration unit apparatus is illustrated with the ligand carrier. Approximately 1 liter of the carrier fluid is present in the interior volume of the apparatus as described above and the ligand extracting station together. Carrier fluid containing the ligand carrier having a ligand bound thereto passes from the exit port of the ligand extracting station into the inlet port of the first electrode compartment where a redox reaction takes place in order to release the ligand carrier having a ligand bound thereto passes from the exist port of the ligand extracting station into the inlet port of the first electrode compartment where a redox reaction takes place in order to release the ligand from the ligand carrier. Free ligand, carrier fluid, and nonbinding-state ligand carrier pass from the exist port of the first electrode chamber into the ligand unloading station where ligand passes through the walls of the ligand-permeable membrane and is collected. In the particular illustration shown, oxygen passes directly in the space where it is being utilized. It is also possible to pass fluids or chemical reactants over the outside of the hollow fibers. It will of course be recognized that the ligand can be concentrated or diluted depending on the rate at which the carrier fluid is circulated. Slow circulation results in high concentrations of the ligand bound to the ligand carrier and thus released at the first electrode compartment. Carrier fluid (now depleted of ligand) and non-binding-state ligand carrier pass from the exist port of the ligand unloading station to the inlet port of the second electrode compartment where an electrochemical reaction opposite to the which occurred in the first electrode compartment takes place. This second redox reaction reforms the original binding-state ligand carrier. Binding-state ligand carrier and carrier fluid then pass from the exist port of the electrochemical cell though a gear pump to the inlet port of the ligand extracting station. In the embodiment shown as an example in FIG. 9 which may be used to extract oxygen from water and release oxygen into a second environment, water flows through the ligand (oxygen) extracting hollow fiber cartridge at a rate of 20 gallons per minute at 20 psi pressure. Circulating carrier compound in an aqueous carrier fluid (20 mM) circulates at 0.25 gallons per minute. Results obtained from tests using the demonstration unit, an apparatus similar to that shown in FIG. 9, are given in Table VII. The parameters of the operation and values obtained are defined above in connection with FIG. 8 and Table VI.

TABLE VII
DEMONSTRATION UNIT RESULTS FOR COBALT CARRIER COMPOUNDS

| PAA No. | [PAA], mM | Flow*1 (mL/min) | pH | E, V*2 | EC $O_2$*3 ml/min. | Power*4 W/L/min. | $e^-/O_2$*5 |
|---|---|---|---|---|---|---|---|
| 33 | 110 | 4000 | 8.3 | 16 | 87.5 | 808 | — |
| 33 | 52.5 | 1200 | 10.15 | 16 | 58.7 | 250 | — |
| 62 | 75 | 3380 | 5.0 | 16 | 72.4 | 285 | 2.44 |
| 62 | 75 | 3380 | 5.0 | 18 | 94.5 | 320 | 2.46 |
| 64 | 100 | 2000 | 7.0 | 4 | 20.3 | 62 | 2.42 |
| 64 | 100 | 2000 | 7.0 | 9 | 72.2 | 118 | 2.01 |

*1 carrier fluid flow rate
*2 applied cell potential (ten cell stock)
*3 electrochemical oxygen production rate
*4 power consumed, in watts/liter of $O_2$/min
*5 electrons passed per molecule of $O_2$ produced One component of an apparatus of the present invention is the ligand-permeable membrane. However, the technology relating to the production and use of ligand-permeable membranes is well known and need not be set forth here in detail. See for example, "Membrane Technology", Kirk-Othmer Encyclopedia of Chemical Technology. 3rd Ed., John Wiley and Sons, New York, Volume 15, page 92–131 and the references cited therein. Certain preferred embodiments of suitable membranes are discussed here, however, in order to exemplify the invention.

The selection of a membrane for use in the present invention is not limited other than by the ability of the membrane to pass the ligand while retarding the passage of other components of the fluid environment from which the ligand is being extracted. It will be desirable to select a membrane based on the purpose for which it will be used, e.g., use in contact with exhaust gas or extraction of a ligand from a waste liquid stream. Most important synthetic membranes are formed from organic polymers, and there are extensive tabulations of permeability coefficients for various ligand/polymer systems now in existence. See, for example van Amerongen, Rubber Chem. Technol. 37, 1065 (1964); Allen et al. J. Member. Sci. 2 153 (1977); Yasuda et al., in Bradrup et al., Eds., Polymer Handbook, Second Edition, John Wiley and Sons, New York, 1975. p. 111; and Bixlar et al., in Sweeting, Ed., The Science and Technology of Polymer Films, Vol. II, John Wiley and Sons, New York, 1971, p. 85. In addition to ligand permeability, inertness to the external fluid environment and the internal carrier fluid are also required.

The physical microstructure of the membrane is not important so long as the membrane performs the function described herein. Accordingly, dense films, porous membranes, and asymmetric and composite membranes are suitable. The macroscopic form of the membrane is also relatively unimportant, although hollow fibers are preferred over flat sheets or tubular membrane configurations since hollow fibers are self-supporting and thus eliminate the need for expensive support materials. In fact, hollow fiber cartridges in which a plurality of gas-permeable hollow fibers are connected in parallel between two manifolds at opposite ends of each tube can readily be adapted for use in the present invention. For example, Romicon manufacturers a hollow fiber cartridge 3 inches in diameter and 43 inches long containing 660 hollow fibers joined to manifolds at opposite ends of the cartridge. The hollow fibers have a surface area of 2.5 m² and volume 647 and are in the form of a polysulfone membrane coated with a silicone rubber layer over a polysulfone layer to form a composite membrane. Fluid from the environment, e.g. seawater, is transported through the inside of the hollow fibers (i.e., the interior of the fibers is the outside of the closed container) where extraction of oxygen into the fluid carrier takes place. When used to release oxygen, for example, the cartridge walls form an oxygen-collecting chamber around the hollow fibers through which the carrier fluid is transported.

When the environmental fluid from which oxygen is extracted is an aqueous fluid, a polymer having a high permeability to oxygen is particularly preferred because of the low chemical activity of oxygen in water. Silicone rubber, natural rubber, poly(phenylene oxide), and poly(trimethylsilylpropyne), often abbreviated as PMSP, have been found to form suitable membranes in such environments. When oxygen is being extracted from air, high permeability is less important. In any event, the present invention has advantages over passive diffusion systems since the partial pressure of oxygen in the carrier fluid itself if essentially zero at all times until the oxygen binging compound is saturated. Accordingly, a constant oxygen chemical activity gradient across the membrane exists in practice since the oxygen bound to the carrier compound will normally be transported to a second location where oxygen will be unloaded prior to saturation.

Another material of interest is porous polysulfone in the form of hollow fibers having an internal skin of silicone (e.g., polydimethylsiloxane). This composite material provides both strength and high oxygen transport. Composite fibers consisting of porous outer layer and an oxygen-permeable layer (here permeable is used in traditional sense of transport by solution of oxygen in the membrane) on the inside of the fiber are preferred for use in extracting oxygen from fluids under pressure, such as seawater. Hollow fibers having interior diameters of 50 microns have been produced, as have much larger hollow fibers having interior diameters of 2 millimeters. Smaller fibers have a greater resistance to pressure, with bursting strengths of 6,000 pounds per square inch having been recorded. In lower pressure environments or when extracting oxygen from air, large diameter fibers are preferred since the larger fibers are rated up to 50 pounds per square inch bursting pressure and offer less resistance to flow, thereby reducing energy required to drive water or air through the fibers where extraction takes place. This is particularly true when large volumes of oxygen are desired to be extracted since a theoretical oxygen extraction of 1 liter per second requires that 3175 gallons of e.g., seawater must contact the membrane surface each minute. Efficiencies of extracting oxygen across membranes of 85% have been obtained in practice.

Preferred membranes of invention, particularly those intended for use in an aqueous environment, should in addition have minimal water and carrier fluid flux. Typically, water flux through membrane is limited by selecting hydrophobic membranes, such as fluorocarbons.

During operation, flow of carrier in contact with the second side of the membrane is balanced against oxygen flux which in turn depends on the oxygen concentration in the environment from which oxygen is being extracted and the rate at which this environment contacts the membrane. Higher oxygen carrier concentrations and faster carrier flow rates both operate to increase the rate of oxygen pick-up. High capacity oxygen carriers are therefore preferred since they decrease the required volume of carrier and minimize pumping requirements.

Loading and unloading devices can be as discussed above, hollow fiber devices. but are not so limited. In addition, other continuous aeration or gas exchange devices may be used, including plate or packed gas-liquid contacting columns, bubble dispersion devices and the like, as discussed for example in Section 18 of the *Chemical Engineers Handbook*, Perry and Chilton, eds., 5th Ed., 1973.

The individual components of an electrochemical cell used in the practice of the method of the invention are readily available to those skilled in the art, although certain combinations of these components have not been previously known. For example, the electrochemical reactions themselves can be conducted in any electrochemical cell which has an anode compartment and a cathode compartment through which the appropriate fluids can be transported. For simplicity in the following discussion, it will be assumed that an oxygen carrier in which the oxygen binding state is a lower oxidation state and the nonbinding state is a higher oxidation state is being used in order to simplify discussion of anode and cathode compartments. However, it will be easily recognized that an oxygen carrier in which the oxygen binding state is a higher oxidation state can readily be used by reversing the anode and cathode.

Although the design of the electrode and cathode compartments of the electrochemical cell are not critical to the practice of this invention, certain embodiments are preferred. For example, a parallel plate electrochemical cell in which anode and cathode compartments alternate in order to increase voltage and decrease current is a preferred embodiment. In order to maximize contact of the carrier fluid containing the oxygen binding compound with the anode and cathode, it is preferred that the anode and cathode compartments have a thickness of no more than 5 millimeters, preferably no more than 1 millimeter. Particularly preferred are porous electrodes, such as vitreous carbon, carbon felt, or polytetrafluoroethylene covered with a thin layer of an inert metal such as gold or platinum. The carrier fluid in such an embodiment passes through the porous electrodes the spaces of which form the anode and cathode compartments.

Pretreatment of the electrode surfaces may, in some embodiments of the invention, be highly desirable. Pretreatment of certain electrodes, such as carbon felt electrodes, used for oxidizing and/or reducing the carrier compounds, leads to differential enhancement, with certain of the carrier compounds of the invention of the power consumption and/or oxidation and/or reduction rates and efficiencies of processing according to the invention. Such pretreatment is described in greater detail in copending application Ser. No. 018,895, filed Feb. 25, 1987, the contents of which are hereby incorporated herein by reference.

The electrochemical cell compartments will contain an inlet and outlet in each anode and cathode compartment through which fluid can be conducted. Of course, one skilled in the art will recognize that anode and cathode compartments can be changed merely by reversing the electrical leads. The present example is illustrated by assuming that the first electrode compartment is an anode compartment and that an oxygen carrier which binds oxygen in the reduced state is being used. A container is attached by means of conduit to the outlet of the anode compartment. The conduit may be a separate tube or may be formed entirely or in part from the walls of the container or the anode compartment. Since oxidation take place in the anode compartment, the anode compartment when in operation will contain the carrier in the oxidized state and free oxygen in solution. Since all oxygen is released by the electrochemical oxidation of the carrier, an extremely high concentration of oxygen can exist in the carrier fluid. Accordingly, in embodiments in which oxygen is released to the internal environment through a ligand-permeable membrane, a positive gradient across the gas-permeable membrane will exist even if air is present on the opposite side of the membrane. It is only necessary that the partial pressure (chemical activity) of oxygen be lower in the internal environment than it is (locally) in the carrier fluid. This is the meaning of "low partial pressure" of the ligand as used in this application in reference to the environment in which the ligand is being released.

The fluid is then transported through a second conduit attached to the container so that fluid which enters the container from the anode compartment contacts the membrane prior to existing the container through the second conduit. This second conduit is attached to an inlet in the cathode compartment and can be formed in the same manner as the first conduit described above. The cathode compartment also contains an outlet through which the fluid passes on its way to pick up oxygen from the environment.

To continue the illustration of releasing oxygen, where oxygen is generally being produced for consumption, it is relatively easy to maintain a low partial pressure of oxygen on the gas-collecting side of the container membrane. If this oxygen is consumed by a human, animal, or fuel burning engine, the result is the same: reduction of the partial pressure of oxygen on the oxygen consuming side of the membrane, which maintains the pressure gradient and the high rate of oxygen removal from the system.

A second specific embodiment, designated electrochemical cell 110, of an apparatus for practicing the methods of the invention is shown schematically in FIG. 10. This electrochemical cell 110 utilizes diffusive and/or convective transport of carrier compound-ligand complexes through an electrolyte solution to transport oxygen (or other ligand) from a first fluid environment from which the ligand is extracted to a second fluid environment to which the ligand released.

Electrochemical cell 110 includes a cathode 112, an anode 114, and an electoylate 116 extending between cathode 112 and anode 114. Electrolyte 116 comprises a carrier fluid as described above containing a trochemical cell 110 is operated to extract a ligand (oxygen, in this example) from a fluid (such as air, in this example) by impressing an appropriate potential across anode 112 and cathode 114 and by introducing air into a first fluid environment, e.g., chamber 118 in fluid communication with electrolyte 116 adjacent cathode 112. This fluid communication may be established, for example, with a ligand-permeable membrane adjacent cathode 112 and separating electrolyte 116 from chamber 118. Alternatively, cathode 112 may be chosen to be ligand-permeable and simultaneously serve as a physical separator between electrolyte 116 and chamber 118. Carrier compound, reduced at cathode 112, binds the ligand thus communicated from chamber 118. (Excess fluid may be expelled from chamber 118 via a vent 120 or the like.) The carrier compound-oxygen complex formed at cathode 112 migrates into and travels through electrolyte 116 under the influence of diffusion, convection, and/or electromigration to anode 114 where the metal of the carrier compound is electrochemically converted to its non-binding valence state and oxygen or other bound ligand is released. Free ligand is collected in a second chamber 122 from which it is withdrawn or consumed, for example, through a vent 124. The released ligand may be diffused through a ligand-permeable membrane to second chamber 122 or anode 114 selected to be ligand-permeable, or may be removed from electrolyte 116 with a bubble dispersion device or the like, as described above.

Of course, it is possible to consume the oxygen without isolating the oxygenic gaseous form. Oxygen in the carrier may be transported to a fuel cell where the oxygen is consumed directly. In a preferred embodiment of the invention, the anode compartment is itself part of the energy-generating field cell as well as being a place where oxygen is released from the carrier so that no transportation is required. Fuel cells are of course well known and can easily be adapted to the process of the present invention. See, for example, U.S. Pat. Nos. 4,215,182 and 4,075,396, and McDougall, *Fuel Cells*, John Wiley & Sons, New York (1976).

When a ligand other than oxygen is being collected at the unloading station, other means of maintaining a low ligand partial pressure (or concentration when the ligand is nonvolatile and is being extracted into a liquid phase) will be required. Generally, some chemical reaction which converts the ligand to a state not free to migrate back into the carrier fluid will be used, or the ligand will be transported away from the membrane by physical means. Chemical reactions for removing ligands (i.g., NO in a waste stream) are already known. The present invention offers advantages over direct contact of a waste stream with these chemical reactants. If the ligand being removed from a waste stream is present only in small quantities, it is possible to concentrate the ligand by utilizing the binding affinity of the ligand carrier and to release the ligand in high concentration for ready reaction with the ultimate removing chemical. The method of the invention also provides a method for readily concentrating minute quantities of material which are to be removed by physical transport, e.g., trapping as a compressed gas or concentrated solution for later disposal.

It is possible to carry out the redox process on the oxygen carrier directly without the intervention of any modifier, promoter, linker, mediator, or other electrocatalyst. However, such materials may be included if desired. A mediator is a small molecule also present in a circulating carrier fluid which serves to transport charge from the electrode surface to the oxygen carrier. A modifier or promoter is a molecule attached to the electrode surface which facilitates electron transfer without itself undergoing a redox reaction. A linker is a molecule which binds the carrier to the electrode surface where the redox process can take place. The advantages, effects, and identities of suitable electrocatalysts for use with carrier compounds according to the present invention are discussed in greater detailing copending application Ser. No. 018,888 filed Feb. 25, 1987, the contents of which are hereby incorporated herein by reference.

The apparatus and method of the invention can be used in any application where it is desirable to remove oxygen from one location and concentrate it in a second location. For example, there are many applications in which the oxygen is present as a contaminant in a fluid, and removal of oxygen therefrom is desired. For example, oxygen degrades food products such as beer, wine, orange juice, and removal of oxygen from these fluids greatly enhances the shelf storage life of the commodity.

In other applications, it is desirable to increase the concentration of oxygen above that which is present in a given environment. For example, persons afflicted with lung disorders who require a high concentration of oxygen for ease of breathing are now mostly limited to bottled oxygen, and movement of such persons is accordingly severely restricted. Miners also need higher oxygen levels than are available under some mining conditions.

Oxygen may also be extracted from water using the apparatus and method of the invention. Typical applications include supplying oxygen to free-swimming divers, to divers in submersible vehicles, to fuel cells which operate under water, and to various energy-consuming engines which require oxygen for combustion processes.

In additional aspects, the present invention relates to the following embodiments:

A polyalkylamine of the general formula

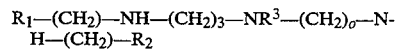

where, $R_1 = R_2 = $ 2-pyridyl;

$o = 2$, 3, or 4;

$R_3$ is hydrogen for $o = 2$ or 4; and $R_3$ is methyl for $o = 3$.

A polyalkylamine of the general formula

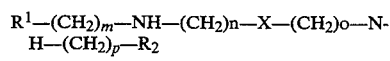

where, $R^1$ and $R^2$ are selected from the group consisting of 2-pyridyl and amino; and X is 2,6-pyridyl.

A metallic complex of a polyalkylamine of the general formula

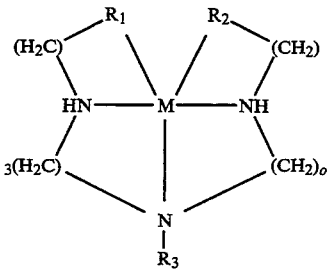

where, $R_1 = R_2 = $ 2-pyridyl;
$o = 2, 3,$ or 4;
$R_3$ is hydrogen for $o = 2$ or 4; and
$R_3$ is methyl for $o = 3$;
M is a transition metal ion.

A metallic complex of a polyalkylamine of the general formula

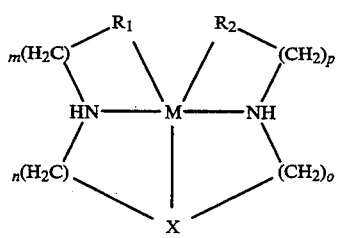

where, each of $R_1$ and $R_2$ is independently selected from the group consisting of 2-pyridyl and amino;
each of m, n, o, and p is independently 1, 2, 3, or 4;
X is 2,6-pyridyl; and
M is a transition metal ion.

A polyalkylamine of the general formula

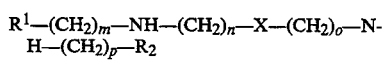

where, each of $R_1$ and $R_2$ is independently an organic group including a sulfur, an oxygen or a nitrogen which is available for coordination to a transition metal ion;
each of m, n, o, and p is independently 1, 2, 3, or 4; and
X is selected from the group consisting of 2,6-pyridyl, 2,6-piperidyl, 2,5-pyrrolyl, 2,4-imidazolyl, substituted heterocyclic amines, —O—, —S—, >P—$R_3$ and >N—$R_3$ where $R_3$ is hydrogen, lower alkyl, or aralkyl; and wherein n and o are unequal.

A metallic complex of a polyalkylamine of the general formula

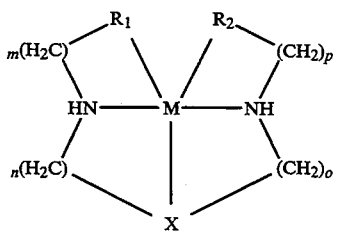

where, each of $R_1$ and $R_2$ is independently an organic group including a sulfer, an oxygen or a nitrogen coordinated to M;
each of m, n, o, and p is independently 1, 2, 3, or 4;
X is selected from group consisting of 2,6-pyridyl; 2,6-piperidyl; 2,5-pyrrolyl; 2,4-imidazolyl, substituted helerocyclic amines, —O—, —S—, >P—$R_3$ and >N—$R_3$ where $R_3$ is hydrogen, alkyl or aralkyl; and M is a transition metal ion, and wherein n and o are unequal.

The metallic complex wherein $R_1$ and $R_2$ is each independently selected from the group consisting of amino, alkylamino, dialkylamino, 2-pyridyl, alkyl-substituted 2-pyridyl, 2-piperidyl, substituted, 2-piperidyl, 2-imidazolyl, 4-imidazolyl, substituted- or 4-imidazolyl, 2-pyrrolyl, alkyl substituted 2-pyrrolyl, 2-pyrazinyl, 2-indolyl, 1-isoindolyl, 3-isoindolyl, 8-quinolinyl, 2-quinolinyl, alkyl-substituted 2- or 8-quinolinyl, 2-thiazolyl, 2-thienyl, substituted 2-thienyl, 2-furyl and substituted 2-furyl.

The metallic complex wherein $R_1$ and $R_2$ is each independently selected from the group consisting of amino, 2-pyridyl, 2-imidazolyl, and 4-imidazolyl.

The metallic complex wherein M is selected from the group consisting of titanium, manganese, chromium, iron, cobalt, nickel, copper, ruthenium, rhodium, palladium, osmium, iridium, vanadium and platinum.

The metallic complex wherein M is selected from the group consisting of manganese, iron, cobalt.

The metallic complex wherein X is 2,6-pyridyl or >N—$R_3$ being hydrogen, lower alkyl, or aralkyl.

A composition of matter for use in electrochemical ligand extraction and generation processes comprising;

an aqueous solution of greater than about 10 millimoles per liter of metallic complex of a polyalkylaminie having the general formula:

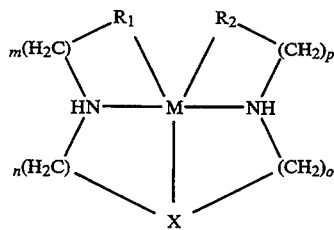

where, each of $R_1$ and $R_2$ is independently an organic group including sulfur, an oxygen or a nitrogen atom coordinated to M;
each of m, n, o, and p is independently 1, 2, 3, or 4;
X is selected from the group consisting of 2,6-pyridyl, 2,6-piperidul, 2,5-pyrrolyl, 2,4-imidazolyl, substituted heterocyclic amines , —O—, —S—, >P—$R_3$, and >N—$R_3$ where $R_3$ is hydrogen, lower alkyl or aralkyl; and
M is a transition metal ion.

The composition of matter wherein M is selected from the group consisting of titanium, manganese, chromium, iron, cobalt, nickel, copper, ruthenium, rhodium, palladium, osmium, iridium, and platinum.

The composition of matter wherein M is selected from group consisting of manganese, iron, cobalt.

The composition of matter wherein $R_1$ and $R_2$ is each selected from the group consisting of amino, alkylamino, dialkylamino, 2-pyridyl, alkyl substituted 2-pyridyl, 2-piperidyl, alkyl substituted 2-piperidyl, 2-imidazolyl, 4-imidazolyl 2-pyrrolyl, alkyl, substituted 2-pyrrolyl, 2-pyrazinyl, 2-indolyl, 1-isoindolyl, 3-isoindolyl, 8-quinolinyl, 2-quinolinyl, alkyl substituted 2 or 8-quinolinyl, 2-thiazolyl, 2-thienyl, substituted 2-thienyl, 2-furyl and substituted 2-furyl.

The composition of matter wherein $R_1$ and $R_2$ is each selected from the group consisting of amino, 2-pyridyl, 2-imidazolyl, and 4-imidazolyl.

The composition of matter wherein X is 2,6-pyridyl or $>N-R_3$, $R_3$ being hydrogen, lower alkyl, or aralkyl.

The composition of matter further comprising a supporting electrolyte.

The composition of matter wherein the supporting electrolyte is a salt selected from the group consisting of sodium chloride, potassium chloride, sodium nitrate, and potassium nitrate.

The composition of matter wherein the supporting electrolyte is a salt having a concentration between about 0.1 and about 1.0 molar.

The composition of matter wherein the aqueous solution has a pH of between about 3 and about 12.

The composition of matter titrated to a pH unit above the pH at which greater than about 50% of the metallic complex, when exposed to an oxygen containing environment, is present as an oxygen complex.

A method for extracting a ligand from a first fluid environment, the method comprising the steps of:

contacting first fluid environment containing ligand with the first surface of a first ligand-permeable membrane having a first and second surface wherein the membrane separates the environment from an interior space of container;

contacting a carrier fluid with a second surface of the membrane wherein the carrier fluid is confined in the container and the carrier fluid contains a carrier compound, whereby at least a position of a ligand which diffuses through the membrane binds to the carrier compound to give bound ligand complex;

transporting the carrier fluid containing the bound ligand complex to a first electrode compartment of an electrochemical cell which forms a second portion of the container;

electrochemically modulating the carrier compound to an oxidation state having relatively less binding affinity for ligand, thereby releasing free ligand into the carrier fluid and producing a non-binding state carrier compound;

removing ligand from the carrier fluid to give a ligand depleted carrier fluid;

transporting the ligand depleted carrier fluid containing the non-binding state carrier compound to a second electrode compartment of an electrochemical cell which forms a third portion of the container; and electrochemically modifying the non-binding state carrier compound to reform the binding state carrier compound;

wherein, the carrier compound comprises a metallic complex of a polyalkylamine having a general formula:

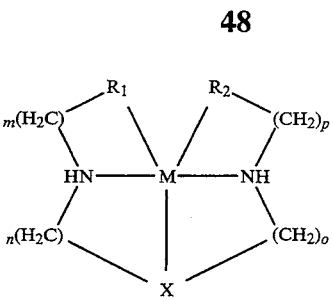

where, each of $R_1$ and $R_2$ is independently an organic group including a sulfur, an oxygen or a nitrogen atom coordinated to M;

each of m, n, o, and p is independently 1, 2, 3, or 4;

X is selected from the group consisting of 2,6-pyridyl, 2,6-piperidyl, 2,5-pyrrolyl, 2,4-imidazolyl, substituted heterocyclic amines, $-O-$, $-S-$, $>P-R_3$, and $>N-R_3$ where $R_3$ is hydrogen, lower alkyl, or aralkyl; and M is a transition metal ion.

The method for extracting further comprising the step of transporting the carrier fluid containing the non-binding state carrier compound and free ligand to a fourth portion of the containing in which ligand is removed from the carrier fluid to yield the ligand-depleted carrier fluid.

The method of extracting wherein the ligand removing step comprises contacting the carrier fluid with a second ligand-permeable membrane which separates the carrier fluid from a second fluid environment.

The method wherein the ligand comprises molecular oxygen.

The method of extraction wherein the carrier fluid comprises primarily water and includes, in addition to the carrier compound, a supporting electrolyte and is buffered to a selected pH.

A method of extraction for extracting a ligand from a first fluid environment and releasing the ligand to a second fluid environment, the method comprising the steps of:

providing an electrochemical cell including an anode, a cathode, and an electrolyte comprising a transition metal carrier compound having the general formula:

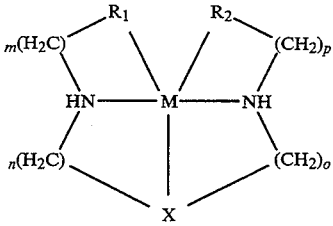

where, each of $R_1$ and $R_2$ is independently an organic group including a sulfur, an oxygen or a nitrogen atom coordinated to M;

each of m, n, o, and p is independently 1, 2, 3, or 4;

X is selected from the group consisting of 2,6-pyridyl, 2,6-piperidyl, 2,5-pyrrolyl, 2,4-imidazolyl, substituted heterocyclic amines, $-O-$, $-S-$, $>P-R_3$, and $>N-R_3$ where $R_3$ is hydrogen, lower alkyl, or aralkyl; and M is a transition metal ion;

providing a potential across the cell sufficient to convert the metal of the carrier compound to a binding valence state at the cathode and convert, at the anode, the metal of a carrier compound ligand complex to a non-binding valence state:

communicating the ligand from the first fluid environment to the electrolyte in the region of the cathode so that the carrier compound ligand complex is formed between the ligand and the binding valence state carrier compound;

transporting the carrier compound ligand complex to the anode for release of the ligand; and The method of extraction further comprising the step of electrochemically releasing the ligand from the carrier compound ligand complex to the second fluid environment.

While the above is a complete description of the preferred embodiments of the invention, other arrangements and equivalents are possible and may be employed without departing from the true spirit and scope of the invention. Therefore the description and illustrations should not be construed as limiting the scope of the invention, which is delineated by the appended claims.

We claim:

1. An improved process to produce a symmetrical or an unsymmetrical prechelate compound of Structure I:

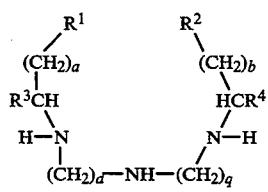

or a salt thereof, wherein $R^1$ and $R^2$ are each independently selected from aliphatic, alicyclic, or aromatic organic compounds each containing at least one nitrogen, or sulfur or oxygen atom which is suitable for coordination to a transition metal ion, with the proviso that $R^1$ and $R^2$ are independently the same or different chemical groups, $R^3$ and $R^4$ are each independently selected from —H or —$CH_3$, a and b are each independently 0, 1 or 2, d and q are each independently selected from 1, 2, 3, 4 or 5, which process comprises:

(a) contacting about one equivalent a compound of the structure:

with about one equivalent of $R^1$—$(CH_2)_a(C=O)R^3$ where $R^1$, a, d and q are defined above, in an anhydrous organic solvent capable of forming an azeotrope with water and molecular sieves or under elevated temperature reflux and azeotropic conditions sufficient to remove water and to produce a compound of Structure II;

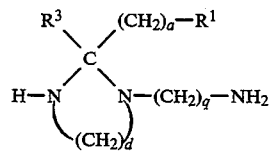

(b) contacting the product of step (a) with about one equivalent of $R^2$—$(CH_2)_b(C=O)R^4$, wherein b, $R^2$ and $R^4$ are defined hereinabove in an anhydrous organic solvent capable of forming an azeotrope with water and molecular sieves or under elevated temperature reflux and azeotropic conditions effective to essentially remove all of the water produced by the condensation;

(c) removing the organic solvent to isolate the imine intermediate;

(d) contacting the imine intermediate with a second anhydrous organic solvent under hydride reducing conditions effective to selectively reduce the imine; and (e) recovering the compound of structure (I).

2. The process of claim 1 wherein $R^1$ and $R^2$ are the same chemical group.

3. The process of claim 1 wherein $R^1$ and $R^2$ are different chemical groups each containing at least one nitrogen atom.

4. The process of claim 3 wherein structure I is a symmetrical prechelate compound where a=b and d=q.

5. The process of claim 2 wherein $R^1$ and $R^2$ each contain at least one nitrogen atom.

6. The process of claim 1 wherein structure I is an unsymmetrical prechelate compound, where $R^1 \neq R^2$, $R^3=R^4=H$, a=b=0 and d≠q.

7. The process of claim 3 wherein $R^1$ and $R^2$ each contain at least one aromatic nitrogen atom, $R^3=R^4=H$, a=b=0, and d=q.

8. The chemical product of structure (I) produced by the process of claim 1.

9. An improved process to produce an unsymmetrical prechelate compound of Structure I:

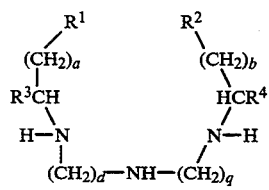

or a salt thereof, wherein $R^1$ and $R^2$ are each independently selected from aliphatic, alicyclic, or aromatic organic compounds each containing at least one nitrogen atom which is suitable for coordination to a transition metal ion, with the proviso that $R^1$ and $R^2$ are each independently different chemical groups containing an aromatic nitrogen atom, $R^3$ and $R^4$ are each independently —H, a and b are each 0, d and q are each independently selected from 1, 2, 3, 4 or 5 and d=q, which process comprises:

(a) contacting about one equivalent a compound of the structure:

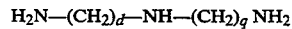

with about one equivalent of $R^1$—$(CH_2)_a(C=O)R^3$ where $R^1$, $R^3$, a, d and q are defined above, in an anhydrous organic solvent capable of forming an azeotrope with water and either molecular sieves or under elevated temperature reflux and azeotropic conditions sufficient to remove water and to produce a compound of Structure II;

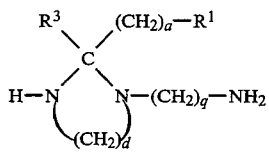

(b) contacting the product of step (a) with about one equivalent of $R_2$—$(CH_2)_b(C=O)R^4$, wherein b, $R^2$ and $R^4$ are defined hereinabove in an anhydrous organic solvent capable of forming an azeotrope with water and either with molecular sieves or under elevated temperature reflux and azeotropic conditions effective to essentially remove all of the water produced by condensation;

(c) removing the organic solvent to isolate the imine intermediate;

(d) contacting the imine intermediate with a second anhydrous organic solvent under hydride reducing conditions effective to selectively reduce the imine; and (e) recovering the compound of structure (I).

10. The process of claim 9 wherein in step (d) the reducing conditions are selected from sodium borohydride or catalytic hydrogen using palladium/carbon catalyst.

11. The compound product of structure I of claim 7.

12. The compound product of structure I of claim 9.

13. An organic compound of the general structure (I):

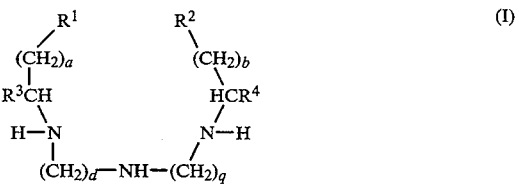

wherein $R^1$ and $R^2$ are each independently selected from aliphatic, alicyclic, or aromatic organic groups which contain at least one nitrogen, or sulfur, or oxygen atom which is suitable for coordination to a transition metal ion, with the proviso that $R^1$ and $R^2$ are the same or different chemical groups;

a and b are each independently 0, 1 or 2;

$R^3$ and $R^4$ are each independently —H or —$CH_3$; and d and q are each independently selected from 1, 2, 3, 4 or 5.

14. The organic compound of claim 13 wherein $R^1$ and $R^2$ are different groups each containing at least one nitrogen atom, $R^3=R^4=H$ a=b=0, and d=q selected from 1, 2 or 3.

15. The organic compound of claim 14 wherein the organic nitrogen group is selected from 2-pyridyl; 2-(6-methyl)pyridyl; 2-piperidyl; substituted 2-piperidyl; 2-imidazolyl; 4-imidazolyl; substituted 2- or 4-imidazolyl; 2-(1-methylimidazolyl), 2-benzimidazolyl, 2-(1-benzylimidazolyl) and 4-(5-methylimidazolyl); 2-pyrrolyl; alkyl-substitutued 2-pyrrolyl; 2-pyrazinyl; 2-indolyl; 1-isoindolyl; 3-isoindolyl; 2-quinolinyl; 8-quinolinyl; alkyl-substitutued 2- or 8-quinolinyl; or 2-thiazolyl.

16. The organic compound of claim 15 wherein $R^1$ and $R^2$ are aromatic groups.

* * * * *